US011359206B2

(12) United States Patent
Cho et al.

(10) Patent No.: US 11,359,206 B2

(45) Date of Patent: Jun. 14, 2022

(54) LEGHEMOGLOBIN IN SOYBEAN

(71) Applicant: PIONEER HI-BRED INTERNATIONAL, INC., Johnston, IA (US)

(72) Inventors: Hyeon-Je Cho, Ankeny, IA (US); John D Everard, Grimes, IA (US); Anthony J Kinney, Wilmington, DE (US); Zhan-Bin Liu, Clive, IA (US); Knut Meyer, Wilmington, DE (US); Thomas G Patterson, Westfield, IN (US); Kevin G Ripp, Des Moines, IA (US); Bo Shen, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/557,353

(22) Filed: Dec. 21, 2021

(65) Prior Publication Data

US 2022/0127632 A1 Apr. 28, 2022

Related U.S. Application Data

(63) Continuation of application No. 17/451,913, filed on Oct. 22, 2021.

(60) Provisional application No. 63/106,519, filed on Oct. 28, 2020.

(51) Int. Cl.
*C12N 15/82* (2006.01)
*C07K 14/415* (2006.01)

(52) U.S. Cl.
CPC ........ *C12N 15/8251* (2013.01); *C07K 14/415* (2013.01)

(58) Field of Classification Search
None
See application file for complete search history.

(56) References Cited

U.S. PATENT DOCUMENTS 9,700,067 B2 7/2017 Fraser et al.
9,737,875 B2 8/2017 Brown et al.
9,808,029 B2 10/2017 Fraser et al.
9,826,772 B2 11/2017 Fraser et al.
9,833,768 B2 12/2017 Brown et al.
9,943,096 B2 4/2018 Fraser et al.
10,039,306 B2 * 8/2018 Vrljic ...................... A23L 27/26
10,087,434 B2 10/2018 Kale et al.
10,093,913 B2 10/2018 Kale et al.
10,172,380 B2 1/2019 Varadan et al.
10,287,568 B2 5/2019 Kale et al.
2006/0053515 A1 3/2006 Geigenberger et al.
2011/0243975 A1 10/2011 Terakawa et al.
2011/0263023 A1 10/2011 Mccarthy et al.
2015/0289541 A1 10/2015 Brown et al.
2016/0340411 A1 11/2016 Fraser et al.
2017/0342131 A1 11/2017 Fraser et al.
2017/0342132 A1 11/2017 Fraser et al.
2018/0027851 A1 2/2018 Vrljic et al.
2018/0199605 A1 7/2018 Fraser et al.
2018/0199606 A1 7/2018 Fraser et al.
2019/0008192 A1 1/2019 Brown et al.
2019/0021337 A1 1/2019 Von Maltzahn et al.
2019/0116855 A1 4/2019 Vrijic et al.
2019/0133162 A1 5/2019 Varadan et al.
2019/0133163 A1 5/2019 Varadan et al.
2019/0200658 A1 7/2019 Vrijic et al.
2019/0292217 A1 * 9/2019 Davis ................. C12N 15/8257
2019/0292555 A1 9/2019 Davis et al.

FOREIGN PATENT DOCUMENTS

WO 2013/155555 A1 10/2013
WO 2015/017510 A1 2/2015
WO 2022/072833 A2 4/2022
WO 2022072846 A2 4/2022

OTHER PUBLICATIONS

Genome.gov. Genetics Glossary: Recombinant DNA (rDNA). https://www.genome.gov/genetics-glossary/Recombinant-DNA. Accessed Mar. 8, 2022 (Year: 2022).*
Cao et al. GenBank: AAA82069.1 (Year: 1995).*
Stougaard, J.; et al.: "Expression of a complete soybean leghemoglobin gene in root nodules of transgenic Lotus corniculatus," Proceedings of the National Academy of Sciences of the U.S.A., Aug. 1987, vol. 84, No. 16, pp. 5754-5757.

(Continued)

*Primary Examiner* — Matthew R Keogh
*Assistant Examiner* — David R Byrnes

(57) ABSTRACT

Soybean plants producing soybean seeds comprising leghemoglobin are produced by modifying the genome of the soybean plant. Soybean plants, soybean seeds and soy protein compositions comprising leghemoglobin are provided. Soybean plants, soybean seeds and soy protein compositions comprising leghemoglobin and additionally one or more of high oleic acid, low linolenic acid, high protein, low stachyose, low raffinose and low protease inhibitors are provided. Protein compositions comprising leghemoglobin, such as soy isolates and concentrates can be made from the soybean seeds. Additionally, methods for generating and using plants, seeds and protein compositions comprising leghemoglobin are disclosed.

19 Claims, 14 Drawing Sheets

Specification includes a Sequence Listing.

(56) References Cited

OTHER PUBLICATIONS

International Search Report and Written Opinion for International Application No. PCT/US21/71984, dated Jan. 27, 2022.
U.S. Appl. No. 63/087,146, filed Oct. 2, 2020, "Transgenic Plants With Altered Fatty Acid Profiles and Upregulated Heme Biosynthesis".
U.S. Appl. No. 63/180,849, filed Apr. 28, 2021, "Transgenic Plants With Altered Fatty Acid Profiles and Upregulated Heme Biosynthesis".

* cited by examiner

No signal Peptide

Conglycinin SPP

Lectin SP

GY1 SP/GY1 Basic Subunit

No signal Peptide

Conglycinin SPP

Lectin SP

GY1 SP/GY1 Basic Subunit

| GH # | | Event |
|---|---|---|
| GH129096520 | GMZ3A9.1.20 | 400874629 |
| GH129096522 | GMZ3A9.1.22 | 400874631 |
| GH129096519 | GMZ3A9.1.24 | 400874633 |
| GH129096521 | GMZ3A9.1.30 | 400874639 |
| GH129096518 | GMZ3A9.1.34 | 400874643 |

GM9RDV.001.18a; #21
GM9RDV.001.5a: #14 WT

GM9RDV.001.26a; #42
GM9RDV.001.5a; #14 WT

GM9RDV.001.5a; #11
GM9RDV.001.5a: #14 WT

GM9RDV.001.20a; #33
GM9RDV.001.5a: #14 WT

LEGHEMOGLOBIN IN SOYBEAN

REFERENCE TO SEQUENCE LISTING SUBMITTED ELECTRONICALLY

The official copy of the sequence listing is submitted electronically via EFS-Web as an ASCII formatted sequence listing with a file named 8429-US-PSP_SequenceListing_ST25.txt created on Oct. 28, 2020 and having a size of 94 kilobytes and is filed concurrently with the specification. The sequence listing comprised in this ASCII formatted document is part of the specification and is herein incorporated by reference in its entirety.

BACKGROUND

Animal-based meat replacement with plant-based proteins is becoming an industrial trend in food applications. Soy legume hemoglobin, or leghemoglobin, is a globin protein found in the nitrogen-fixing root nodules of leguminous plants. It carries heme, an iron-containing molecule, and functions to protect the nitrogenase enzyme from oxygen inactivation and to facilitate oxygen flow to the nitrogen-fixing bacteria. Leghemoglobin can be fermented from engineered yeast and has use in meat replacements by mimicking the flavor contributed by hemoglobin in meat. Compositions and methods to express leghemoglobin in soybeans are provided.

SUMMARY

Soybean seeds are provided which contain a leghemoglobin protein in an amount of at least 0.5% of total protein in the soybean seed, without the leghemoglobin being expressed from a recombinant construct comprising a leghemoglobin coding sequence integrated into the soybean genome. The soybean seed genome which does not comprise a recombinant construct containing a leghemoglobin coding sequence can be modified to introduce an insertion, deletion or substitution into a native leghemoglobin gene, such as the coding sequence or regulatory sequence or modified to replace all or part of a coding sequence of a seed storage protein with a leghemoglobin coding sequence.

Soybean seeds are provided in which the soybean seed genome is modified to introduce an insertion, deletion or substitution into a native leghemoglobin gene or modified to replace all or part of a coding sequence of a seed storage protein with a leghemoglobin coding sequence.

In some embodiments, a targeting sequence such as a transit peptide is operably linked to a leghemoglobin coding sequence to direct the leghemoglobin to an intracellular compartment such as a plastid.

In some embodiments, a soybean seed comprising a genomic modification is provided in which the leghemoglobin protein is expressed in the soybean seed in an amount sufficient to impart a pink color to the soybean seed in a transverse section of the seed or in an amount of at least 0.1% of the total seed protein.

In some embodiments the soybean is modified to directly express leghemoglobin specifically in the seed plastids.

In some embodiments, the soybean seed having one or more of a modification in the native leghemoglobin gene, an insertion of the leghemoglobin gene under the control of a different native promotor in the nuclear genome, or inclusion of the leghemoglobin sequence in the plastid genome, further comprises a recombinant construct comprising a leghemoglobin coding sequence integrated into its genome.

In some embodiments, the soybean seed contains further modifications such as nucleotide insertions, deletions, or substitutions into one or more genes encoding a glutamyl tRNA reductase, a ferrochetalase, a glutamyl tRNA reductase binding protein and an aminolevulinic acid synthase. In some embodiments, the soybean seed contains one or more recombinant constructs containing a coding sequence for a glutamyl tRNA reductase, a ferrochetalase, a glutamyl tRNA reductase binding protein and/or an aminolevulinic acid synthase.

Provided are soybean seeds which contain a leghemoglobin protein in an amount of at least 0.5% of total seed protein and which have one or more of the following characteristics: (i) an oleic acid content of at least 50% of the total seed fatty acids; (ii) a linolenic acid content of less than 3% of the total seed fatty acids; (iii) a protein content of at least 37% of the total weight of the soybean measured at or adjusted to 13% moisture; (iv) a Kunitz Trypsin protease inhibitor activity of less than 5% of that of a control unmodified soybean; (v) a Bowman-Burke protease inhibitors activity of less than 5% of a control unmodified soybean; (vi) a stachyose content of less than 1% weight percent at 13% moisture; and (vii) a raffinose content of less than 0.5% weight percent at 13% moisture.

In some embodiments, transgenic soybean seeds are provided which contain a recombinant construct comprising a polynucleotide encoding a leghemoglobin protein having at least 95% identity to SEQ ID NO: 2, in which the construct does not comprise a protein storage vesicle targeting sequence, and wherein the soybean does not contain (i) a recombinant construct comprising a sequence encoding a glutamyl tRNA reductase, or a truncated portion thereof, (ii) a recombinant construct comprising a sequence encoding a ferrochetalase, (iii) a recombinant construct comprising a glutamyl tRNA reductase binding protein and (iv) a recombinant construct comprising an aminolevulinic acid synthase, and wherein the soybean seed comprises leghemoglobin in the seed in an amount of at least 0.5% total seed protein.

In some embodiments, soybean seeds containing leghemoglobin protein in an amount of at least 0.5% of total protein have a genomic modification which includes at least one of (i) a nucleic acid insertion of a soybean genomic sequence which insertion excludes a non-soybean genomic sequence, (ii) one or more nucleic acid substitutions, (iii) one or more nucleic acid deletions, and (iv) any combination thereof, wherein the genomic modification comprises (a) a modification made to the native leghemoglobin gene or (b) an insertion comprising at least a portion of the native leghemoglobin gene.

In some embodiments, the soybean expresses leghemoglobin and further comprises a different modification to reduce or prevent expression of one or more seed storage coding sequences, such as a glycinin or a conglycinin.

In some embodiments, the soybean expresses leghemoglobin and further comprises one or more of high oleic acid, low linolenic acid, at least 37% total seed protein at 13% moisture.

In some embodiments, plants and plant parts grown from the modified soybean seeds containing leghemoglobin are provided.

In some embodiments, methods for processing soybean meal extracted from the modified soybean seeds which express leghemoglobin are provided in which the meal is contacted with at least one of a cellulase, a hemicellulase, and a pectinase under conditions sufficient to degrade the polysaccharides in the meal and the permeant is filtered from the residue. Meal extracted from the modified soybean seeds is provided containing at least 0.1%, 0.2%, 0.3%, 0.4% or 0.5% leghemoglobin by wt total protein.

In some embodiments, soybean isolate comprising at least 0.2% leghemoglobin by weight of total protein, with at least about 50% of the leghemoglobin being hemelated with an iron group is provided, which is produced from the modified seeds expressing leghemoglobin.

In some embodiments, a method is provided for producing soybean meal or isolate from modified soybean seeds comprising leghemoglobin and soybean seeds comprising high oleic acid in which the beans are processed to produce meal or isolate, comprising high oleic acid and leghemoglobin in which at least about 50% of the leghemoglobin is hemelated with an iron group.

BRIEF DESCRIPTION OF THE DRAWINGS AND THE SEQUENCE LISTING

The disclosure can be more fully understood from the following detailed description and the accompanying drawings and Sequence Listing, which form a part of this application.

Figure 11:
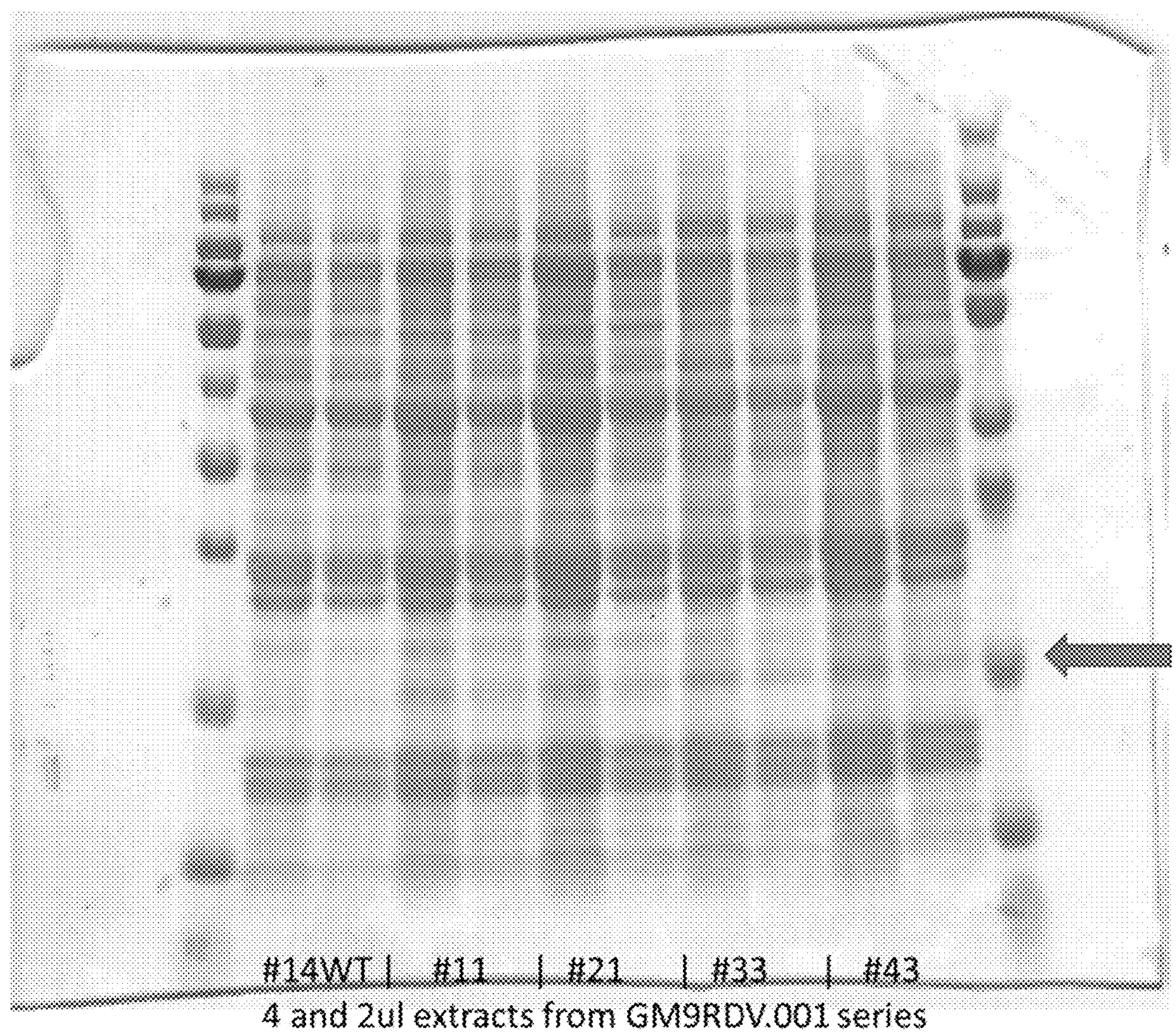

FIG. 11 a photograph of a Coomassie-stained protein gel showing the presence of 16KD leghemoglobin protein in experiment 5.

Figure 12:
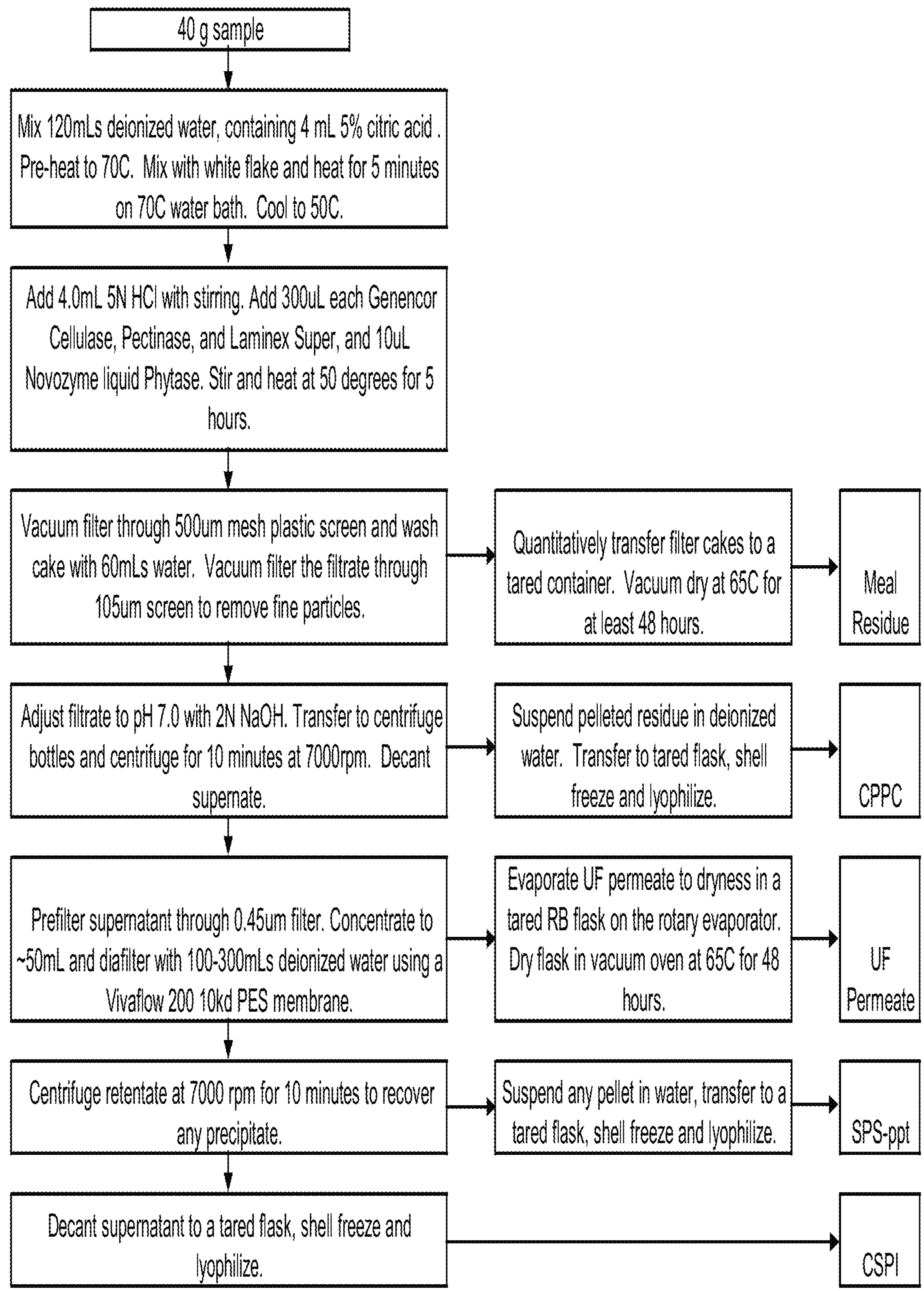

FIG. 12 is a schematic flow chart showing an example of a generalized process for the Enzymatic Soybean Processing (E-SOY) process.

Figure 13:
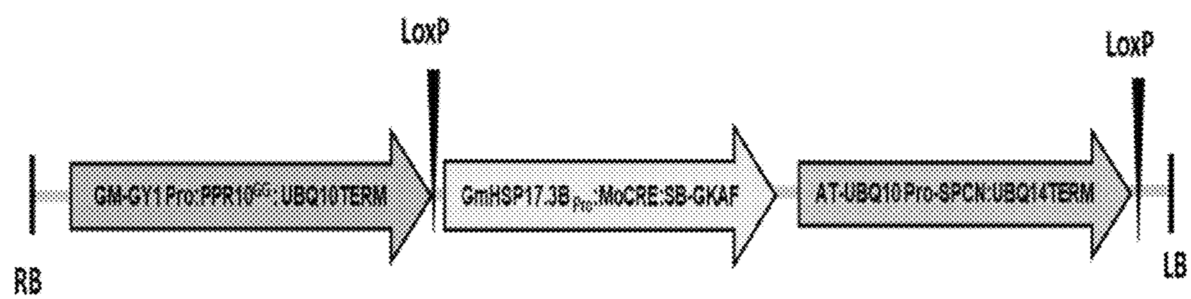

FIG. 13 is a schematic diagram showing a soybean nuclear transformation binary vector within the T-DNA.

Figure 14:
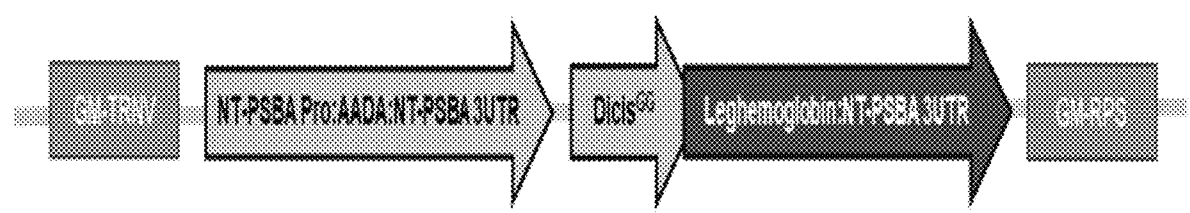

FIG. 14 is a schematic diagram of soybean chloroplast transformation vector.

DETAILED DESCRIPTION

The sequence descriptions (Table 1) summarize the Sequence Listing attached hereto, which is hereby incorporated by reference. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

TABLE 1

Sequence Listing Description

| SEQ ID NO: | Name | Type |
|---|---|---|
| 1 | Glyma.20g191200 Leghemoglobin CDS | DNA |
| 2 | Glyma.20g191200 Leghemoglobin peptide | PRT |
| 3 | Beta-conglycinin SPP-Leghemoglobin CDS | DNA |
| 4 | Beta-conglycinin SPP-Leghemoglobin peptide | PRT |
| 5 | Lectin SP-Leghemoglobin CDS | DNA |
| 6 | Lectin SP-Leghemoglobin Peptide | PRT |
| 7 | GY1 SP-leghemoglobin-GY1 basic subunit CDS | DNA |
| 8 | GY1 SP-leghemoglobin-GY1 basic subunit peptide | PRT |
| 9 | beta-conglycinin promoter | DNA |
| 10 | glycinin promoter | DNA |
| 11 | Glyma.04g0898000 CDS | DNA |
| 12 | Glyma.04g0898000 peptide | PRT |
| 13 | Glyma.04g050400 CDS | DNA |
| 14 | Glyma.04g050400 Peptide | PRT |
| 15 | Phaseolin promoter | DNA |
| 16 | Napin Promoter | DNA |
| 17 | GM-GY1-CR1 | RNA |
| 18 | GM-GY1-CR2 | RNA |
| 19 | GM-GY1-CR3 | RNA |
| 20 | glyma.03g163500 Glycinin 1 gene | DNA |
| 21 | glyma.03g163500 Glycinin 1 peptide | PRT |
| 22 | Donor DNA for GM-GY1-CR1/CR2 design | DNA |
| 23 | Donor DNA for GM-GY1-CR1/CR3 design | DNA |
| 24 | GM-CONG-gRNA1 | RNA |
| 25 | GM-CONG-gRNA2 | RNA |
| 26 | GM-CONG-gRNA3 | RNA |
| 27 | GM-CONG-gRNA4 | RNA |
| 28 | GM-CONG-gRNA5 | RNA |
| 29 | GM-CONG-gRNA6 | RNA |
| 30 | GM-CONG-gRNA7 | RNA |
| 31 | Rubisco SSUSP::LH | DNA |
| 32 | Rubisco SSUSP::LH | PRT |
| 33 | Globulin peptide | PRT |
| 34 | Globulin peptide | PRT |
| 35 | Glyma.04G037000.1 CDS urophorphyrinogen III synthase | DNA |
| 36 | Glyma.04G037000.1 polypeptide urophorphyrinogen III synthase | PRT |
| 37 | glutamate-1-semialdehyde 2,1-aminomutase Glyma.04G002900.1 | DNA |
| 38 | glutamate-1-semialdehyde 2,1-aminomutase Glyma.04G002900.1 | PRT |
| 39 | Glutamyl-tRNA reductase-binding protein Glyma.08G222600 | DNA |
| 40 | Glutamyl-tRNA reductase-binding protein Glyma.08G222600 | PRT |
| 41 | chloroplast signal particle 43 Glyma.11G097200 | DNA |
| 42 | chloroplast signal particle 43 Glyma.11G097200 | PRT |
| 43 | Glyma.20g191200 leghemoglobin genomic sequence | DNA |
| 44 | Disis GG artificial sequence | DNA |
| 45 | Maize PPR protein CDS coding sequence | DNA |
| 46 | Maize PPR protein polypetide sequence | PRT |
| 47 | Soybean PPR protein CDS coding sequence Glyma.15g162500 | DNA |
| 48 | Soybean PPR protein polypetide sequence Glyma.15g162500 | PRT |

The present disclosure describes modified soybean seeds expressing the leghemoglobin protein, the leghemoglobin complex or a combination thereof. Leghemoglobin is a protein synthesized in soy root nodules upon colonization by nitrogen-fixing bacteria. As used herein, "leghemoglobin protein" or "leghemoglobin" refer to the globulin protein or polypeptide, whether unfolded or folded into a monomer and which may or may not have associated with it a heme group (porphyrin bound to iron). As used herein "leghemoglobin complex" or "leghemoglobin protein complex" refers particularly to the complex which includes the leghemoglobin protein associated with a heme group (porphyrin bound to iron). Such a complex, when present in sufficient quantities can impart a red or pink color to the cells or tissue containing the complex, detectable to the eye, such as in the transverse section of a soybean seed expressing leghemoglobin complex. As used herein with respect to the color of a soybean in the transverse section, pink color means any shade of pink or red.

The soybean seeds can be modified to increase expression of leghemoglobin which forms a heme complex without the need to target expression of the leghemoglobin to a protein storage vesicle or other targeted cellular compartment.

In some embodiments the leghemoglobin without a heme group, the leghemoglobin complex, or a combination of both forms can be present in soybean seeds at at least 0.01%, 0.05%, 0.5%, 1%, 1.5%, 2%, 2.5%, 3%, 4%, 5%, 6%, 7%, 8%, 9%, 10% or more and less than 75%, 50%, 25%, 20%, 15%, 10%, 5%, 4% or 3% of the total seed protein.

Suitably at least 5, 10, 15, 20, 25, 30, 40, 50, 60, 70, 80, 90 or 95 percent and less than 100, 99.9, 95, 90, 85, 80, 70, 60 or 50 percent of the total leghemoglobin forms a complex with a heme group in the soybean seed.

Soybean seeds disclosed herein, as well as plant parts, plant cells, tissue cultures and plants grown therefrom are provided.

In certain embodiments, the soybean seeds have introduced a recombinant construct comprising a leghemoglobin coding sequence operably linked to a promoter functional in a soybean seed cell. As used herein a recombinant construct is a construct that includes a promoter sequence operably linked to a polynucleotide encoding a polypeptide, and optionally other regulatory sequences wherein the recombinant construct is exogenous to the plant, plant cell or seed. As used herein, the term "exogenous" with respect to a nucleic acid indicates that the nucleic acid is not in its natural genomic location. Such plants containing recombinant constructs are referred to as transgenic plants. A regulatory sequence can be a sequence in or around a gene which promotes transcription or termination of polypeptide coding sequences.

Non-limiting examples of recombinant DNA constructs include a polynucleotide of interest operably linked to heterologous sequences, also referred to as "regulatory elements," which aid in the expression, autologous replication, and/or genomic insertion of the sequence of interest. Such regulatory elements include, for example, promoters, termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The recombinant DNA constructs or recombinant constructs provided comprise at least one regulatory element that when integrated into the genome is not present in its native location in the soybean genome or is from the genome of another species. In certain embodiments, the at least one regulatory element of the recombinant DNA construct comprises a promoter, preferably a heterologous promoter that drives expression of the leghemoglobin in seeds, such as a glycinin or conglycinin promotor.

In an embodiment, the soybean seed containing a recombinant construct comprising a leghemoglobin coding sequence do not contain one or more or all of the following (i) a recombinant construct comprising a sequence encoding a glutamyl tRNA reductase, or a truncated portion thereof, (ii) a recombinant construct comprising a sequence encoding a ferrochetalase, (iii) a recombinant construct comprising a glutamyl tRNA reductase binding protein and (iv) a recombinant construct comprising an aminolevulinic acid synthase. A truncated coding sequence is a sequence that has had the N' or C' terminus, or both, of the coding sequence removed such that a polypeptide is synthesized from the coding sequence that is shorter than the native non-truncated polypeptide and lacks a number of amino acids at the C' terminus the N' terminus or both. The inventors discovered that high levels of leghemoglobin and leghemoglobin complex could be expressed in soybean seeds in amounts detectable by eye through conferring a pink color without the need to augment expression with these additional recombinant constructs and without the need to include a targeting sequence that would direct the leghemoglobin to a particular cellular compartment, such as a protein storage vesicle.

In some embodiments the native leghemoglobin gene is modified. The genomic sequence of the leghemoglobin gene is provided in SEQ ID NO:43 and modifications may be made to or include all or part of this sequence or to a sequence corresponding to SEQ ID NO: 43 in the soybean genome, including to specific regions identified herein. With respect to SEQ ID NO: 43, the regulatory region, including the promotor and 5' UTR, is from nucleotide position 1 to position 2058, exon 1 is from position 2059 to position 2156, intron 1 is from position 2157 to position 2275, exon 2 is from position 2276 to position 2384, intron 2 is from position 2385 to position 2574, exon 3 is from position 2575 to position 2679, intron 3 is from position 2680 to position 2876, exon 4 is from position 2877 to position 3002, the terminator, including the 3' UTR, is from position 3003 to position 5214.

In some embodiments, the modification is made from position 1-2058 of SEQ ID NO:43, 100-2058 of SEQ ID NO:43, 200-2058 of SEQ ID NO:43, 300-2058 of SEQ ID NO:43, 400-2058 of SEQ ID NO:43, 500-2058 of SEQ ID NO:43, 600-2058 of SEQ ID NO:43, 700-2058 of SEQ ID NO:43, 800-2058 of SEQ ID NO:43, 900-2058 of SEQ ID NO:43, 1000-2058 of SEQ ID NO:43, 1100-2058 of SEQ ID NO:43, 1200-2058 of SEQ ID NO:43, 1300-2058 of SEQ ID NO:43, 1400-2058 of SEQ ID NO:43, 1500-2058 of SEQ ID NO:43, 1600-2058 of SEQ ID NO:43, 1700-2058 of SEQ ID NO:43, 1800-2058 of SEQ ID NO:43, or 1900-2058 of SEQ ID NO:43.

In some embodiments, the plastid genome of the soybean seed comprises a modification in which a sequence encoding a leghemoglobin protein is inserted into the plastid genome, such that the leghemoglobin polypeptide is expressed directly in the seed plastids without the need for a transit peptide. Seed-specific plastid transformation can be achieved by inserting a construct comprising the leghemoglobin coding sequence connected to a DicisGG sequence such as SEQ ID NO: 44. The plant is co-transformed to express a PPR protein, such as a PPR10 protein such as SEQ ID NO: 46 or 48, with the sequence encoding the PPR protein under the control of a promotor active in the seed and which is seed-specific, such as a promotor of a seed storage protein such as glycinin or conglycinin. Different seed-specific promotors can be selected to modulate the amount of expression of the PPR protein. Alternatively, expression of the PPR protein can be achieved through genome editing to replace all or part of a native sequence which is expressed in a seed specific fashion, such as at the locus of a seed storage protein. The PPR protein acts as a trigger in the seed for the DicisGG sequence to facilitate direct expression of the leghemoglobin in the seed plastids, without or with little or minimal expression occurring in non-seed plant parts such as the roots, stems, leaves and flowers.

The plastid expression of leghemoglobin can be combined with expression of leghemoglobin from a nuclear genomic source, such as by transformation of the nuclear genome with a transgenic construct, or by genome editing of a native nuclear gene, such as by inserting, deleting or substituting one or more nucleotides into the native leghemoglobin gene or by genome editing of a gene highly expressed in the soybean seed such as by inserting the leghemoglobin sequence into a seed storage protein gene to replace all or part of the coding sequence of the seed storage protein such that the leghemoglobin is expressed instead of the seed storage protein. The plastid expression of leghemoglobin can be combined with increased or decreased expression of other genes encoding or contributing to the control of the heme biosynthesis pathway, such as disclosed herein.

In some embodiments, an intracellular targeting sequence or transit sequence such as a plastid targeting sequence is included and operably linked to a sequence encoding leghemoglobin, such as being placed just before the N' terminus of a sequence encoding leghemoglobin, such that the intracellular targeting sequence targets expression of the leghemoglobin to an intracellular compartment such as a protein storage vesicle or a plastid. The targeting sequence and operably linked leghemoglobin sequence, such as occurs in SEQ ID NO: 31 or a polynucleotide encoding SEQ ID NO: 32, can be operably linked to a regulatory sequence in a recombinant construct and used to transform soybean. The targeting sequence can be operably linked to a leghemoglobin sequence, such as occurs in SEQ ID NO: 31, or a sequence encoding SEQ ID NO: 32, and can be inserted through genome editing to replace all or part of the coding sequence of a seed storage protein such as glycinin or conglycinin, such that the native regulatory elements of the seed storage protein direct expression of the targeting sequence and the leghemoglobin coding sequence such that the leghemoglobin protein is expressed with a transit peptide and targeted to an intracellular compartment. The targeting sequence can be inserted into the native leghemoglobin gene, optionally with other insertions, or deletions or substitutions, so that leghemoglobin is expressed in the soybean seed from its native locus with a transit peptide and targeted to an intracellular compartment. In one embodiment the plastid targeting sequence is included at the N' terminus of the coding sequence or polypeptide of interest. One example of a plastid targeting sequence is the Rubisco SSUSP plastid targeting sequence, such as encoded by the nucleotide sequence from position 1 to position 165 of SEQ ID NO: 31, with the corresponding peptide targeting sequence at position 1 to position 55 of SEQ ID NO: 32. The leghemoglobin coding sequence is from position 166 to position 603 of SEQ ID NO: 31 and the corresponding peptide form position 56 to position 200 of SEQ ID NO: 32.

In some embodiments, soybean seeds are provided which express leghemoglobin from two or more sources, constructs or genomic locations, such as from two or more of (i) a recombinant construct inserted into the genome, (ii) a genome modification in which the leghemoglobin coding sequence replaces all or part of a seed storage protein coding sequence such as described herein (iii) a genome modification in which the native leghemoglobin gene is modified to include one or more of an insertion, deletion or substitution, such as into the regulatory region or coding sequence of the leghemoglobin gene and (iv) a plastid genome modification in which the plastid genome is modified to express a leghemoglobin coding sequence. In some embodiments, the two or more sources include at least one source in which the leghemoglobin coding sequence is operably linked to an intracellular targeting sequence, such as a plastid targeting sequence as described herein, and another source in which the leghemoglobin coding sequence is not operably linked to an intracellular targeting sequence.

In certain embodiments, the soybean seeds that comprise leghemoglobin and optionally other modifications as described herein can further comprise a modification to increase the amount of leghemoglobin complex in the soybean seed. The modification to increase leghemoglobin complex can include modified expression of one or more of a glutamyl-tRNA reductase, a glutamate-1-semialdehyde 2,1-aminomutase, an aminolevulinate dehydratase (HEMB1), a hydroxymethylbilane synthase (NEMC), a urophorphyrinogen III synthase, a urophorphyrinogen decarboxylase, a coporphyrinogen III oxidase (HEMF,CPOX), a protoporphyrinogen oxidase (PPOX), and/or a ferrochelatase. The modification can include the introduction of a recombinant construct into the genome of the plant, or the modification can include a gene editing modification, such as an insertion, deletion and/or substitution into the genes from which these polypeptides are expressed, such as to enhance transcription of the coding sequences of these genes.

In some embodiments, the soybean plants, cells and seeds comprise modifications in genes that encode regulatory proteins that modulate expression or activity of enzymes contributing to heme production or hemelation of leghemoglobin. For example, soybean genes encoding proteins that regulate glutamyl-tRNA reductase activity include glutamyl-tRNA reductase-binding protein (Glyma.08G222600), chloroplast signal particle 43(Glyma.11G097200) and FLUORESCENT IN BLUE LIGHT (Glyma.16G010200 and Glyma.07G041700) can be modified, such as by insertion, deletion or substitution to increase or enhance the formation of heme and/or the leghemoglobin complex in soybean.

In certain embodiments, the soybean seeds are edited to contain a leghemoglobin coding sequence inserted into a native gene encoding a seed storage protein and replacing in whole or in part the native seed storage coding sequence. Such an edited construct comprising an exogenous nucleic acid coding sequence operably linked to a native promoter in its native position in the genome would not be considered a recombinant construct, because the promoter and other regulatory elements are not exogenous to their native environment. For example, in an edited genome, the gene structure can remain largely unaltered, with the native seed-storage protein coding sequence being replaced by a different coding sequence, such as with a globulin protein, such as leghemoglobin. Such plants, seeds and cells may be referred to as modified or edited plants, seeds or cells.

One or more suitable seed storage protein coding sequences can be replaced with a globulin coding sequence using the methods described herein, such as a leghemoglobin coding sequence, including for example a sequence encoding a glycinin, conglycinin, 2S albumin, Kunitz trypsin inhibitor (KTI), a Bowman-Birk inhibitor (BBI), or a combination thereof.

The Kunitz trypsin inhibitor (KTI) and Bowman-Birk inhibitor (BBI) activity can be reduced to less than 50%, 40%, 30%, 20%, 10%, 9%, 8%, 7%, 6%, 5%, 4%, 3%, 2%, 1%, 0.5%, 0.4%, 0.3%, 0.2% or 0.1% of the activity found in a wild type, null or control soybean which has not had a modification to reduce or prevent expression of a Kunitz trypsin inhibitor (KTI) or Bowman-Birk inhibitor (BBI) coding sequence.

As used herein "encoding," "encoded," or the like, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolum* (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences disclosed herein may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98).

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, a percent similarity may be used. Sequences, which differ by such conservative substitutions, are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Provided are polynucleotide and polypeptide sequences which have at least or at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% and less than 100%, 99%, 95% or 90% identity to the polypeptides and polynucleotides of any one of SEQ ID NOs: 1-48, or to specified sequences within defined positions of any one of SEQ ID NOs: 1-48, such as disclosed herein.

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG® programs (Accelrys, Inc., San Diego, Calif.)). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65, and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

The leghemoglobin sequences and recombinant constructs described herein can be provided for expression in a plant of interest or an organism of interest. The cassette can include 5' and 3' regulatory sequences operably linked to a leghemoglobin polynucleotide or a modified leghemoglobin polynucleotide. "Operably linked" is intended to mean a functional linkage between two or more elements. For, example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked is intended that the coding regions are in the same reading frame. The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the modified glycinin polynucleotide to be under the transcriptional regulation of the regulatory regions. The expression cassette may additionally contain selectable marker genes.

The expression cassette can include in the 5'-3' direction of transcription, a transcriptional and translational initiation region (e.g., a promoter), a modified leghemoglobin polynucleotide described herein, and a transcriptional and translational termination region (e.g., termination region) functional in plants. The regulatory regions (e.g., promoters, transcriptional regulatory regions, and translational termination regions) and/or the modified leghemoglobin polynucleotide may be native/analogous to the host cell or to each other. Alternatively, the regulatory regions and/or the modified leghemoglobin polynucleotide may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, with the plant host, or may be derived from another source (i.e., foreign or heterologous) than the promoter, the modified glycinin polynucleotide, the plant host, or any combination thereof.

The expression cassette may additionally contain a 5' leader sequences. Such leader sequences can act to enhance translation. Translation leaders are known in the art and include viral translational leader sequences.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Certain types of promoters preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Also contemplated are synthetic promoters which include a combination of one or more heterologous regulatory elements.

The promoter can be any type or class of promoter known in the art, such that any one of a number of promoters can be used to express the various modified leghemoglobin sequences disclosed herein, including the native promoter of the polynucleotide sequence of interest. The promoters for use in the recombinant DNA constructs disclosed herein can be selected based on the desired outcome.

In certain embodiments, the recombinant DNA construct, described herein is expressed in a plant or seed. In certain embodiment, the plant or seed is a soybean plant or soybean seed. As used herein, the term "plant" includes plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

In certain embodiments, the soybean plants or soybean seeds further comprise at least one additional modification that increases the total protein in the seed as compared to a control seed (e.g., seed not comprising the at least one modification). In certain embodiments, the soybean seed comprising the at least one modification comprises at least about a 1%, 1.5%, 2%, 2.5%, 3%, 3.5%, 4%, 5%, 10%, or 15% and less than 20%, 15%, 10%, 9%, 8%, 7%, 6%, or 5% percentage point increase in total protein measured on a dry weight basis, as compared to a control seed.

In certain embodiments, the soybean plants or soybean seeds further comprise at least one additional modification decreasing the raffinose family oligosaccharides (RFO) content in the seed. In certain embodiments, the modification comprises a decrease in the expression and/or activity of a raffinose synthase. In certain embodiments, the modification comprises a decrease in the expression and/or activity of raffinose synthase 2 (RS2) and/or raffinose synthase 4 (RS4). In certain embodiments, the soybean seed comprises at least a 35%, 40%, 45%, 50%, 55%, 60%, 65%, 70%, 75%, 80%, 85%, 90%, 95%, or 99% decrease in expression of RS2, RS4, or RS2 and RS4, as compared to a control seed. In certain embodiments, the seed comprises less than about 6%, 5.5%, 5%, 4.5%, 4%, 3.5%, 3%, 2.5%, 2%, 1.5%, 1%, or 0.5% RFO content on a dry weight basis. In certain embodiments, the introduced modification decreases RFO content by at least about a 1%, 1.5%, 2%, 2.5%, 3%, 3.5%, 4%, 5%, 10%, or 15% and less than 20%, 15%, 10%, 9%, 8%, 7%, 6%, or 5% percentage point increase in total protein measured on a dry weight basis, as compared to a control seed.

In certain embodiments, the soybean plants or soybean seeds further comprise at least one additional modification that increases the amount of oleic acid in the seed, decreases the amount of linolenic acid in the seed, increases the amount of seed protein, or a combination thereof. For example, the modification can be in a FAD2-1A, FAD2-1B, FAD3a, FAD3b gene.

In certain embodiments, the soybean plants or soybean seeds further comprise at least one additional modification that increases the amount of total protein, for example by modification of one or more of a gene encoding (i) a CCT-domain containing protein, (ii) a reticulon, (iii) a trehalose phosphate synthase, (iv) a HECT Ubiquitin Ligase (HEL or UPL3), (v) a MFT (mother of flowering) polypeptide, (vi) a raffinose synthase RS2, RS3, or RS4, such as disclosed in U.S. Pat. Nos. 5,710,365, 8,728,726, and 10,081,814 each of which are incorporated herein by reference in their entirety or (vii) any combination thereof.

For example, provided are soybean seeds which comprise leghemoglobin in an amount disclosed herein and which can be processed to produce oils and meals, and the oils produced therefrom, which soybeans and/or oils have at least or at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 percent oleic (C 18:1) acid of the total fatty acids by weight and less than or less than about 100, 99, 98, 97, 96, 95, 94, 93, 92, 91, 90, 89, 88, 87, 86, 85, 84, 83, 82, 81, 80, 79, 78, 76, 75, 74, 73, 72, 71 or 70 percent oleic acid of the total fatty acids by weight.

For example, provided are soybean seeds which comprise leghemoglobin in an amount disclosed herein in an amount disclosed herein, which can be processed to produce oils, and the oils produced therefrom, which soybeans and/or oils have at least or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 percent linolenic (C 18:3) acid of the total fatty acids by weight and less than or less than about 6, 5.5, 5, 4.5, 4, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or 2.0 percent linolenic acid of the total fatty acids by weight.

For example, provided are soybean seeds which comprise leghemoglobin in an amount disclosed herein and which have a protein content of at least or at least about 35%, 36%, 37%, 38%, 39%, 40%, 41%, 42%, 43%, 44%, 45%, 46%, 47%, 48%, 49%, 50%, 51%, 52%, 53% 54% or 55% and less than or less than about 65%, 60%, 59%, 58%, 57%, 56%, 55%, 54%, 53%, 52%, 51% or 50% of the total seed weight when measured or adjusted to 13% moisture.

For example, provided are soybean seeds which comprise leghemoglobin in an amount disclosed herein and which have a stachyose content of less than or less than about 4%, 3.5%, 3%, 2.5%, 2%, 1.5%, 1%, 0.5%, 0.4%, 0.3%, 0.2%, or 0.1% and at least or at least about 0%, 0.01%, 0.05%, 0.06%, 0.07%, 0.08% or 0.09%, of the total seed weight when measured or adjusted to 13% moisture.

For example, provided are soybean seeds which comprise leghemoglobin in an amount disclosed herein and which have a raffinose content of less than or less than about 2%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% and at least or at least about 0%, 0.01%, 0.05%, 0.06%, 0.07%, 0.08% or 0.09% of the total seed weight when measured or adjusted to 13% moisture.

As used herein, "soy protein composition" refers to food ingredients for humans or animals which contain soy proteins. In certain embodiments, the composition is a human food composition. In certain embodiments, the human food composition is a composition selected from the group consisting of soybean meal; soyflour; defatted soyflour; soymilk; spray-dried soymilk; soy protein concentrate; texturized soy protein concentrate; hydrolyzed soy protein; soy protein isolate; spray-dried tofu; soy meat analog; soy cheese analog; and soy coffee creamer.

In some embodiments, a soybean isolate or soy protein isolate is provided which comprises at least 0.1%, 0.2%, 0.3%, 0.4%, 0.5%,1%, 2%, 3%, 4%, 5%, 6%, 7%, 8%, 9% or 10% and less than 25%, 20%, 15%, 10%, 9%, 8%, 7%, 6%, 5%, 4%, 3%, 2% or 1% leghemoglobin by weight of total protein, wherein at least about 25%, 30%, 35%, 40%, 45%, 50%, 55%, 60%, 65%, 70%, 80%, 85%, 90% or 95% and less than 99.9%, 99%, 98%, 97%, 96%, 95%, 90%, 85%, 80%, or 75% of the leghemoglobin is hemelated with an iron group.

In certain embodiments, plants producing seed comprising leghemoglobin as described herein comprise at least about a 10%, 15%, 20%, 25%, 30%, 35%, 40%, 50%, 60%, 70%, 80%, 90%, 100%, or 500% and less than about a 1000%, 500%, 100%, 90%, 80%, 70%, 60%, or 50% increase in the amount of one or more essential amino acids as compared to a control seed.

As used herein, "percent increase" refers to a change or difference expressed as a fraction of the control value, e.g. {[modified/transgenic/test value (%)−control value (%)]/control value (%)}×100%=percent change, or {[value obtained in a first location (%)−value obtained in second location (%)]/value in the second location (%)}×100=percent change.

In certain embodiments, the one or more essential amino acids is one or more of methionine, cystine, tryptophan, threonine, and lysine, or any combination thereof.

In certain embodiments, method, plants and seeds are provided which further comprise at least one additional modification increasing the total protein in the seed as compared to a control seed (e.g., seed not comprising the at least one modification). In certain embodiments, the introduced modification increases the protein content in the soybean seed comprising leghemoglobin to at least about a 1%, 1.5%, 2%, 2.5%, 3%, 3.5%, 4%, 5%, 10%, or 15% and less than 20%, 15%, 10%, 9%, 8%, 7%, 6%, or 5% percentage point increase in total protein measured on a dry weight basis, as compared to a control seed.

In certain embodiments, the method further comprises introducing at least one modification decreasing the raffinose family oligosaccharides (RFO) content in the seed. In certain embodiments, the modification comprises a decrease in the expression and/or activity of a raffinose synthase. In certain embodiments, the modification comprises a decrease in the expression and/or activity of raffinose synthase 2 (RS2) and/or raffinose synthase 4 (RS4). In certain embodiments, the soybean seed comprises at least a 35%, 40%, 45%, 50%, 55%, 60%, 65%, 70%, 75%, 80%, 85%, 90%, 95%, or 99% decrease in expression of RS2, RS4, or RS2 and RS4, as compared to a control seed. In certain embodiments, the seed comprises less than about 6%, 5.5%, 5%, 4.5%, 4%, 3.5%, 3%, 2.5%, 2%, 1.5%, 1%, or 0.5% RFO content on a dry weight basis. In certain embodiments, the introduced modification decreases RFO content by at least about a 1%, 1.5%, 2%, 2.5%, 3%, 3.5%, 4%, 5%, 10%, or 15% and less than 20%, 15%, 10%, 9%, 8%, 7%, 6%, or 5% percentage point increase in total protein measured on a dry weight basis, as compared to a control seed In certain embodiments, the method comprises: (a) providing a guide RNA, at least one polynucleotide modification template, and at least one Cas endonuclease to a plant cell, wherein the at least one Cas endonuclease introduces a double stranded break at an endogenous gene to be modified in the plant cell, and wherein the polynucleotide modification template generates a modified gene that encodes any of the polypeptides described herein; (b) obtaining a plant from the plant cell; and (c) generating a progeny plant.

Methods and compositions are provided herein for modifying naturally-occurring polynucleotides or integrated transgenic sequences, including regulatory elements, coding sequences, and non-coding sequences. These methods and compositions are also useful in targeting nucleic acids to pre-engineered target recognition sequences in the genome. Modification of polynucleotides may be accomplished, for example, by introducing single- or double-strand breaks into the DNA molecule.

In certain embodiments, the method comprises: (a) providing a guide RNA, at least one polynucleotide modification template, and at least one Cas endonuclease to a plant cell, wherein the at least one Cas endonuclease introduces a double stranded break at an endogenous gene to be modified in the plant cell, and wherein the polynucleotide modification template generates a modified gene that encodes any of the polypeptides described herein; (b) obtaining a plant from the plant cell; and (c) generating a progeny plant.

Double-strand breaks induced by double-strand-break-inducing agents, such as endonucleases that cleave the phosphodiester bond within a polynucleotide chain, can result in the induction of DNA repair mechanisms, including the non-homologous end-joining pathway, and homologous recombination. Endonucleases include a range of different enzymes, including restriction endonucleases (see e.g. Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.)), meganucleases (see e.g., WO 2009/114321; Gao et al. (2010) Plant Journal 1:176-187), TAL effector nucleases or TALENs (see e.g., US20110145940, Christian, M., T. Cermak, et al. 2010. Targeting DNA double-strand breaks with TAL effector nucleases. Genetics 186(2): 757-61 and Boch et al., (2009), Science 326(5959): 1509-12), zinc finger nucleases (see e.g. Kim, Y. G., J. Cha, et al. (1996). "Hybrid restriction enzymes: zinc finger fusions to Fokl cleavage"), and CRISPR-Cas endonucleases (see e.g. WO2007/025097 application published Mar. 1, 2007).

Once a double-strand break is induced in the genome, cellular DNA repair mechanisms are activated to repair the break. There are two DNA repair pathways. One is termed nonhomologous end-joining (NHEJ) pathway (Bleuyard et al., (2006) DNA Repair 5:1-12) and the other is homology-directed repair (HDR). The structural integrity of chromosomes is typically preserved by NHEJ, but deletions, insertions, or other rearrangements (such as chromosomal translocations) are possible (Siebert and Puchta, 2002, Plant Cell 14:1121-31; Pacher et al., 2007, Genetics 175:21-9. The HDR pathway is another cellular mechanism to repair double-stranded DNA breaks and includes homologous recombination (HR) and single-strand annealing (SSA) (Lieber. 2010 Annu. Rev. Biochem. 79:181-211).

In addition to the double-strand break inducing agents, site-specific base conversions can also be achieved to engineer one or more nucleotide changes to create one or more modifications described herein into the genome. These include for example, a site-specific base edit mediated by an C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016): 420-4.

In the methods described herein, the endogenous gene may be modified by a CRISPR associated (Cas) endonuclease, a Zn-finger nuclease-mediated system, a meganuclease-mediated system, an oligonucleobase-mediated system, or any gene modification system known to one of ordinary skill in the art.

In certain embodiments the endogenous gene is modified by a CRISPR associated (Cas) endonuclease.

Class I Cas endonucleases comprise multisubunit effector complexes (Types I, III, and IV), while Class 2 systems comprise single protein effectors (Types II, V, and VI) (Makarova et al. 2015, Nature Reviews Microbiology Vol. 13:1-15; Zetsche et al., 2015, Cell 163, 1-13; Shmakov et al., 2015, Molecular Cell 60, 1-13; Haft et al., 2005, Computational Biology, PLoS Comput Biol 1(6): e60; and Koonin et al. 2017, Curr Opinion Microbiology 37:67-78). In Class 2 Type II systems, the Cas endonuclease acts in complex with a guide polynucleotide.

Accordingly, in certain embodiments of the methods described herein the Cas endonuclease forms a complex with a guide polynucleotide (e.g., guide polynucleotide/Cas endonuclease complex).

As used herein, the term "guide polynucleotide", relates to a polynucleotide sequence that can form a complex with a Cas endonuclease, including the Cas endonucleases described herein, and enables the Cas endonuclease to recognize, optionally bind to, and optionally cleave a DNA target site. The guide polynucleotide sequence can be a RNA sequence, a DNA sequence, or a combination thereof (a RNA-DNA combination sequence). The guide polynucleotide may further comprise a chemically-modified base, such as, but not limited, to Locked Nucleic Acid (LNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization.

In certain embodiments, the Cas endonuclease forms a complex with a guide polynucleotide (e.g., gRNA) that directs the Cas endonuclease to cleave the DNA target to enable target recognition, binding, and cleavage by the Cas endonuclease. The guide polynucleotide (e.g., gRNA) may comprise a Cas endonuclease recognition (CER) domain that interacts with the Cas endonuclease, and a Variable Targeting (VT) domain that hybridizes to a nucleotide sequence in a target DNA. In certain embodiments, the guide polynucleotide (e.g., gRNA) comprises a CRISPR nucleotide (crNucleotide; e.g., crRNA) and a trans-activating CRISPR nucleotide (tracrNucleotide; e.g., tracrRNA) to guide the Cas endonuclease to its DNA target. The guide polynucleotide (e.g., gRNA) comprises a spacer region complementary to one strand of the double strand DNA target and a region that base pairs with the tracrNucleotide (e.g., tracrRNA), forming a nucleotide duplex (e.g. RNA duplex).

In certain embodiments, the gRNA is a "single guide RNA" (sgRNA) that comprises a synthetic fusion of crRNA and tracrRNA. In many systems, the Cas endonuclease-guide polynucleotide complex recognizes a short nucleotide sequence adjacent to the target sequence (protospacer), called a "protospacer adjacent motif" (PAM).

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, optionally bind to, and optionally nick or cleave (introduce a single or double-strand break) the DNA target site.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In one embodiment, the nucleotide sequence linking the crNucleotide and the tracrNucleotide of a single guide polynucleotide can comprise a tetraloop sequence, such as, but not limiting to a GAAA tetraloop sequence.

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a (trans-acting) tracrNucleotide mate sequence followed by a tracrNucleotide sequence. The CER domain can be composed of a DNA sequence, a RNA sequence, a modified DNA sequence, a modified RNA sequence (see for example US20150059010A1, published 26 Feb. 2015), or any combination thereof.

A "protospacer adjacent motif" (PAM) as used herein refers to a short nucleotide sequence adjacent to a target sequence (protospacer) that is recognized (targeted) by a guide polynucleotide/Cas endonuclease system described herein. In certain embodiments, the Cas endonuclease may not successfully recognize a target DNA sequence if the target DNA sequence is not adjacent to, or near, a PAM sequence. In certain embodiments, the PAM precedes the target sequence (e.g. Cas12a). In certain embodiments, the PAM follows the target sequence (e.g. *S. pyogenes* Cas9). The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "polynucleotide-guided endonuclease", and "PGEN" are used interchangeably herein and refer to at least one guide polynucleotide and at least one Cas endonuclease, that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s) and suitable polynucleotide component(s) of any of the known CRISPR systems (Horvath and Barrangou, 2010, Science 327:167-170; Makarova et al. 2015, Nature Reviews Microbiology Vol. 13:1-15; Zetsche et al., 2015, Cell 163, 1-13; Shmakov et al., 2015, Molecular Cell 60, 1-13). In certain embodiments, the guide polynucleotide/Cas endonuclease complex is provided as a ribonucleoprotein (RNP), wherein the Cas endonuclease component is provided as a protein and the guide polynucleotide component is provided as a ribonucleotide.

Examples of Cas endonucleases for use in the methods described herein include, but are not limited to, Cas9 and Cpf1. Cas9 (formerly referred to as Cas5, Csn1, or Csx12) is a Class 2 Type II Cas endonuclease (Makarova et al. 2015, Nature Reviews Microbiology Vol. 13:1-15). A Cas9-gRNA complex recognizes a 3' PAM sequence (NGG for the *S. pyogenes* Cas9) at the target site, permitting the spacer of the guide RNA to invade the double-stranded DNA target, and, if sufficient homology between the spacer and protospacer exists, generate a double-strand break cleavage. Cas9 endonucleases comprise RuvC and HNH domains that together produce double strand breaks, and separately can produce single strand breaks. For the *S. pyogenes* Cas9 endonuclease, the double-strand break leaves a blunt end. Cpf1 is a Clas 2 Type V Cas endonuclease, and comprises nuclease RuvC domain but lacks an HNH domain (Yamane et al., 2016, Cell 165:949-962). Cpf1 endonucleases create "sticky" overhang ends.

Some uses for Cas9-gRNA systems at a genomic target site include, but are not limited to, insertions, deletions, substitutions, or modifications of one or more nucleotides at the target site; modifying or replacing nucleotide sequences of interest (such as a regulatory elements); insertion of polynucleotides of interest; gene knock-out; gene-knock in; modification of splicing sites and/or introducing alternate splicing sites; modifications of nucleotide sequences encoding a protein of interest; amino acid and/or protein fusions; and gene silencing by expressing an inverted repeat into a gene of interest.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, a locus, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell. An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

A "polynucleotide modification template" is also provided that comprises at least one nucleotide modification when compared to the nucleotide sequence to be edited. For example, a modification in the endogenous gene corresponding to SEQ ID NO: 1 to induce an amino substitution in the encoded polypeptide. A nucleotide modification can be at least one nucleotide substitution, addition, deletion, or chemical alteration. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In certain embodiments of the methods disclosed herein, a polynucleotide of interest is inserted at a target site and provided as part of a "donor DNA" molecule. As used herein, "donor DNA" is a DNA construct that comprises a polynucleotide of interest to be inserted into the target site of a Cas endonuclease. The donor DNA construct further comprises a first and a second region of homology that flank the polynucleotide of interest. The first and second regions of homology of the donor DNA share homology to a first and a second genomic region, respectively, present in or flanking the target site of the cell or organism genome. The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, Nature Methods Vol. 10: 957-963). The amount of homology or sequence identity shared by a target and a donor polynucleotide can vary and includes total lengths and/or regions.

The process for editing a genomic sequence at a Cas9-gRNA double-strand-break site with a modification template generally comprises: providing a host cell with a Cas9-gRNA complex that recognizes a target sequence in the genome of the host cell and is able to induce a double-strand-break in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the double-strand break. Genome editing using double-strand-break-inducing agents, such as Cas9-gRNA complexes, has been described, for example in US20150082478 published on 19 Mar. 2015, WO2015026886 published on 26 Feb. 2015, WO2016007347 published 14 Jan. 2016, and WO2016025131 published on 18 Feb. 2016.

To facilitate optimal expression and nuclear localization for eukaryotic cells, the gene comprising the Cas endonuclease may be optimized as described in WO2016186953 published 24 Nov. 2016, and then delivered into cells as DNA expression cassettes by methods known in the art. In certain embodiments, the Cas endonuclease is provided as a polypeptide. In certain embodiments, the Cas endonuclease is provided as a polynucleotide encoding a polypeptide. In certain embodiments, the guide RNA is provided as a DNA molecule encoding one or more RNA molecules. In certain embodiments, the guide RNA is provided as RNA or chemically-modified RNA. In certain embodiments, the Cas endonuclease protein and guide RNA are provided as a ribonucleoprotein complex (RNP).

In certain embodiments, methods for modifying the endogenous by a zinc-finger-mediated genome editing process are provided. The zinc-finger-mediated genome editing process for editing a chromosomal sequence includes for example: (a) introducing into a cell at least one nucleic acid encoding a zinc finger nuclease that recognizes a target sequence in the chromosomal sequence and is able to cleave a site in the chromosomal sequence, and, optionally, (i) at least one donor polynucleotide that includes a sequence for integration flanked by an upstream sequence and a downstream sequence that exhibit substantial sequence identity with either side of the cleavage site, or (ii) at least one exchange polynucleotide comprising a sequence that is substantially identical to a portion of the chromosomal sequence at the cleavage site and which further comprises at least one nucleotide change; and (b) culturing the cell to allow expression of the zinc finger nuclease such that the zinc finger nuclease introduces a double-stranded break into the chromosomal sequence, and wherein the double-stranded break is repaired by (i) a non-homologous end-joining repair process such that an inactivating mutation is introduced into the chromosomal sequence, or (ii) a homology-directed repair process such that the sequence in the donor polynucleotide is integrated into the chromosomal sequence or the sequence in the exchange polynucleotide is exchanged with the portion of the chromosomal sequence.

A zinc finger nuclease includes a DNA binding domain (i.e., zinc finger) and a cleavage domain (i.e., nuclease). The nucleic acid encoding a zinc finger nuclease may include DNA or RNA. Zinc finger binding domains may be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Choo et al. (2000) Curr. Opin. Struct. Biol. 10:411-416; and Doyon et al. (2008) Nat. Biotechnol. 26:702-708; Santiago et al. (2008) Proc. Natl. Acad. Sci. USA 105:5809-5814; Urnov, et al., (2010) Nat Rev Genet. 11(9):636-46; and Shukla, et al., (2009) Nature 459 (7245): 437-41. An engineered zinc finger binding domain may have a novel binding specificity compared to a naturally-occurring zinc finger protein. As an example, the algorithm of described in U.S. Pat. No. 6,453,242 may be used to design a zinc finger binding domain to target a preselected sequence. Nondegenerate recognition code tables may also be used to design a zinc finger binding domain to target a specific sequence (Sera et al. (2002) Biochemistry 41:7074-7081). Tools for identifying potential target sites in DNA sequences and designing zinc finger binding domains may be used (Mandell et al. (2006) Nuc. Acid Res. 34:W516-W523; Sander et al. (2007) Nuc. Acid Res. 35:W599-W605).

An exemplary zinc finger DNA binding domain recognizes and binds a sequence having at least about 80% sequence identity with the desired target sequence. In other embodiments, the sequence identity may be about 81%, 82%, 83%, 84%, 85%, 86%, 87%, 88%, 89%, 90%, 91%, 92%, 93%, 94%, 95%, 96%, 97%, 98%, 99%, or 100%.

A zinc finger nuclease also includes a cleavage domain. The cleavage domain portion of the zinc finger nucleases may be obtained from any endonuclease or exonuclease. Non-limiting examples of endonucleases from which a cleavage domain may be derived include, but are not limited to, restriction endonucleases and homing endonucleases. See, for example, 2010-2011 Catalog, New England Biolabs, Beverly, Mass.; and Belfort et al. (1997) Nucleic Acids Res. 25:3379-3388. Additional enzymes that cleave DNA are known (e.g., 51 Nuclease; mung bean nuclease; pancreatic DNase I; micrococcal nuclease; yeast HO endonuclease). One or more of these enzymes (or functional fragments thereof) may be used as a source of cleavage domains.

In certain embodiments of the methods described herein the endogenous gene is modified by using "custom" meganucleases produced to modify plant genomes (see e.g., WO 2009/114321; Gao et al. (2010) Plant Journal 1:176-187). The term "meganuclease" generally refers to a naturally-occurring homing endonuclease that binds double-stranded DNA at a recognition sequence that is greater than 12 base pairs and encompasses the corresponding intron insertion site. Naturally-occurring meganucleases can be monomeric (e.g., I-SceI) or dimeric (e.g., I-CreI). The term meganuclease, as used herein, can be used to refer to monomeric meganucleases, dimeric meganucleases, or to the monomers which associate to form a dimeric meganuclease.

Naturally-occurring meganucleases, for example, from the LAGLIDADG family, have been used to effectively promote site-specific genome modification in plants, yeast, *Drosophila*, mammalian cells and mice. Engineered meganucleases such as, for example, LIG-34 meganucleases, which recognize and cut a 22 basepair DNA sequence found in the genome of *Zea mays* (maize) are known (see e.g., US 20110113509).

In certain embodiments of the methods described herein the endogenous gene is modified by using TAL endonucleases (TALEN). TAL (transcription activator-like) effectors from plant pathogenic *Xanthomonas* are important virulence factors that act as transcriptional activators in the plant cell nucleus, where they directly bind to DNA via a central domain of tandem repeats. A transcription activator-like (TAL) effector-DNA modifying enzymes (TALE or TALEN) are also used to engineer genetic changes. See e.g., US20110145940, Boch et al., (2009), Science 326(5959): 1509-12. Fusions of TAL effectors to the Fokl nuclease provide TALENs that bind and cleave DNA at specific locations. Target specificity is determined by developing customized amino acid repeats in the TAL effectors.

In certain embodiments of the methods described herein the endogenous gene is modified by using base editing, such as an oligonucleobase-mediated system. In addition to the double-strand break inducing agents, site-specific base conversions can also be achieved to engineer one or more nucleotide changes to create one or more EMEs described herein into the genome. These include for example, a site-specific base edit mediated by a C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA.

Further provided are methods of plant breeding comprising crossing any of the soybean plants described herein with a second plant to produce a progeny seed comprising at least one modification described herein. In certain embodiments, a plant is produced from the progeny seed.

The following are examples of specific embodiments of some aspects of the invention. The examples are offered for illustrative purposes only and are not intended to limit the scope of the invention in any way.

Example 1: Expression of Soybean Leghemoglobin Protein in Soybean Seeds

Figure 1:
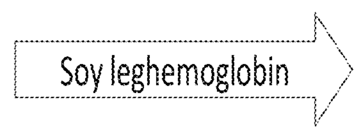
FIG. 1 is a chart showing construct design for the expression of soybean leghemoglobin with or without different protein targeting sequences
Figure 1:
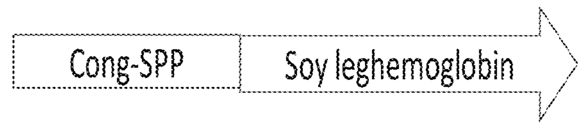
Figure 1:
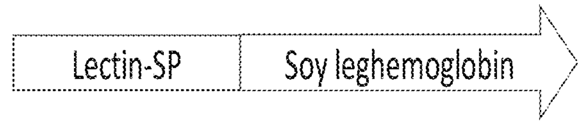
Figure 1:
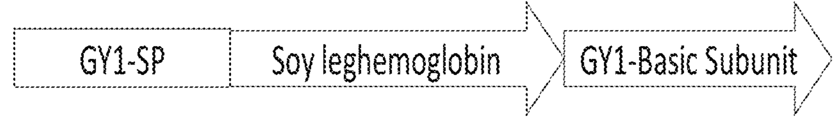

A soybean leghemoglobin gene (Glyma.20g191200) was identified in the soybean genome. The gene contains 4 exons, with its CDS (SEQ ID NO: 1) encoding a leghemoglobin peptide (SEQ ID NO: 2). As shown in FIG. 1, the soybean leghemoglobin was expressed with no signal peptide in soybean seeds. In addition, several protein targeting signal sequences were used to target the leghemoglobin into protein storage vacuole in soybean seeds (Table 2). The beta-conglycinin alpha' SPP is encoded by the nucleotides from position 1 to position 195 of SEQ ID NO: 3, with its corresponding peptide sequences defined by position 1 to position 65 of SEQ ID NO: 4. The lectin SP is encoded by the nucleotides from position 1 to position 105 of SEQ ID NO: 5, with its corresponding peptide sequence defined by position 1 to position 35 of SEQ ID NO: 6. The GY1 SP is encoded by the nucleotides from position 1 to position 66 of SEQ ID NO: 7, with its corresponding peptide sequence defined by position 1 to position 22 of SEQ ID NO: 8. A strong seed specific promoter, such as a beta-conglycinin promoter (SEQ ID NO: 9) or a glycinin promoter (SEQ ID NO: 10) was used to drive the expression of the leghemoglobin. The Rubisco small subunit (Rubisco SSU) plastid targeting sequences were also used to target the leghemoglobin protein to plastids. The Rubisco SSUSP plastid targeting sequence is encoded by the nucleotide sequence from position 1 to position 165 of SEQ ID NO: 31, with the corresponding peptide targeting sequence at position 1 to position 55 of SEQ ID NO: 32. The leghemoglobin coding sequence is from position 166 to position 603 of SEQ ID NO: 31 and the corresponding peptide form position 56 to position 200 of SEQ ID NO: 32. These expression vectors were introduced into soybean plants by Ochrobactrum-mediated or Agrobacteria-mediated soybean embryonic axis transformation, the former being described in US Patent Publication No. 2018/0216123. The results are described in Example 7.

TABLE 2

Expression of Leghemoglobin by Protein Targeting in Soybean Seeds.

| Leghemoglobin (LH) with or without Signal Peptide (Vector name) | Nucleotide SEQ ID NOs: | Peptide SEQ ID NOs: |
|---|---|---|
| No signal peptide::LH | SEQ ID NO: 1 | SEQ ID NO: 2 |
| Beta-conglycinin alpha' SPP::LH | SEQ ID NO: 3 | SEQ ID NO: 4 |
| Lectin SP::LH | SEQ ID NO: 5 | SEQ ID NO: 6 |
| GY1 SP::LH::GY1-Basic subunit | SEQ ID NO: 7 | SEQ ID NO: 8 |
| Rubisco SSUSP::LH | SEQ ID NO: 31 | SEQ ID NO: 32 |

Figure 2:
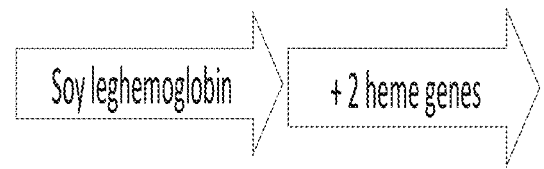
FIG. 2 is a chart showing construct design for the improvement of soybean leghemoglobin expression level by porphyrin pathway engineering.
Figure 2:
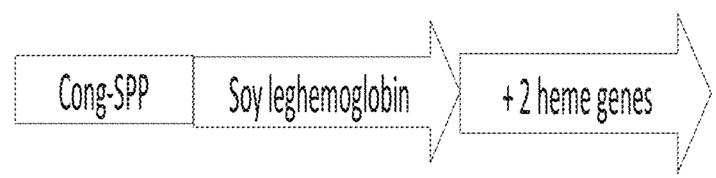
Figure 2:
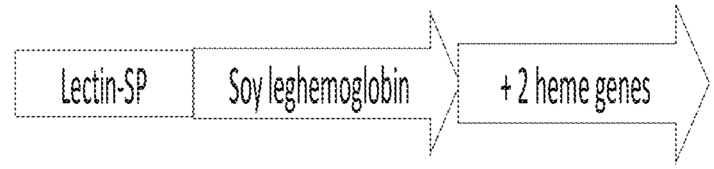
Figure 2:
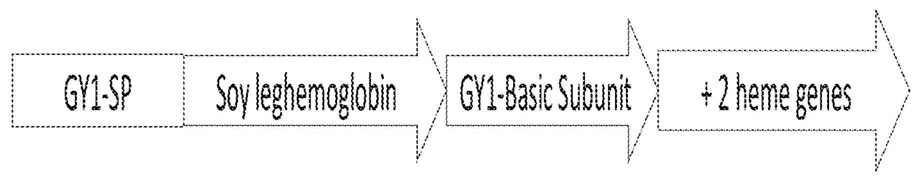

Example 2: Improvement of Soybean Leghemoglobin Expression Level by Porphyrin Pathway Engineering—Glutamyl-tRNA Reductase and Ferrochelatase To improve the soybean leghemoglobin expression level in seeds, a porphyrin pathway engineering approach was employed. There are at least nine enzymatic steps for the porphyrin pathway leading to the heme biosynthesis. Among them, as shown in FIG. 2, the glutamyl-tRNA reductase (glyma.04g089800) and ferrochelatase (glyma.04g050400) were tested for increasing heme production, to facilitate higher leghemoglobin accumulation and heme loading in soybean seeds. For this purpose, four additional soybean vectors were made, each of them contained the expression of glutamyl-tRNA reductase (SEQ ID NO: 11, 12) and ferrochelatase (SEQ ID NOs: 13, 14), in addition to the leghemoglobin expression cassettes in Example 1. The two biosynthetic genes were driven by strong seed specific promoters, such as *Phaseolus vulgaris* Phaseolin promoter (SEQ ID NO: 15) or *Brassica napus* Napin Promoter (SEQ ID NO: 16). In these four vectors, the expression cassettes of these two biosynthetic genes were stacked molecularly with the four expression cassettes of the leghemoglobin with or without different signal peptide targeting sequences. These expression vectors were introduced into soybean plants by Ochrobactrum-mediated soybean embryonic axis transformation as described in US Patent Publication No. 2018/0216123. The results are described in Example 7.

Example 3: Improvement of Soybean Leghemoglobin Expression Level by Porphyrin Enzyme Modifications or Expression A similar technical approach to the methods described in Example 2 is used to regulate other enzymatic steps for the porphyrin pathway, such as glutamate-1-semialdehyde 2, 1-aminomutase, aminolevulinate dehydratase, hydroxymethylbilane synthase, urophorphyrinogen III synthase, urophorphyrinogen decarboxylase, coporphyrinogen III oxidase, and protoporphyrinogen oxidase. Examples of soybean genes for the porphyrin pathway that are used are listed in Table 3. Overexpressing these native metabolic enzyme genes in soybean seeds is achieved by transformation of soybean with a recombinant construct comprising a coding sequence for these polypeptides, operably linked to regulatory sequences that provide for expression in soybean seeds. Secondly, increased expression of these enzymes is achieved through gene editing. Feedback sensitive regulatory domains of these enzymes are identified and removed or inactivated by gene editing truncations, deletions, substitutions or insertions. It is expected that enhanced heme content of the leghemoglobin protein produced in soybean seeds modified to produce increased leghemoglobin protein complex is achieved. The heme biosynthetic enzymes which are modified to be feedback-insensitive or are otherwise modified or edited to enhance enzyme expression, stability or activity are expressed in soybean seeds to further increase heme production, enabling higher leghemoglobin accumulation and heme loading in soybean seeds. Specifically, Glutamyl-tRNA reductase (GTR) enzyme activity is under combinatorial, post-translational control mediated by the proteins FLUORESCENT IN BLUE LIGHT (FLU), Glutamyl-tRNA reductase-binding protein (GBP), chloroplast signal particle 43 (SRP43) (Table 4). Altered expression of a single or any combination of these three proteins achieved by gene editing, seed-preferred over-expression or RNA interference is expected to achieve higher level of heme-containing leghemoglobin by increasing heme-biosynthetic activity in developing seeds.

TABLE 3

The soybean genes in the porphyrin pathway

| Enzyme name | Gene Model Name |
|---|---|
| Glutamyl-tRNA reductase | Glyma.02G218300 |
| | Glyma.04G089800 |
| | Glyma.06G091600 |
| | Glyma.07G184700 |
| | Glyma.08G064700 |
| | Glyma.14G185700 |
| glutamate-1-semialdehyde 2,1-aminomutase | Glyma.04G002900 |
| | Glyma.06G002900 |
| | Glyma.14G221900 |
| aminolevulinate dehydratase (HEMB1) | Glyma.04G247700 |
| | Glyma.06G115000 |
| hydroxymethylbilane synthase (HEMC) | Glyma.01G227400 |
| | Glyma.11G015400 |
| | Glyma.11G094700 |
| | Glyma.12G021100 |

TABLE 3-continued

The soybean genes in the porphyrin pathway

| Enzyme name | Gene Model Name |
|---|---|
| urophorphyrinogen III synthase | Glyma.04G037000 |
| | Glyma.06G037300 |
| urophorphyrinogen decarboxylase | Glyma.11G235400 |
| | Glyma.12G229700 |
| | Glyma.13G269900 |
| | Glyma.18G021500 |
| coporphyrinogen III oxidase (HEMF, CPOX) | Glyma.14G003200 |
| protoporphyrinogen oxidase (PPOX) | Glyma.10G138600 |
| | Glyma.02G007200 |
| | Glyma.19G245900 |
| | Glyma.08G173600 |
| ferrochelatase | Glyma.04G050400 |
| | Glyma.04G205600 |
| | Glyma.05G197600 |
| | Glyma.06G051100 |
| | Glyma.06G159900 |
| | Glyma.08G005000 |

TABLE 4

The soybean genes encoding proteins that regulate Glutamyl-tRNA reductase activity

| Enzyme name | Gene Model Name |
|---|---|
| Glutamyl-tRNA reductase-binding protein | Glyma.08G222600 |
| chloroplast signal particle 43 | Glyma.11G097200 |
| FLUORESCENT IN BLUE LIGHT | Glyma.16G010200 |
| | Glyma.07G041700 |

Figure 3:
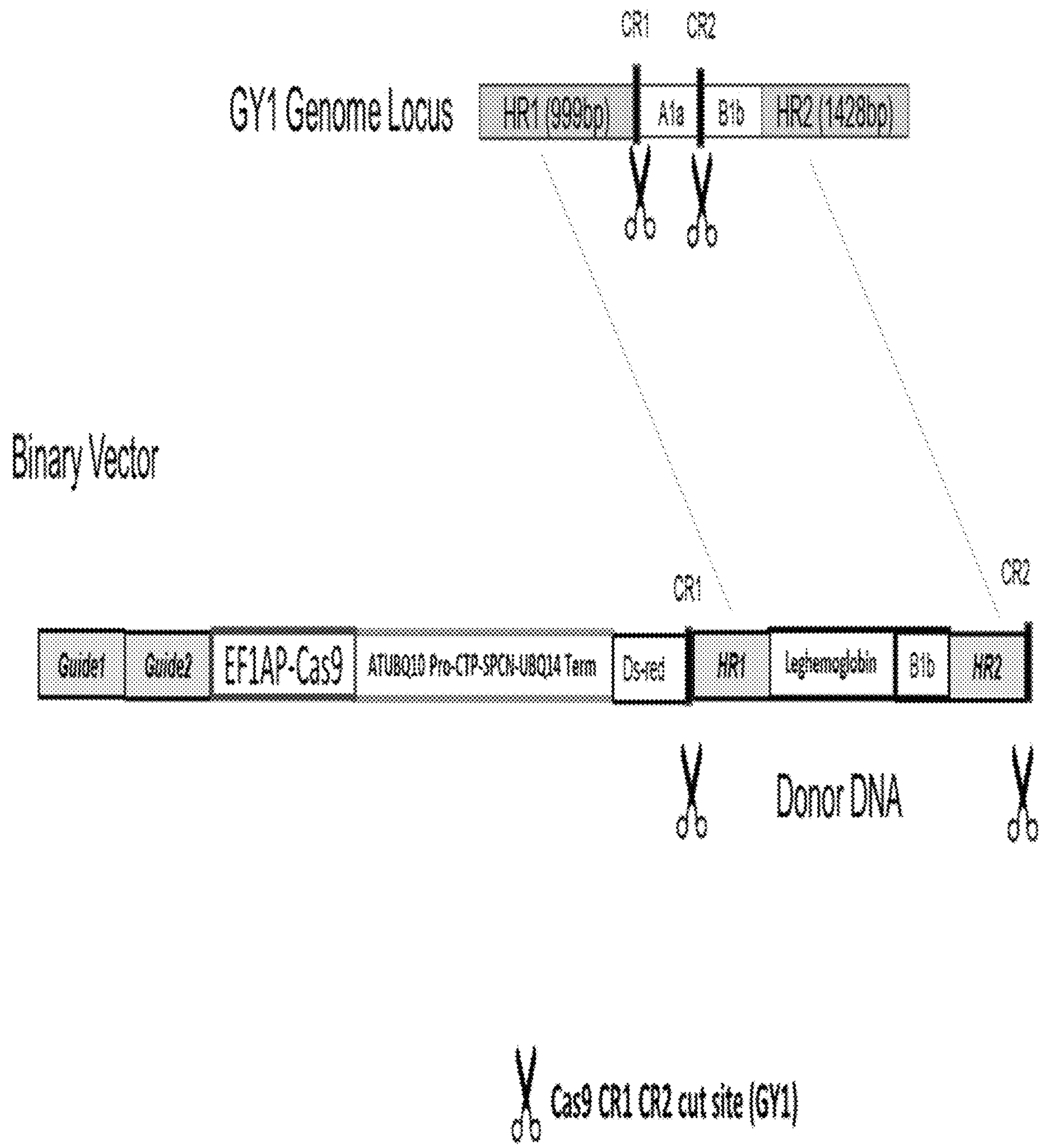
FIG. 3 is a schematic showing genome engineering of the leghemoglobin gene into the native soybean glycinin gene locus by CR1/CR2 gRNA pair.
Figure 4:
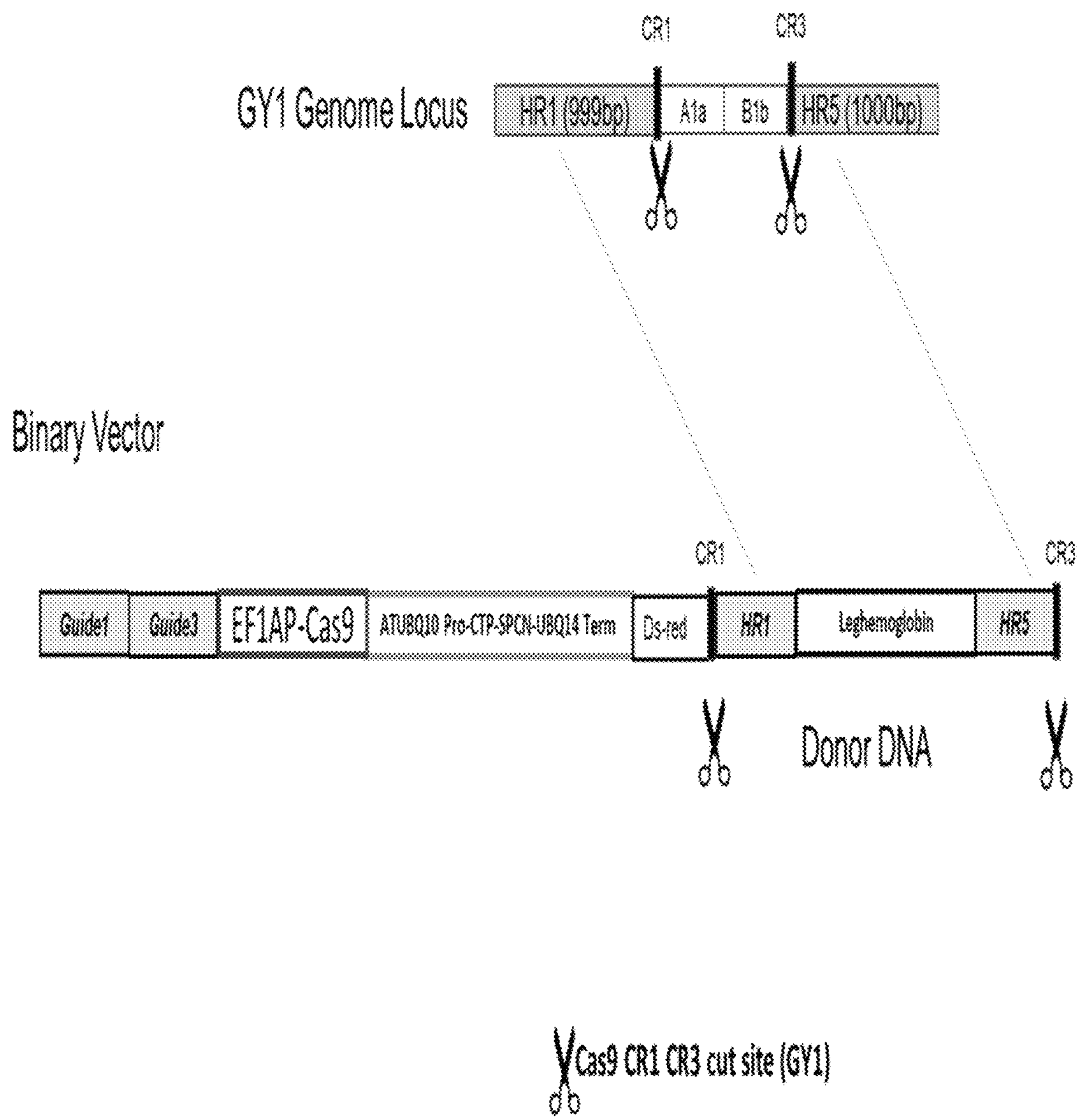
FIG. 4 is a schematic showing genome engineering of the leghemoglobin gene into the native soybean glycinin gene locus by CR1/CR3 gRNA pair

Example 4: Genome Engineering of the Leghemoglobin Gene into the Native Soybean Glycinin Gene Loci With the CRISPR/Cas9 system, we designed specific gRNAs (GM-GY-CR1, SEQ ID NO: 17; GM-GY-CR2, SEQ ID NO: 18; and GM-GY-CR3, SEQ ID NO: 19) to target the Glycinin 1 (GY1) gene (glyma.03g163500, SEQ ID NO: 20 for nucleotide sequences, SEQ ID NO:21 for peptide sequences). The GM-GY1-CR1 was designed to target a site near the beginning of the exon1 of the pro-glycinin 1 protein. The GM-GY1-CR2 was designed to target the junction between the acidic subunit (amino acid #1 to #310 in SEQ ID NO: 21) and basic subunit (amino acid #311 to #495 in SEQ ID NO: 21) of the pro-glycinin1. The GM-GY1-CR3 was designed to target the beginning of the 3' UTR of glycinin 1 gene. As shown in FIGS. 3 and 4, the binary vectors contained either CR1/CR2 or CR1/CR3 gRNA combinations and their corresponding donor DNA templates (SEQ ID NO: 22 and SEQ ID NO: 23). The homology recombination (HR) fragments were used to flank the leghemoglobin/GY1 sequences to facilitate the homology-mediated recombination process. The CR1 or CR2 or CR3 gRNA target sites were also used to flank the donor DNAs to enable them to be excised from the binary vectors for double strand break repair process. These sequences are defined in Table 5.

TABLE 5

| The nucleotide sequences of HR fragments and CR Cut sites in donor DNA templates | |
|---|---|
| | Location in SEQ ID NOs |
| HR1 | Position 34 to position 1032 of SEQ ID NO: 22 and of SEQ ID NO: 23 |
| HR2 | Position 2104 to position 3531 of SEQ ID NO: 22 |
| HR5 | Position 2108 to position 3531 of SEQ ID NO: 23 |
| CR1 Cut Site | Position 1 to position 22 of SEQ ID NO: 22 and of SEQ ID NO: 23 |
| CR2 Cut Site | Position 3543 to position 3565 of SEQ ID NO: 22 |
| CR3 Cut site | Position 3543 to position 3565 of SEQ ID NO: 23 |

The binary vectors were introduced into soybean plants by *Agrobacterium*-mediated soybean embryonic axis transformation. With site-specific integration of the donor DNA by homology-mediated double strand break DNA repair process, a genome editing variants of the glycinin 1 with the soybean leghemoglobin were created by (i) replacing the genomic sequences encoding the acidic subunit at the native Glycinin 1 gene locus or (ii) replacing the genomic sequences encoding the entire glycinin1 protein at the native Glycinin 1 gene locus. In total, 1452 T0 plants were generated for the CR1/CR3 design (FIG. 3) to replace the entire glycinin1 gene with the leghemoglobin coding sequences at the native glycinin1 gene locus. We used two PCR analyses to identify the perfect gene integration events, one is at the 5' and another at the 3' region of the glycinin1 locus. For the 1452 T0 plants, 10 potential 2×HDR perfect integration events were identified at T0 plants. Based on the intensity of the PCR products, we classified them into three categories: strong (4 events), medium (3 events) and weak (3 events). Of these 10 events, we performed sequencing analysis of the PCR products, two of the 10 events (1 strong and 1 weak event) had SNP variations from double strand break repair process, so we did not proceed with those two events further. T1 seeds were harvest from all remaining 8 positive events. We proceeded with leghemoglobin quantification of the T1 seeds from our top six events based on our T0 plant analyses (3 strong events: 198A, 315A, 956A and 3 medium events: 407A, 419A and 628A), the 315A events gave the highest globin accumulation (1.16% of the total protein of the seed; dry weight basis) in T1 seeds.

TABLE 5A

Quantitative Mass Spectrometry analysis of single wildtype (yellow) and red soybeans harvested from segregating T0 plants expressing the LegHemoglobin construct targeted to the GY1 Locus

| SAMPLE ID | Soluble protein/total Protein (wt %) | LegHemoglobin protein/soluble protein (wt %) | LegHemoglobin protein/total protein (wt %) |
|---|---|---|---|
| GV.GM7MDH.005.198)X (yellow) | 70.69 | 0.00 | 0.00 |
| GV.GM7MDH.005.198)X yellow | 52.79 | 0.00 | 0.00 |
| GV.GM7MDH.005.198)X | 67.12 | 0.79 | 0.53 |
| GV.GM7MDH.005.198)X | 46.97 | 0.43 | 0.20 |
| GV.GM7MDH.005.198)X | 38.60 | 1.80 | 0.69 |
| GV.GM7MDH.005.198)X | 57.87 | 0.81 | 0.47 |
| GV.GM7MDH.005.198)X | 60.76 | 0.64 | 0.39 |
| GV.GM7MDH.005.198)X | 37.45 | 1.78 | 0.67 |
| GV.GMWKWK.004.315)X (yellow) | 48.15 | 0.00 | 0.00 |
| GV.GMWKWK.004.315)X | 50.16 | 2.32 | 1.16 |
| GV.GMWKWK.004.315)X | 60.51 | 1.44 | 0.87 |
| GV.GMWKWK.004.315)X | 49.13 | 1.09 | 0.54 |
| GV.GM7MDH.008.956)X (yellow) | 50.07 | 0.00 | 0.00 |
| GV.GM7MDH.008.956)X (yellow) | 47.90 | 0.00 | 0.00 |
| GV.GM7MDH.008.956)X | 54.29 | 0.08 | 0.05 |
| GV.GM7MDH.008.956)X | 47.83 | 0.38 | 0.18 |
| GV.GM7MDH.008.956)X | 63.28 | 0.66 | 0.42 |
| GV.GM7MDH.008.956)X | 65.73 | 0.11 | 0.07 |
| GV.GM7MDH.008.956)X | 59.75 | 0.56 | 0.34 |
| GV.GM7MDH.008.956)X | 99.58 | 0.01 | 0.01 |
| GV.GMWKWK.001.407)X (yellow) | 70.43 | 0.00 | 0.00 |
| GV.GMWKWK.001.407)X (yellow) | 57.54 | 0.00 | 0.00 |
| GV.GMWKWK.001.407)X | 52.55 | 0.28 | 0.15 |
| GV.GMWKWK.001.407)X | 65.06 | 0.44 | 0.29 |
| GV.GMWKWK.001.407)X | 66.86 | 0.17 | 0.12 |
| GV.GMWKWK.001.407)X | 63.51 | 0.47 | 0.30 |
| GV.GMWKWK.001.407)X | 68.22 | 0.31 | 0.21 |
| GV.GMWKWK.001.407)X | 59.94 | 0.51 | 0.31 |
| GV.GMWKWK.001.419)X (yellow) | 76.57 | 0.00 | 0.00 |
| GV.GMWKWK.001.419)X (yellow) | 60.10 | 0.00 | 0.00 |
| GV.GMWKWK.001.419)X | 50.41 | 0.92 | 0.46 |
| GV.GMWKWK.001.419)X | 53.04 | 0.39 | 0.20 |
| GV.GMWKWK.001.419)X | 60.99 | 0.36 | 0.22 |
| GV.GMWKWK.001.419)X | 61.84 | 0.59 | 0.36 |

TABLE 5A-continued

Quantitative Mass Spectrometry analysis of single wildtype (yellow) and red soybeans harvested from segregating T0 plants expressing the LegHemoglobin construct targeted to the GY1 Locus

| SAMPLE ID | Soluble protein/total Protein (wt %) | LegHemoglobin protein/soluble protein (wt %) | LegHemoglobin protein/total protein (wt %) |
|---|---|---|---|
| GV.GMWKWK.001.419)X | 50.12 | 0.39 | 0.19 |
| GV.GMWKWK.001.419)X | 48.17 | 0.47 | 0.23 |
| GV.GM7MDH.001.628)X (yellow) | 67.58 | 0.00 | 0.00 |
| GV.GM7MDH.001.628)X (yellow) | 61.49 | 0.00 | 0.00 |
| GV.GM7MDH.001.628)X | 57.87 | 0.36 | 0.21 |
| GV.GM7MDH.001.628)X | 49.28 | 0.17 | 0.08 |
| GV.GM7MDH.001.628)X | 51.04 | 0.48 | 0.25 |
| GV.GM7MDH.001.628)X | 69.92 | 0.34 | 0.24 |
| GV.GM7MDH.001.628)X | 57.20 | 0.53 | 0.30 |
| GV.GM7MDH.001.628)X | 74.19 | 0.29 | 0.22 |

We planted T1 seeds from the same six events and performed the same PCR molecular analyses on those T1 plants. In these analyses, 2×HDR perfect integration T1 plants can only be consistently confirmed in three of the six events analyzed (198A, 315A, 628A), For the 956A event, only one 2×HDR plant can be detected from 37 T1 plants screened. For the other two events (407A and 419A), we cannot detect any 2×HDR PCR product, indicating that the 2×HDR signals from their T0 plant analyses were not transmitted to T1 plants, probably due to the chimeric nature in the transformation process. These two events were re-classified as random integrated transgenic events at T1 plants. T2 seeds will be harvested for 2×HDR prefect integrated events, as well as those random integrated transgenic events. The leghemoglobin level will be analyzed in all homozygous T2 seeds to compare the leghemoglobin expression level at the glycinin1 native locus to the random transgenic loci. It is expected that leghemoglobin levels will be doubled in the perfect integrated events as compared to the leghemoglobin level in T1 seeds, reaching about 2.3% or more of the total seed protein per dry weight basis.

Example 5: Genome Engineering of the Leghemoglobin Gene into Other Native Soybean Seed-Storage Protein Gene Loci Other seed storage proteins, such as other glycinin proteins or conglycinin proteins, are shown in Tables 6 and 7. The genes encoding these storage proteins are used as the gene editing targets for soybean leghemoglobin over-expression in soybean seeds as described in this example.

TABLE 6

Expression profiling of glycinin 1 (bold) and other putative glycinin family members in soybean.

| | young_leaf | flower | one cm pod | pod shell 10DAF | pod shell 14DAF | seed 10DAF | seed 14DAF | seed 21DAF | seed 25DAF | seed 28DAF | seed 35DAF | seed 42DAF | root | nodule |
|---|---|---|---|---|---|---|---|---|---|---|---|---|---|---|
| Glyma03g32020 | 0 | 0 | 0 | 0 | 0 | 2 | 2 | 12 | 26498 | 72276 | 218636 | 210908 | 0 | 0 |
| **Glyma.03g163500** | **0** | **1** | **0** | **1** | **0** | **0** | **0** | **5** | **34953** | **87714** | **288053** | **298305** | **0** | **0** |
| Glyma.10g037100 | 0 | 0 | 0 | 0 | 0 | 0 | 1 | 3 | 11410 | 29176 | 166962 | 249297 | 0 | 0 |
| Glyma.13g123500 | 0 | 0 | 0 | 0 | 0 | 0 | 0 | 0 | 5591 | 15500 | 92982 | 130315 | 0 | 0 |
| Glyma.19g164800 | 0 | 0 | 0 | 0 | 0 | 0 | 1 | 10 | 62 | 48 | 225 | 186 | 0 | 0 |
| Glyma.19g164900 | 1 | 0 | 0 | 0 | 0 | 0 | 0 | 0 | 883 | 2263 | 10523 | 12595 | 2 | 0 |

TABLE 7

Expression level of 7 β-conglycinin isoforms in soybean seeds 30 or 50 days after flowering.

| β-conglycinin | Expression level measured by RNAseq |
|---|---|
| Glyma.20g148200 (β) | 19251 (30DAF) |
| Glyma.20g148300 (α) | 67117 (30DAF) |
| Glyma.20g148400 (α) | 91647 (30DAF) |
| Glyma.20g146200 (β) | 7068 (30DAF) |
| Glyma.10g246300 (α') | 86918 (30DAF) |
| Glyma.10g246500 (α') | 20492 (50DAF) |
| Glyma.10g246400 (α) | No/low expression 6 (30DAF) |

Specific gRNAs are designed for these genes following the protocol in example 4. The binary vectors for each gene target are introduced into soybean plants by *Agrobacterium*-mediated soybean embryonic axis transformation. With site-specific integration of the donor DNA by homology-mediated double strand break DNA repair process, genome editing variants of seed-storage protein genes with the soybean leghemoglobin replacing the coding sequences are created for each seed-storage protein gene, alone or in combination with GLY1 or other seed storage protein genes. Plants are grown in the greenhouse. We expect the harvested $T_1$ seeds to contain a leghemoglobin amount of at least 1% of total seed protein or higher.

Example 6: Improvement of Soybean Leghemoglobin Expression Level in Soybean Seeds by Protein Rebalancing Glycinin and conglycinin are two major classes of seed storage proteins in soybean seeds. In soybean seeds, β-conglycinin, the abundant 7S globulin storage protein, and glycinin consist of about 21% and 33% of total protein content, respectively (Utsumi et al., 1997). Total soybean protein content did not change after silencing a and α' subunits of β-conglycinin by RNAi (Kinney et al., 2001). The resulting engineered seeds accumulated more glycinin that accounts for more than 50% of total seed protein, which compensated for the missing β-conglycinin in the engineered seeds. β-conglycinin consists of 3 isoforms, α, α' and β. If desirable, the β-conglycinin gene family (6 to 7 genes for the alpha', alpha and beta subunits) can be eliminated with gene cluster dropouts or frameshift knockout mutations by CRISPR/Cas editing, then channel more protein synthesis resource to leghemoglobin production in soybean seeds.

As an example, gRNAs were designed to knockout 6 putative β-conglycinin isoforms by Cas9/gRNA editing to rebalance the proteome to glycinin. Seven β-conglycinin candidates including 3α, 2α' and 2β isoforms were identified. Except for Glyma.10g246400 (α) and Glyma.20g146200 (β), all other isoforms show relatively high expression level at 30 or 50 days after flowering (DAF) in soybean seeds (Table 7).

Figure 5:
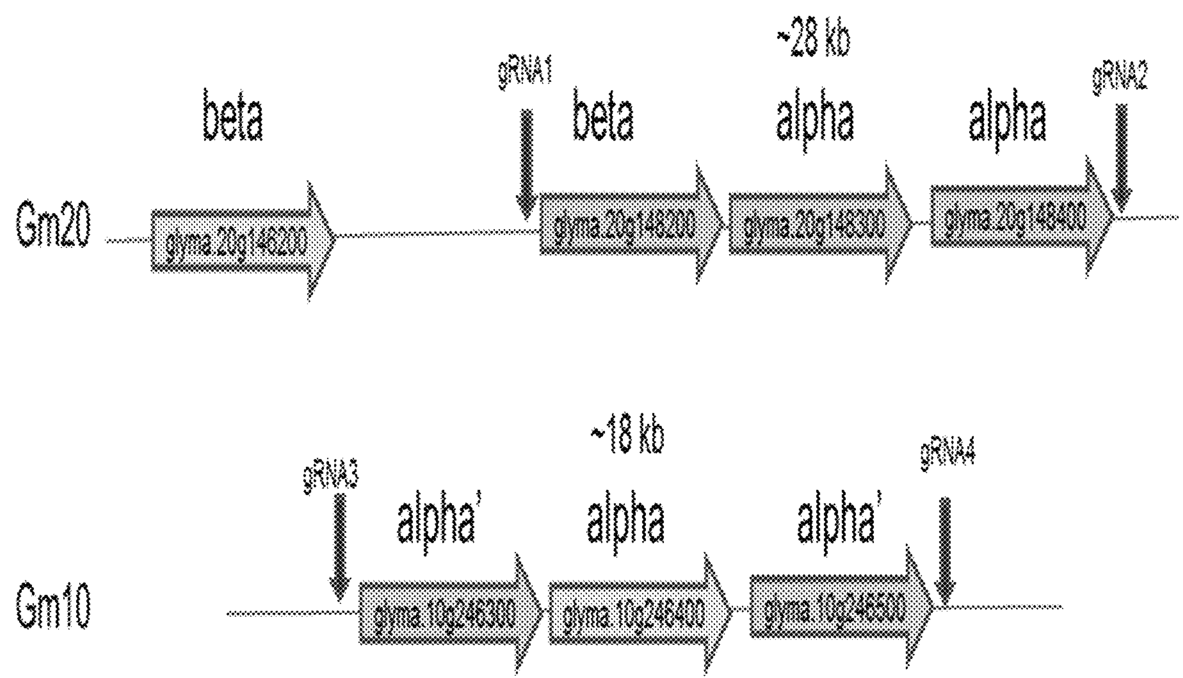
FIG. 5 is a schematic showing the gene dropout strategy for the conglycinin gene cluster loci.

Four gRNAs were used to delete 6 of 7 β-conglycinin isoforms. The GM-CONG-gRNA1 (SEQ ID NO: 24) and GM-CONG-gRNA2 (SEQ ID NO: 25) were used to dropout the conglycinin cluster on chromosome 20 (Gm20); the GM-CONG-gRNA3 (SEQ ID NO: 26) and GM-CONG-gRNA4 (SEQ ID NO: 27) were used to dropout the conglycinin cluster on chromosome 10 (Gm10), as illustrated in FIG. 5.

Figure 6:
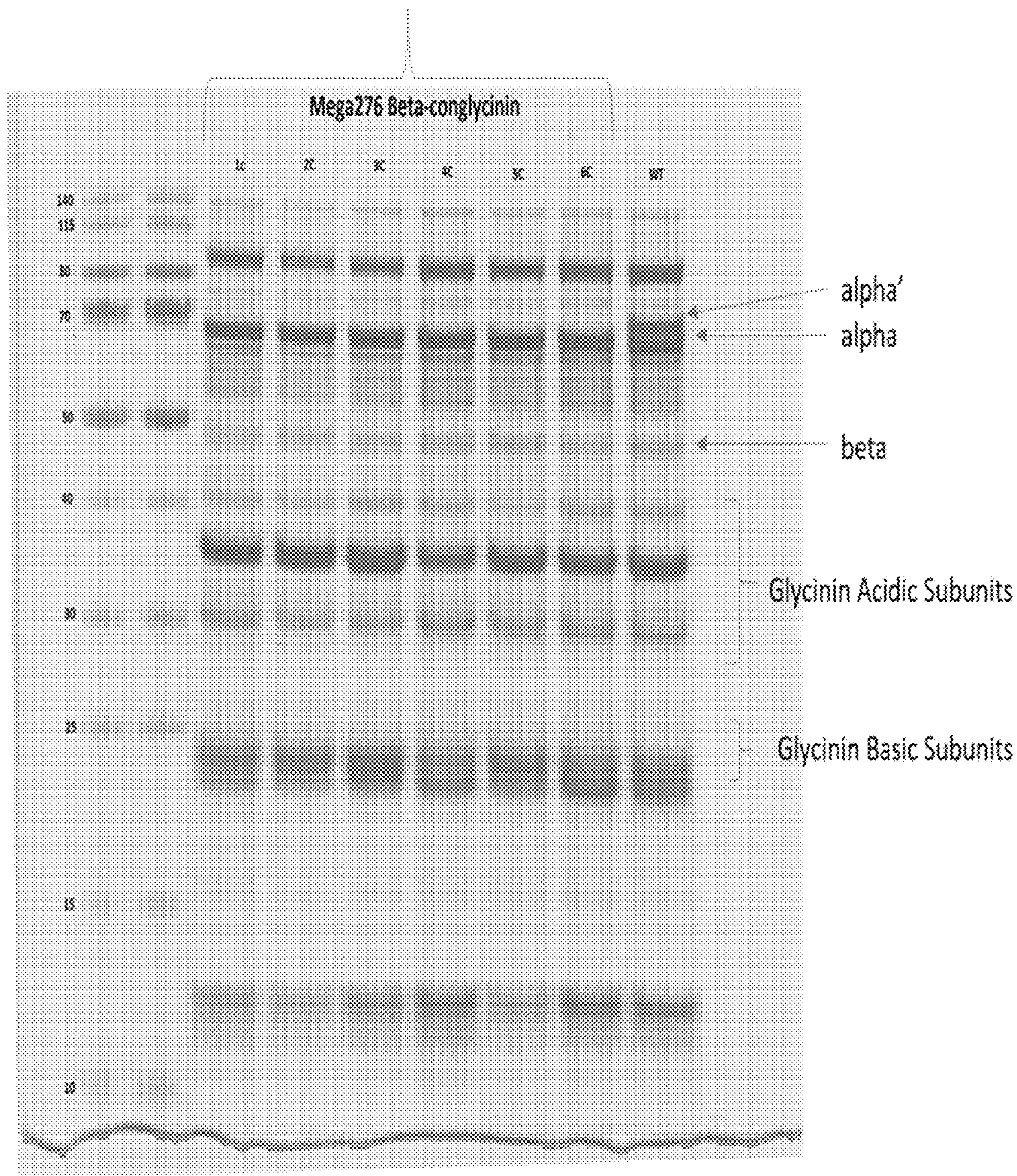
FIG. 6 is a photograph of a protein gel showing the seed protein profile of the conglycinin Gm10 gene cluster dropout variants.
Figure 7:
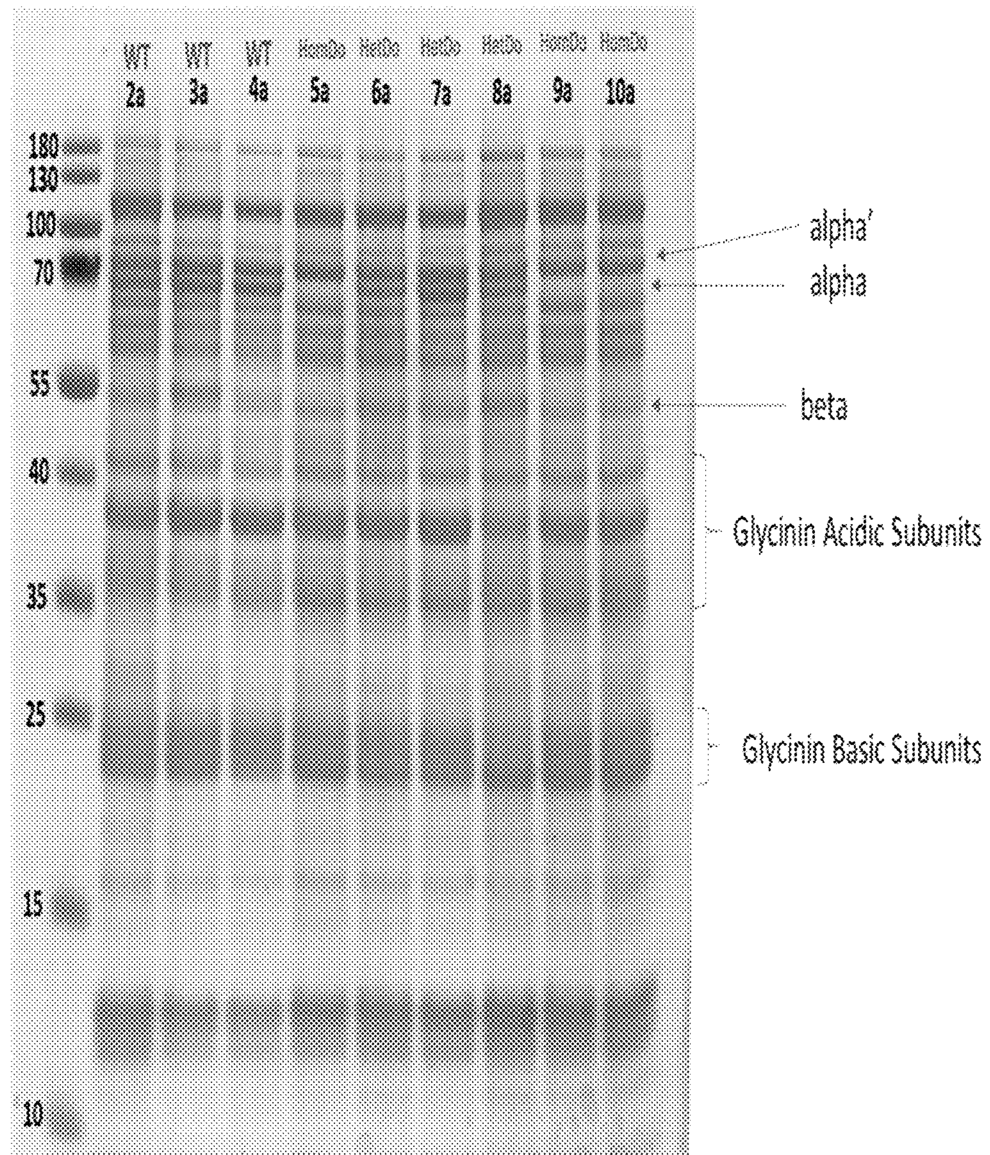
FIG. 7 is a photograph of a protein gel showing the seed protein profile of the conglycinin Gm20 gene cluster dropout variants

T2 homozygous seeds from the conglycinin Gm10 locus dropout experiment were generated. Seed protein analyses was conducted by SDS-PAGE Coomassie Blue gel staining analyses (FIG. 6). No alpha' subunits of conglycinin proteins can be detected in those T2 homozygous seeds from the Gm10 locus dropout variants, demonstrating complete removal of the conglycinin alpha' subunit proteins in soybean seeds, in agreement with the complete removal of their genes from soybean genome. The total protein content of these T2 seeds did not change as compared to wild type seeds, indicating other soybean proteins are compensating for the loss of conglycinin alpha' subunit proteins in these editing variants. For the second editing experiment, the T2 seeds from the Gm20 locus dropout were analyzed by protein gel analyses (FIG. 7). The results indicated that the conglycinin alpha subunit proteins had been completely removed in soybean seeds of the homozygous dropout plants. The data also indicated that the conglycinin beta subunit protein was also reduced in this dropout variant due to the elimination of Glyma.20g148200 gene. However, some of the beta subunits could still detected since the dropout design did not include the moderate expressed Glyma.20g146200 gene. These alpha' and alpha/beta dropout loci will be genetically crossed together to create complete conglycinin knockout soybean seeds.

In another editing experiment, three gRNAs (SEQ ID NOs: 28, 29, 30) were designed to do frameshift knockout of 5 highly expressed conglycinin genes (glyma.20g148200, glyma.20g148300, glyma.20g148400, glyma.10g246300 and glyma.10g246500) and one moderate-level expressed glyma.20g146200, in a multiplex frameshift knockout approach. The Homozygous T2 seeds will be analyzed for protein profile change and amino acid composition improvement.

The leghemoglobin over-expression approach and the conglycinin knockout approach are combined by either genetic crosses, or by performing gene editing in the leghemoglobin over-expression soybean lines, or by retransforming the leghemoglobin over-expression cassettes into the conglycinin knockout soybean lines. With the absence of conglycinin proteins in those soybean seeds, the contents of glycinin or other soybean proteins are expected increase to compensate the loss of conglycinin protein through protein rebalancing. It is expected that by combining the soybean leghemoglobin overexpression with the conglycinin dropout approaches, the leghemoglobin level in soybean seeds is increased.

Figure 8:
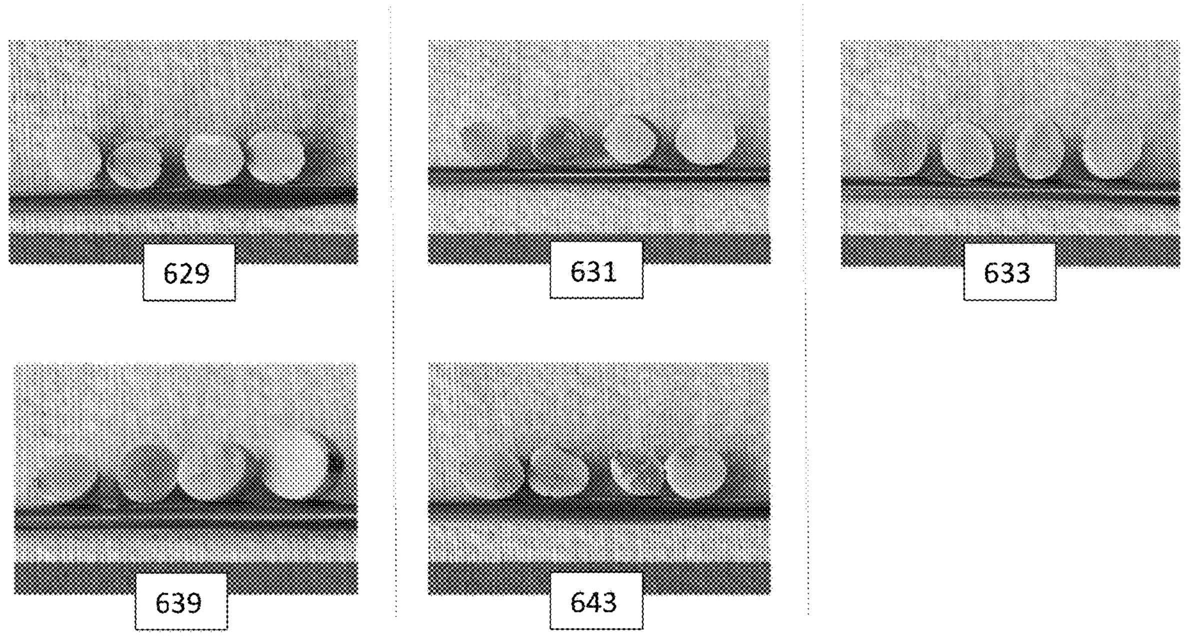
FIG. 8 is a photograph of seed cross sections of 5 independent events in experiment 1.
Figure 9:
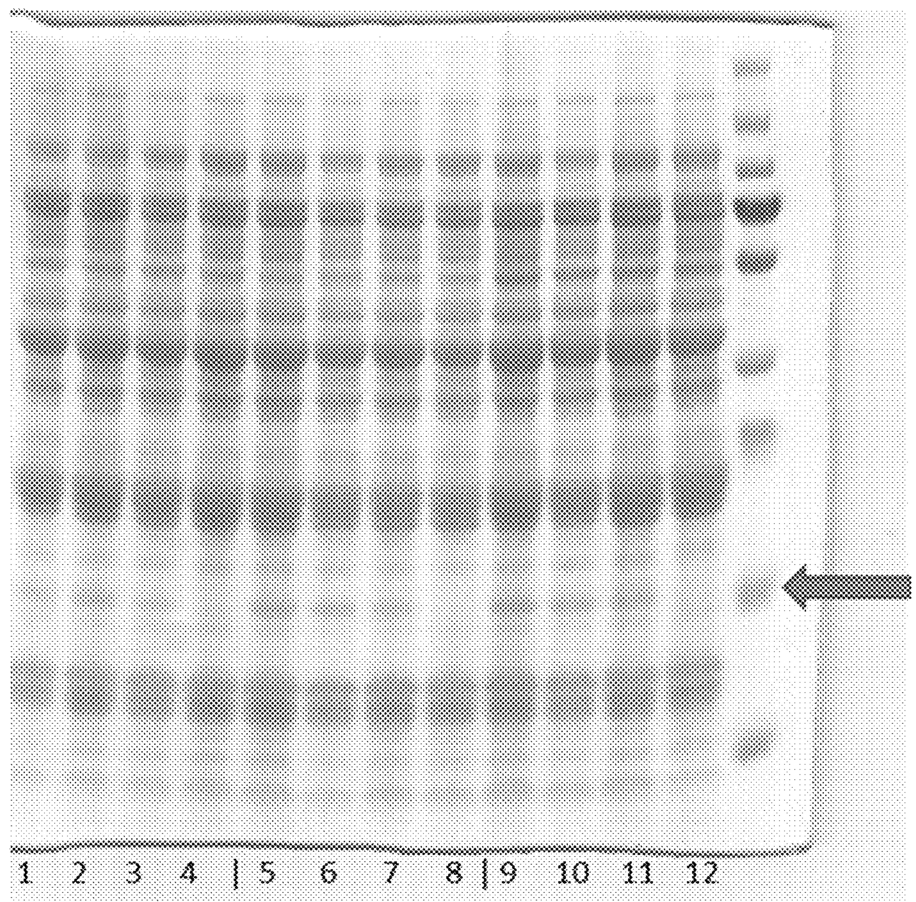
FIG. 9 is a photograph of a Coomassie-stained protein gel showing the presence of 16KD leghemoglobin protein in experiment 1 (arrowed).
Figure 10:
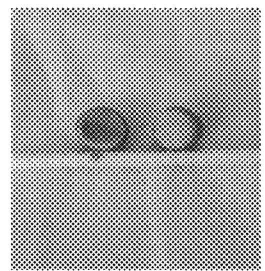
FIG. 10 is a photograph of seed cross sections of 4 independent events in experiment 5.
Figure 10:
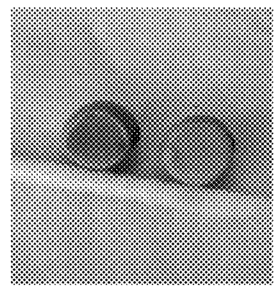
Figure 10:
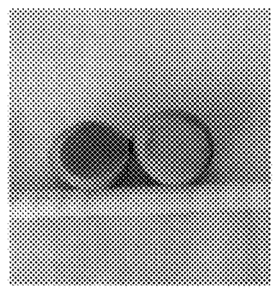
Figure 10:
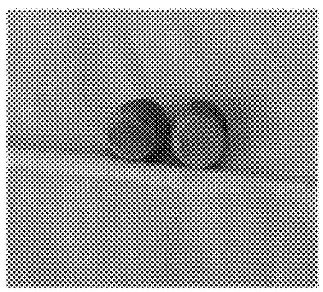

Example 7: Characterization of Soybean Leghemoglobin Expression in Soybean Seeds For the 8 transgenic constructs described in Example 1 and 2, T1 seeds were generated. The results were very surprising. There was almost no leghemoglobin protein accumulated in the two constructs with the GY1-SP/GY1 Basic Subunit targeting design (Experiment 4 and 8 in FIGS. 1 and 2). There is very low level of leghemoglobin accumulation (~0.1% of total seed protein) in the two constructs with Lectin SP targeting design (Experiment 3 and 7 in FIGS. 1 and 2) and the soybeans appeared yellow. The best expression design was from the two constructs with No Signal Peptide for the leghemoglobin (Experiment 1 and 5, shown in FIGS. 1 and 2). As shown in FIGS. 8 and 10, the "red" (i.e. pink tinged in the transverse section) colored seeds were easily identifiable by eye in these two experiments, indicating that the leghemoglobin expression level is high and the proteins were efficiently assembled as leghemoglobin protein complex containing an iron centered porphyrin (heme). Five events from the experiment 1 design (No signal peptide) and 4 events from the experiment 5 design (no signal peptide plus two heme pathway genes)

were generated and all 9 events had the "red" seed phenotype. The presence of the leghemoglobin in the seeds was further verified by performing seed protein extraction, SDS PAGE gel, and Coomassie blue staining. The 16KD leghemoglobin is easily visible by Coomassie blue staining (arrows in FIGS. 9 and 11). In FIG. 9, lanes 1, 2, 3, 5, 6, 7, 9, 10, 11 are the protein samples from the "red" pink-colored leghemoglobin positive seeds from three independent events in experiment 1 design, and lanes 4, 8, and 12 are the protein samples from the yellow null segregate seeds from the same three events. Similarly, in FIG. 11, the #14 lane is from the yellow null segregate seeds, and the #11, #21, #33, #43 are the protein samples from the "red" (pink color) leghemoglobin positive seeds from three independent events from the experiment 5 design.

Sample Preparation for Single Seed Analysis.

Single $T_1$ red and yellow soybeans harvested from individual segregating $T_0$ plants were placed in a Spex Certiprep ½×2" polycarbonate vial with cap (cat #3116PC). A ⅜" stainless steel ball bearing was added. Grinding was performed in a Spex Certiprep 2000 Geno/Grinder at 1500 strokes/min for three 30 second intervals with a 1-minute rest between each cycle.

Alternatively, soybeans were ground with a pestle, in the presence of liquid nitrogen, in a precooled mortar. The powders were then lyophilized for 48 h and kept at −20° C. in a desiccator until processed.

Moisture Content Determinations were Performed According to American Oil Chemists Society (AOCS Official Method Ba 2a-38, Modified for Small Samples) as Follows:

Weigh powdered sample material (approximately 100 mg; to an accuracy of 0.1 mg) into a pre-weighed (and recorded) 13×100 mm glass tube VWR (53283-800) and weigh again.

Place samples into a forced air oven preheated to 130° C. Allow material to dry for 2 h.

Remove tubes into a desiccator cabinet and allow to come to room temperature before weighing again.

Cap tube and save residual dried material for subsequent combustion analysis for protein (see below).

Store in a desiccator for further analysis.

Total Protein Analysis.

Protein contents were estimated by combustion analysis of the oven dried or lyophilized powders described above. Analysis was performed on a Flash 1112EA combustion analyzer (commercially available from Thermo) running in the N-protein mode, according to the manufacturer's instructions, using aspartic acid as the standard. The powdered samples, 30-40 mg, weighed to an accuracy of 0.001 mg on a Mettler-Toledo MX5 microbalance were used for analysis. Protein contents were calculated by multiplying % N, determined by the analyzer, by 6.25. Final protein contents were assumed to be at a dry basis for the oven dried material and on an as measured basis for the lyophilized material.

Calculation of Moisture Content. The as is moisture content of the tissues was determined after oven drying using the following formula:

$$\text{Moisture} = \frac{(wt.\ \text{tube} + \text{tissue as is} - wt.\ \text{tube}) - (wt.\ \text{tube} + \text{tissue dry} - wt.\ \text{tube})}{(wt.\ \text{tube} + \text{tissue as is} - wt.\ \text{tube})} \times 100$$

Quantitation of Globin Protein by LC-MS-MS.

The amino acid sequence of the globin protein (Table 1; SEQ ID 2) was assessed in-silico for potential trypsin digestion sites and the suitability of the resultant peptides for quantitative mass spectrometry. The following criteria were applied;

The peptide was between 6 and 20 amino acids in length

The amino acids within the peptide were unlikely to undergo secondary modifications.

The absence of sulfur containing amino acids

Solubility and iso-electric point.

Using these criteria, three potential peptides were identified. These were further analyzed using an online application available from Thermo Fisher Scientific at thermofisher.com/us/en/home/life-science/protein-biology/peptides-proteins/custom-peptide-synthesis-services/peptide-analyzing-tool.html. Based on the output of this application two peptides were selected. The sequences of these peptides were subjected to a BLAST search using the NCBI Protein BLAST (protein-protein) program blast.ncbi.nlm.nih.gov/Blast.cgi?PROGRAM=blastp&PAGE_TYPE=BlastSearch&LINK_LOC=blasthome and were determined to be unique to the soybean globin sequence within the soybean (*Glycine max*) genome. The peptides were synthesized as follows:

```
Peptide 1:
                                        SEQ ID NO: 33
K.ANGTVVADAALGSIHAQK.A
[position 78-95 of SEQ ID NO: 2]

Peptide 2:
                                        SEQ ID NO: 34
K.AITDPQFVVVK.E
[position 96-106]
```

Where the "." indicates the enzymatic digestion site and the parenthetical values denote the amino acid residue position relative to the N-terminal end of the mature globin protein.

Peptide stocks, at a concentration of 500 ppm, were prepared and stored as aliquots at −80° C. These stocks were used to further assess the suitability of the peptides for quantitative analysis. Peptide stocks were infused into the Mass Spectrometer (SCIEX 5500 Qtrap; SCIEX LLC, Redwood City, Calif. USA) to optimize the parameters for detection. Upon analysis, the peptide AITDPQFVVVK (Peptide 2) proved to be the best candidate, with a +2 charge state of the parent ion (608.9 m/z). Following optimization of fragmentation in the collision cell, a surrogate daughter ion (816.6 m/z) with the highest abundance, was chosen to develop quantitation against. A second confirmatory ion (444.3 m/z) was also chosen.

Sample Preparation

Powder samples of ~10-20 mg (weighed and recorded to an accuracy of 0.1 mg) were placed into 1.2 ml Micro Titer Tubes (Fisher Brand 02-681-376). Extraction buffer, 8 mM (3-[(3-Cholamidopropyl)dimethylammonio]-1-propanesulfonate hydrate, (CHAPS); 0.1% Triton X-100, pH 8.4 was added at a tissue weight to volume ratio of 25. One small steel ball was added to each vial and after capping the samples were extracted in a Geno/Grinder; 1150 oscillations per minute for 30 seconds. The contents of the homogenization tube, minus the steel ball, were quantitatively transferred to clean 1.5 ml microfuge tubes and the samples were cleared in a microcentrifuge; 10,670×g for 10 minutes. The supernatants were transferred to clean 1.5 ml microcentrifuge tubes and the samples were again centrifuged; 10,670×g, for 5 minutes. Total soluble protein concentrations of the supernatants were determined using the Bradford assay and the results were used to normalize samples to 1 mg soluble protein per ml, by dilution with trypsin digestion buffer (100 mM Ammonium Bicarbonate; 0.05% Tween-20; pH 8.3). Samples were prepared for trypsin digestion by adding 50 ul of the protein normalized extract to 100 ul of trypsin digestion buffer, 6 ul of 0.25M DTT (dithiothreitol; in digestion buffer) and incubating them at 95° C. for 20 minutes. Iodoacetamide, 6 ul of 300 mM stock was added to each sample and they were incubated in the dark for one hour at room temperature. Trypsin (Pierce, MS Grade; Thermo Fisher Scientific) 10 ul of 0.1 ug/ul stock, was added to each sample and they were incubated overnight at 37° C. in a static incubator. The tryptic digestions were terminated by the addition of 10 ul of 10% formic acid. Samples were then analyzed using UHPLC-MS-MS analysis.

LC/MS/MS Methods

Quantitative analysis of the tryptic digests was performed on a UHPLC (Agilent 1290) with SCIEX 5500 Qtrap detector, operating in the positive ion mode. Samples and standards (10 ul injections) were separated on a Waters Cortex C18, 2.7 um (2.1×100 mm) reverse phase column maintained at 40° C. The solvent flow rate was 300 ul/min with starting conditions of, 90% solvent A (99.9% MS grade Water; 0.1% Formic Acid)-10 solvent B (99.9% Acetonitrile, 0.1% Formic Acid). The conditions were ramped to 60% solvent A-40% solvent B over a 7 minute period, followed by a further ramp to 10% Solvent A-90% Solvent B over 0.5 min. The solvents were then returned to the starting conditions, over a 3 minute period and the column was equilibrated under the starting conditions for a further 3 minutes before the next injection. An Electrospray Ionization (ESI) source was used to introduced samples into the MS. Source parameters were as follows: Declustering potential 135 (V), Temperature 350° C., and Ion Spray voltage 350V. An MRM (Multiple Reaction Monitoring) detection technique was used to identify and quantitate the product ion (m/z: 816.6) using a collision cell energy of 35 (eV) to fragment the parent+2 molecule (m/z 608.9). Another product ion (m/z: 444.3) was used to confirm identity (based on the presence or absence). Quantitation was performed against a standard curve of the peptide that had been taken through all of the sample preparation steps described above.

Table 8 shows the Quantitative Mass Spectrometry analysis of yellow (WT) and red soybeans harvested from segregating $T_0$ plants expressing the LegHemoglobin construct with no targeting sequences (Material from Experiment 1). Soluble protein was measured in the analyzed extracts and is expressed as a % of the total protein contents of the bean powders, as determined by combustion analysis. The LegHemoglobin protein was quantified by UHPLC-MS-MS and is expressed on a wt % of the soluble protein or total protein basis.

TABLE 8

Quantitative Mass Spectrometry analysis of wildtype (yellow) and red soybeans harvested from segregating $T_0$ plants expressing the LegHemoglobin construct with no targeting sequences

| SAMPLE ID | Soluble protein/total Protein (wt %) | LegHemoglobin protein/soluble protein (wt %) | LegHemoglobin protein/total protein (wt %) |
|---|---|---|---|
| GMZ3A9.1.20; A | 56.6 | 0.83 | 0.47 |
| GMZ3A9.1.20; B | 56.9 | 1.35 | 0.77 |
| GMZ3A9.1.20; C | 74.2 | 0.49 | 0.37 |
| GMZ3A9.1.22; A | 62.5 | 1.15 | 0.72 |
| GMZ3A9.1.22; B | 65.9 | 1.10 | 0.72 |
| GMZ3A9.1.24; A | 81.3 | 0.95 | 0.77 |
| GMZ3A9.1.24; B | 50.7 | 1.42 | 0.72 |
| GMZ3A9.1.24; C | 65.0 | 0.73 | 0.48 |
| GMZ3A9.1.30; A | NA | 0.97 | NA |
| GMZ3A9.1.30; B | 48.6 | 0.97 | 0.47 |
| GMZ3A9.1.30; C | 27.7 | 0.88 | 0.24 |
| GMZ3A9.1.30 WT | 59.3 | 0.00 | 0.00 |
| GMZ3A9.1.34; A | 75.8 | 1.06 | 0.80 |
| GMZ3A9.1.34; B | 35.0 | 1.93 | 0.68 |
| GMZ3A9.1.34; C | 65.7 | 1.24 | 0.81 |
| GMZ3A9.1.20; WT | 59.3 | 0.00 | 0.00 |
| GMZ3A9.1.20; B | 66.3 | 0.34 | 0.23 |
| GMZ3A9.1.22; A | 62.8 | 0.88 | 0.55 |
| GMZ3A9.1.30; A | 66.6 | 0.88 | 0.58 |
| GMZ3A9.1.34; A | 67.5 | 1.12 | 0.77 |
| GMZ3A9.1.34; B | 77.4 | 0.97 | 0.74 |

Expression of the soluble protein of the extracted sample as a % of the total protein content of the starting material indicated that the efficiency of extraction ranged from 27.7-81.3%, average 61.3% (Table 8). This led to substantial differences in the % globin protein contents, when expressed on a per unit soluble protein or per unit total protein basis. Yellow, wild type beans (GMZ3A9.1.30 WT and GMZ3A9.1.20; WT), had no detectable globin protein in them (Table 8). Red beans had between 0.34-1.93 wt % globin protein, when expressed on a soluble protein basis and up to 0.8 wt % when expressed on a total protein basis.

To improve the extraction efficiency and make the sample preparation more uniform the sample preparation was modified as follows; powder samples of 10+/−0.5 mg (weighed and recorded to an accuracy of 0.1 mg) were placed into 1.2 ml Micro Titer Tubes (Fisher Brand 02-681-376). Extraction buffer, 8 mM (3-[(3-Cholamidopropyl)dimethylammonio]-1-propanesulfonate hydrate, (CHAPS); 0.1% Triton X-100, pH 8.4 was added at a tissue weight to volume ratio of 50. One small steel ball was added to each vial and after capping the samples were extracted in a Geno/Grinder; 1150 oscillations per minute for 30 seconds and then on an end over end rotator for 10 minutes, the genogrinding step was then repeated. The contents of the homogenization tube, minus the steel ball, were quantitatively transferred to clean 1.5 ml microfuge tubes and the samples were cleared in a microcentrifuge; 10,670×g for 10 minutes. The supernatants were transferred to clean 1.5 ml microcentrifuge tubes and the samples were again centrifuged; 10,670×g, for 5 minutes. Total soluble protein concentrations of the supernatants were determined using the Bradford assay and the results were used to normalize samples to 1 mg soluble protein per ml, by dilution with trypsin digestion buffer (100 mM Ammonium Bicarbonate; 0.05% Tween-20; pH 8.3). Samples were prepared for trypsin digestion by adding 25 ul of the protein normalized extract to 125 ul of trypsin digestion buffer, 6 ul of 0.25M DTT (dithiothreitol; in digestion buffer) and incubating them at 95° C. for 20 minutes. Iodoacetamide, 6 ul of 300 mM stock was added to each sample and they were incubated in the dark for one hour at room temperature. Trypsin (Pierce, MS Grade; Thermo Fisher Scientific) 10 ul of 0.1 ug/ul stock, was added to each sample and they were incubated overnight at 37° C. in a static incubator. The tryptic digestions were terminated by the addition of 10 ul of 10% formic acid. Samples were then analyzed using UHPLC-MS-MS analysis.

The modified extraction method resulted in an average of 97% (range 95.5-100%) of the soluble protein being extracted in the first extraction. This represented an average of 71% (range 62-78%) of the total protein content of the extracted material. Using this method, yellow and red soybeans from events where only the Leg Hemoglobin was being expressed (Experiment 1) were compared to yellow and red beans from events where the Leg Hemoglobin protein was being expressed (no signal peptide) in conjunction with two heme pathway genes (Experiment 5). The results are shown in Table 9. Quantitative Mass Spectrometry analysis of yellow (WT) and red soybeans harvested from segregating $T_0$ plants expressing only the leghemoglobin construct (no targeting sequences) Experiment 1 or the leghemoglobin construct (no targeting sequences) in conjunction with two heme pathway genes (Experiment 5). Soluble protein was measured in the analyzed extracts and is expressed as a % of the total protein contents of the bean powders, as determined by combustion analysis. The leghemoglobin protein was quantified by UHPLC-MS-MS and is expressed on a wt % of the soluble protein or total protein basis.

TABLE 9

Quantitative Mass Spectrometry analysis of wildtype (yellow) and red soybeans harvested from segregating $T_0$ plants expressing the leghemoglobin construct with no targeting sequences (Experiment 1) or the leghemoglobin construct (no targeting sequences) in conjunction with two heme pathway genes (Experiment 5)

| SAMPLE ID | Soluble protein/total Protein (wt %) | Leghemoglobin protein/soluble protein (wt %) | Leghemoglobin protein/total protein (wt %) |
|---|---|---|---|
| EXPERIMENT 1 LegH Only | | | |
| GMZ3A9.1.20; WT | 76.5 | 0 | 0 |
| GMZ3A9.1.20; 29 | 72.8 | 0.31 | 0.21 |
| GMZ3A9.1.22; 31 | 69.4 | 0.81 | 0.54 |
| GMZ3A9.1.30; 39 | 78.2 | 0.79 | 0.60 |
| GMZ3A9.1.34; 43-1 | 63.0 | 1.16 | 0.70 |
| GMZ3A9.1.34; 43.2 | 70.9 | 1.13 | 0.80 |
| EXPERIMENT 5 LegH plus heme pathway augmentation | | | |
| GM9RDV.001.5a; WT | 75.1 | 0 | 0 |
| GM9RDV.001.5a; 5.0 | 63.2 | 1.01 | 0.64 |
| GM9RDV.001.5a; 5.3 | 75.1 | 1.09 | 0.82 |
| GM9RDV.001.5a; 6.0 | 60.5 | 1.13 | 0.68 |
| GM9RDV.001.18a; WT | 59.1 | 0 | 0 |
| GM9RDV.001.18a; 6 | 52.6 | 0.78 | 0.1 |
| GM9RDV.001.18a; 7 | 64.7 | 0.64 | 0.42 |
| GM9RDV.001.18a; 18.2 | 68.5 | 1.12 | 0.78 |

The data show that the quantity of the leghemoglobin protein reached similar levels in both experiments indicating that the up regulation of the heme pathway did not positively or negatively influence the level of leghemoglobin protein in these events with a maximum level, when expressed on a total protein basis reaching 0.82% for the leghemoglobin protein plus heme pathway genes (Experiment 5) and 0.80% for the leghemoglobin protein only material (Experiment 1).

Visually there were no obvious intensity differences in the red color of the beans from each experiment, which was interpreted as showing that there was no difference in the amount of leghemoglobin protein complex in the beans from the two experiments. Seed from Experiments 1 and 5 were analyzed at the next generation.

TABLE 9A

Quantitative Mass Spectrometry analysis of wildtype (yellow) and red (pink) soybeans harvested from segregating $T_1$ plants expressing the leghemoglobin construct with no targeting sequences (Experiment 1) or the leghemoglobin construct (no targeting sequences) in conjunction with two heme pathway genes (Experiment 5)

| SAMPLE ID | Soluble protein/total Protein (wt %) | Leghemoglobin protein/soluble protein (wt %) | Leghemoglobin protein/total protein (wt %) |
|---|---|---|---|
| EXPERIMENT 1 LegH Only | | | |
| GMZ3A9.001.24 | 94.34 | 1.45 | 0.66 |
| GMZ3A9.001.20a | 83.19 | 0.00 | 0.00 |
| GMZ3A9.001.30a | 66.08 | 1.76 | 0.07 |
| GMZ3A9.001.22a | 65.07 | 2.54 | 0.41 |
| GMZ3A9.001.34a | 85.76 | 1.14 | 0.93 |
| GMZ3A9.001.24a | 53.99 | 2.90 | 1.38 |
| GMZ3A9.001.20a | 88.48 | 1.16 | 0.03 |
| GMZ3A9.001.30a | 66.53 | 2.06 | 0.11 |
| GMZ3A9.001.22a | 59.80 | 1.96 | 0.41 |
| GMZ3A9.001.20a | 83.19 | 0.00 | 0.00 |
| EXPERIMENT 5 LegH plus heme pathway augmentation | | | |
| 93Y21 | 69.60 | 0.00 | 0.00 |
| GM9RDV.001.5a | 92.14 | 2.26 | 1.84 |
| GM9RDV.001.20a | 75.51 | 3.02 | 1.07 |
| GM9RDV.001.26a | 95.73 | 1.76 | 0.34 |
| GM9RDV.001.5a | 86.66 | 0.00 | 0.00 |
| GM9RDV.001.5a | 88.09 | 1.77 | 0.05 |
| GM9RDV.001.20a | 78.21 | 1.47 | 1.02 |
| GM9RDV.001.26a | 86.02 | 1.68 | 0.58 |

The data in Table 9A show that homozygous seed have higher amounts of leghemoglobin than the T1 seed from the same events. For example, in T2 seed from event GMZ3A9.001.24a 1.38% of the total protein was determined to be leghemoglobin (dry basis), compared to 0.65 wt % in T1 seed, a two-fold increase. Similarly, in T2 seed from event GM9RDV.001.5a, 1.84 wt % of the total protein was determined to be leghemoglobin (dry basis) compared to a T1 seed value of 0.71 wt % (three seed average), a 2.6 fold increase. The data indicate that leghemoglobin levels double when seeds are homozygous.

Example 8: Stacking of Soybean Leghemoglobin Line with High Oleic Acid Lines

The transgenic leghemoglobin events describe above are genetically crossed with a high oleic line, such as a soybean line containing at least 50%, 70% or 75% oleic acid of the total fatty acids. Similarly, the leghemoglobin gene editing variant described above is genetically crossed with the high oleic line, such as containing at least 50%, 70% or 75% oleic acid of the total fatty acids. Alternately, leghemoglobin gene editing is performed directly in the high oleic acid line. Furthermore, both leghemoglobin gene editing and FAD2/FAD3 editing are performed together to stack the leghemoglobin trait with the high oleic trait exclusively through a gene editing approach. The resulting soybean seeds have increased nutritional value and provide an improved flavor to the soybean protein, soybean isolate or soybean concentrate.

Example 9: Extraction of Leghemoglobin Complex from Soybeans

In order for the leghemoglobin complexed protein to be used for downstream products the soybeans require processing. Typically, this involves: tempering, cracking, dehulling, solvent extraction of the oil, and toasting to remove residual solvent and to inactivate proteinaceous antinutritional factors, such as protease inhibitors. The meals or flours (typically greater than 47.5% protein) resulting from these processing steps can be further refined to concentrate the protein fraction by the removal of soluble sugars, to form soybean protein concentrates (typically greater than 65% protein). There are three processes used to create soy protein concentrates, namely alcohol washing, acid washing or hot-water extraction (Deak, N. A., Johnston, L. A., Lusas, E. W., and Rhee, K. C., 2008. Soybeans: Chemistry, Production, Processing, and utilization. Johnston, L. A., White, P. J., and Galloway, R. eds AOCS Press). All of these processes would be expected to substantially de-hemelate the leghemoglobin complexes making them unsuitable for recovery and subsequent use.

Alternatively, soybeans can be processed to the form of soy protein isolates (typically greater than 90% protein). This is achieved by solubilization of the protein fraction of lightly toasted white flake (defatted meal), prior to centrifugation to remove the bulk of the insoluble carbohydrate (fiber) fraction. The protein is then precipitated, by pH adjustment, and washed to remove remaining soluble carbohydrates. The purified protein fractions are pasteurized to inactivate residual protease inhibitor activity and microbial contaminants, prior to drying to a powder. These final steps in the soy isolate production process would also be expected to substantially de-hemelate the leghemoglobin complexes making them unsuitable for recovery and subsequent use.

To investigate the solubility/extractability of the leghemoglobin protein from soybeans the following experiment was performed. Soybean powder samples from red leghemoglobin expressing soybeans (10+/−0.5 mg; weighed and recorded to an accuracy of 0.1 mg) were placed into 1.2 ml Micro Titer Tubes (Fisher Brand 02-681-376). Extraction buffer, 8 mM (3-[(3-Cholamidopropyl)dimethylammonio]-1-propanesulfonate hydrate, (CHAPS); 0.1% Triton X-100, pH 8.4 was added at a tissue weight to volume ratio of 50. One small steel ball was added to each vial and after capping the samples were extracted in a Geno/Grinder; 1150 oscillations per minute for 30 seconds and then on an end over end rotator for 10 minutes, the genogrinding step was then repeated. The contents of the homogenization tube, minus the steel ball, were quantitatively transferred to clean 1.5 ml microfuge tubes and the samples were cleared in a microcentrifuge; 10,670×g for 10 minutes. The supernatant was transferred to clean 1.5 ml microcentrifuge tubes. The residual pellet from this step was extracted, as described, two more times. Aliquots from the first, second and third supernatants were analyzed for soluble protein and leghemoglobin, as described in Example 7. The results are shown in Table 10.

TABLE 10

Efficacy of alkaline buffer extraction on whole soybean powders (average from 6 samples) on the recovery of soluble protein and leghemoglobin protein. Methods for quantitation are provided in Example 5.

| Extraction # | % Soluble Protein Recovery | % Leghemoglobin Recovery |
|---|---|---|
| 1 | 97.2 | 100 |
| 2 | 2.8 | 0 |
| 3 | 0 | 0 |

The data show that all of the leghomoglobin protein was recovered in the first extraction.

Example 10: Enzymatic Soybean Processing (E-SOY) for Leghemoglobin Soybeans

A challenge for isolating proteins from soybean meals is the requirement for high water:solid ratios to yield a slurry that can be physically processed. This leads to large volumes of water in the process, which increase the processing costs associated with concentrating the extracted proteins, drying non-solubilized meal residues, and ultimately waste water disposal. A novel approach to isolating protein from defatted soybean meal was developed that uses food grade polysaccharide degrading enzymes to convert insoluble or viscous polysaccharide materials in the meal to solubilized, short chain polysaccharides, greatly reducing the volume of water required for protein extraction and isolation. This process used to isolate more traditional soybean protein concentrates and isolates, is expected to facilitate the isolation of leghemoglobin while maintaining the intact leghemoglobin complex. The generalized enzymatic soybean (E-SOY) process is outlined below.

Process Flow Chart

FIG. 12 shows an example of a generalized process flow chart for the E-SOY process. Laboratory defatted whole soybean meal (typically 40 g aliquots for the lab process) in a beaker was mixed with preheated water at a ratio 3:1 liquid:solid. After an incubation period, the beaker was placed on a regulated water bath, typically maintained at 50° C. An overhead stirrer (Lightnin Mixer) equipped with a low shear impeller was used to agitate the meal dough. The viscosity of the mixture was estimated by the stirrer power (watts) required to stir the dough at 200 rpm. With stirring an aliquot of 5N HCl was added dropwise to the dough (typically 4-5m Ls) to lower the pH of the slurry to a range of pH 3.8-4.5. The exact amount of acid required to lower the pH of different feedstocks was determined separately using feedstock suspended in a larger volume of water. Aliquots of the commercial enzymes (typically 200 μL of the cellulase, hemicellulase, and pectinase, 10 μL for liquid pectinase). The dough was then stirred and allowed to react with the enzymes for variable lengths of time, although 3 hours was routinely used. The power reading on the overhead mixer was recorded at intervals to monitor the viscosity of the dough slurry.

When the viscosity of the solution has been reduced sufficiently to form a free flowing slurry, the mixture was quantitatively transferred to a Buchner funnel fitted with a 500 uM mesh polypropylene screen and vacuum filtered. The filter cake was washed with 60 mLs of water. The filtrate solution was passed over a second Buchner funnel fitted with a 105 um mesh polypropylene screen and rinsed with deionized water from a wash bottle. The filter cakes from the 500 um and 105 um filtrations were quantitatively transferred to a tared container and dried in a vacuum oven at 65° C. for at least 48 hours. The dry weight of the combined filter cakes was determined, and the residue (Meal Residue) was ground in a coffee mill prior to further analysis.

The filtrate slurry from the 105 um filtration was adjusted to pH 6.5-7 with 2N NaOH, although for leghemoglobin isolation a pH of between 7 and 11 would be used. After stirring, the solution was transferred to centrifuge bottles and centrifuged at 7000 rpm for 10 minutes in a fixed angle rotor. The supernatant solution was carefully poured into a disposable 0.45 um-1L filter apparatus for filtration under vacuum. The centrifuge solids (concentrated precipitated protein concentrate, or CPPC) was suspended in deionized water, quantitatively transferred to a tared flask, and shell frozen and freeze dried. The recovered dry weight of CPPC was determined after freeze drying.

The 0.45 um filtered supernatant of soluble protein solution (SPS), was transferred to an ultrafiltration device equipped with a PES membrane module (Vivaflow 200, variable MWCO depending on the experiment). The SPS was concentrated down to a volume of ~50 mLs, then diafiltered with deionized water (100-300 mLs, depending on the experiment). The UF/DF permeate was collected in a flask for further processing. When the UF/DF step was completed, the retentate solution was quantitatively transferred to centrifuge bottles and centrifuged at 7000 rpm for 10 minutes to remove any precipitate that formed during the UF/DF process. The supernatant was decanted into a tared flask, shell frozen and lyophilized. The recovered solids (concentrated soluble protein isolate, or CSPI) was weighed and stored for further study. If any solids were recovered from the centrifugation step (soluble protein solution precipitate, or SPS-ppt), it was quantitatively transferred to another tared flask for freezing, freeze drying, and analysis.

In some variations of the UF/DF process, sequential UF/DF using a series of decreasing MWCO porosities was examined. The process was essentially the same, other than the permeate from the highest MWCO step was passed through the next lower MWCO membrane in series, and retentates were transferred to individual tared flasks to be frozen and lyophilized.

The final ultrafiltration permeate was concentrated on a rotary evaporator to dryness in a tared round bottom flask. The flask was transferred to a vacuum oven and further dried at 65° C. for at least 48 hours. The solids dry weight was determined, and the material scraped from the flask wall and transferred to a container for storage.

Protein was determined as total nitrogen using a combustion analyzer (CE Elantech, Flash EA 1112 series). Total nitrogen contents were converted to total protein by multiplying % N×6.25.

The recovery of protein from commercial soybean meal is shown in Table 11.

TABLE 11

Recovery of Products from Commercial Soybean Meal.

| Soybean Meal 50.9% Initial Protein Content | Product Yield (g/100 g) | Protein Yield (g/100 g) | Product Purity (% Protein) | Protein (% Initial) |
|---|---|---|---|---|
| Meal Residue (MR) | 50.2 | 33.3 | 66.3 | 65 |
| Protein Concentrate | 5.8 | 3.6 | 62.2 | 7 |
| 10 kD retentate ppt | 0.4 | 0.3 | 79.8 | 1 |
| 10 kD retentate solubles | 4.0 | 4.1 | 102.5 | 8 |

TABLE 11-continued

Recovery of Products from Commercial Soybean Meal.

| Soybean Meal 50.9% Initial Protein Content | Product Yield (g/100 g) | Protein Yield (g/100 g) | Product Purity (% Protein) | Protein (% Initial) |
|---|---|---|---|---|
| UF Permeate | 25.9 | 2.5 | 9.5 | 5 |
| Concentrate + Isolate | | 7.7 | | |
| Initial Protein | | 15 | | |
| Concentrate/Isolate | | 0.88 | | |

Due to the different solubilities of soy proteins, and their low solubility below pH 6, the meal residue (MR) fraction of the extracted soy meal retained 65% of the starting protein, with a protein purity of 66.3%. This actually represents an enrichment of the soy meal from the original 50.9% protein content, meeting the criteria for a protein concentrate of >65%. A much lower percentage of the initial protein was recovered in the concentrate and isolate fractions, recovering only 15% on the initial protein in these products. The concentrate fraction was actually lower in protein content than the meal residue (62.2% vs. 66.3%). The purity of the isolate fraction was excellent at 102.5%, and relatively low levels of protein was found in the UF permeate. The recovery of total protein was compromised by physical difficulties in separating the meal residue from the filter screen. Given the high protein content of the solids fraction, it might be more efficient to utilize a different physical separation of the solids from the dissolved protein of the digested meal slurry.

An unexpected finding was that the isolate protein could be recovered using a much higher MWCO ultrafiltration membrane than would have been predicted based on the molecular weight of the protein fraction. Due to an unexpected aggregated behavior in solution, much higher MWCO membranes could be used effectively. It is expected that a similar recovery is achieved for isolates produced from leghemoglobin-containing soybean. The use of higher flux membranes in the process will reduce the total surface area required, thus saving capital costs.

Steps are taken to preferentially extract the highly soluble leghemoglobin protein complex into the supernatant during the initial phases of the process and to allow its differential purification during the ultrafiltration step. This will produce a high value coproduct that could be used for downstream product formulation The process has been tested and is generally applicable to the oilseed feedstock listed in Table 12.

TABLE 12

| Oilseed Meals Tested with the E-SOY Process |
|---|
| Yellow Seed Coat Canola |
| High Oleic Canola (Nexera 845) |
| Conventional Canola |
| Field Mustard (*Brassica rapa*) |
| Indian Mustard (*Brassica juncea*) |
| Yellow Mustard (*Brassica hirtu*) |
| Commercial Sunflower (defatted meal, presscake, meats) |
| Safflower |
| Flaxseed |
| Sesame |

Additional protein yield improvements are realized by optimizing the defatting and desolventizing processes to minimize the irreversible denaturation of protein and leghemoglobin complex in the meal matrix. Additionally, the E-Soy processing scheme can be optimized for soybeans that have been created by proteome rebalancing (such as shown Example 6) to further enhance the potential recovery of protein from the meal. Further modifications of the E-Soy process to optimize protein extractions of meals derived from high oleic oil soybeans engineered to express the leghemoglobin protein (such as shown in Example 8) are also expected to lead to improved sensory and processing properties as well. For example, see U.S. Pat. No. 9,918,485, incorporated herein by reference, for examples of suitable soybean isolates to be used as feedstock and soy processing advantages associated with high oleic soybeans.

Example 11: Soybean Seeds Expressing Leghemoglobin in Combination with Reduced Antinutritional Factors and/or Increased Protein Content Many post-harvest processing steps which concentrate soybean protein for its subsequent incorporation into food products remove or inactivate antinutritional factors, such as protein based factors (e.g. the protease inhibitors) and carbohydrate based factors (e.g. raffino-oligosaccharides). Such steps may de-hemelate the leghemoglobin complexed protein, making it unsuitable for downstream use.

Genome editing techniques are used to reduce or knock out the expression of one or more of the Kunitz Trypsin and Bowman-Burke protease inhibitors and/or to inhibit the synthesis of one or more of raffinose and stachyose. These soybean seeds are also edited to express increased leghemoglobin or complexed leghemoglobin as described in the earlier examples. Alternatively, edited soybeans expressing increased leghemoglobin or complexed leghemoglobin are crossed with soybeans which have been edited to reduce or knock out expression of the Kunitz Trypsin protease inhibitors and Bowman-Burke protease inhibitors and/or to inhibit the synthesis of raffinose and stachyose, to create breeding stacks of the edited genes. Genome editing was used to reduce insoluble carbohydrate, such as raffinose and stachyose, by knockout of the raffinose synthase genes, such as RS2, RS3, RS4. Assays to determine the effectiveness of the engineering approaches will measure residual trypsin inhibitor activity using American Oil Chemists Society method Ba 12-75. Changes in the soluble carbohydrate profiles will be determined using the methods such as outlined in US Patent Publication No. 20190383733, which is incorporated herein by reference.

Genome editing was also used to increase total protein content in seeds by knockout or modification of key regulatory genes, such as CCT-domain containing proteins, reticulon, trehalose phosphate synthase, HECT Ubiquitin Ligase (HEL or UPL3) and/or MFT (mother of flowering time) mutated or modified plants and seeds such as disclosed in PCT/US2019/058747 incorporated herein by reference. Expression of leghemoglobin in soybeans engineered to optimize their processability as described in this example would add to the value and utility of such soybeans.

Engineering soybeans to minimize post-harvest processing steps is expected to result in greater yields of intact leghemoglobin complex. Such soybean seeds are processed without the need to use solvents to remove oil or a toasting step often employed in soybean processing. Such soybean seeds are processed using one or more of cold pressing, extrusion or Super Critical Fluid Extraction ((Friedrich J. P., List G. R., and Heakin A. J., 1982. Journal of the American Oil Chemists Society. 59 (7); 288-292).

Example 12. Transformation of the Nuclear Genomes for Seed Specific Expression of PPR10 Variants Mature dry seed from soybean lines are surface-sterilized for 16 hours using chlorine gas, produced by mixing 3.5 mL of 12 N HC1 with 100 mL of commercial bleach (5.25% sodium hypochloride), as described by Di et al. ((1996) Plant Cell Rep 15:746-750). Disinfected seeds are soaked in sterile distilled water at room temperature for 16 hours (100 seeds in a 25×100 mm petri dish) and imbibed on semi-solid medium containing 5 g/l sucrose and 6 g/l agar at room temperature in the dark. After overnight incubation, the seeds are soaked in distilled water for an additional 3-4 hours at room temperature in the dark. Intact embryonic axes (EA) are isolated from imbibed seeds. *Agrobacterium*-mediated EA transformation is carried out as described below.

A volume of 15 mL of *A. tumefaciens* LBA4404 or AGL-1 suspension harboring soybean nuclear transformation binary vector (FIG. 1) (OD 0.5 at 600 nm) in infection medium composed of 1/10× Gamborg B5 basal medium, 30 g/L sucrose, 20 mM MES, 0.25 mg/L GA3, 1.67 mg/L BAP, 200 μM acetosyringone and 1 mM dithiothreitol in pH 5.4 is added to about 200-300 EAs, and they are on a 25×100 mm deep petri dish. The plates are sealed with parafilm (Cat No. 52858, "Parafilm M" VWR), then sonicated (Sonicator-VWR model 50T) for 30 seconds. After sonication, EAs are incubated 2 hrs at room temperature. After inoculation, excess bacterial suspension is removed and about 200-300 EAs are transferred to a single layer of autoclaved sterile filter paper (Cat No. 28320-020, VWR) in 25×100 mm petri dish. The plates are sealed with Micropore tape (Cat No. 1530-0, 3M, St. Paul, Minn., USA) and incubated under dim light (1-2 $\mu E/m^2/s$), cool white fluorescent lamps for 16 hours at 21° C. for 3 days. After co-cultivation, the base of each embryonic axis is embedded in shoot induction medium (R7100, PhytoTech Labs) containing 30 g/L sucrose, 6 g/L agar and 25 mg/L spectinomycin (S742, PhytoTech Labs) as a selectable agent and 300 mg/L cefotaxime (GoldBio, ST Louis, Mo., USA) in pH5.7. Shoot induction is carried out in a Percival Biological Incubator (Percival Scientific, Perry, Iowa, USA) or growth room at 26° C. with a photoperiod of 16 hours and a light intensity of 60-100 $\mu E/m^2/s$. After 4-6 weeks in selection medium, the spectinomycin-resistant shoots are cut and transferred to ½ strength MS rooting medium (M404, PhytoTech Labs) containing 15 g/L sucrose, agar 6 g/L, 10 mg/L spectinomycin and 250 mg/L cefotaxime for further shoot and root elongations. Transformation efficiency are calculated based on the number of positive transgenic soybean T0 plants divided by the total number of EAs.

For heat shock treatment of soybean to produce spectinomycin marker gene free T0 events, 2-4 cm T0 plantlets with roots in 100×25 mm Petri dishes or magenta boxes on spectinomycin free-rooting medium are transferred into a Percival incubator (Percival Scientific, Perry, Iowa, USA) at 45° C., 70% humidity for 2 hrs in the dark. Non-heat shock treated T0 plantlets are used as a control. After the heat shock treatment, T0 plantlets are transferred to moistened Berger BM2 soil (Berger, Saint-Modeste, QC, Canada), and kept enclosed in clear plastic tray boxes in a Percival incubator at 26° C. with a 16 hr photoperiod at 250-350 $\mu E/m^2/s$. 2-4 leaf punch samples are collected for qPCR and SbS analyses from newer growth 2 weeks after acclimatization of T0 events.

FIG. 13 is a schematic diagram showing a soybean nuclear transformation binary vector within the T-DNA. In FIG. 13, RB and LB are right border and left border of the T-DNA respectively, GM-GY1 Pro is the soybean glycinin seed specific promoter, AtUBQ10Pro is the *Arabidopsis* ubiquitin 10 promoter, PPR10GG is a maize or soybean RNA-binding protein PPR10 variant, UBQ10TERM is an *Arabidopsis* ubiquitin 10 terminator, LoxP is the lox recombination-site, Gm-HSP17.3BPro is the soybean heat shock hs6871 promoter, MoCre is the Cre recombinase, SB-GKAFTerm is the *Sorghum bicolor* gamma kafirin storage protein terminator, At-UBQ10 Pro is the *Arabidopsis* ubiquitin 10 promoter, SpcN is the soybean codon optimized spectinomycin resistant gene from *Streptomyces spectabilis* Genebank protein ID AAD50455, and UBQ14Term is the *Arabidopsis* ubiquitin 14 terminator.

Example 13. Seed Specific Leghemoglobin Expression in Transplastomic Soybean Plants: Biolistic-Mediated Soybean Chloroplast Transformation Marker-free T1 homozygous line harboring GM-GY1 Pro:PPR10GG:SB-GAKF TERM expression cassettes are used as donor material for chloroplast transformation. Immature pods are collected from soybean marker-free T1-2 homozygous line and opened to retrieve immature seeds of about 2-8 mm in length. Immature seeds are collected and surface sterilized in a 50 mL screw cap tube containing 50 mL of a 10% bleach, 0.02% Tween-20 solution, with slight agitation for 15 minutes and are then rinsed 10 times with a total of 500 mL of sterile distilled water. Surface sterilized seeds are cut open under a microscope or under magnification. Typically, each immature seed's embryonic axis is cut off, and the two cotyledon pieces are released. Immature cotyledons are collected and transferred to flasks containing liquid S30 medium (Table 13).

TABLE 13

| Composition of media | | | | |
|---|---|---|---|---|
| | M2 | S30 | M7 | M8 |
| MS salt with B5 vitamins (PhytoTech M404) | | | 4.44 g/L | |
| Gamborg B-5 basal medium (PhytoTech G398) | | | | 3.21 g/L |
| Modified MS salt (PhytoTech M571) | 2.68 g/L | 2.68 g/L | | |
| B5 vitamins (1000X) (PhytoTech G249) | 1 ml | 1 ml | | |
| 2,4-D stock 10 mg/ml | 4 ml | 1 ml | | |
| $KNO_3$ | 0.93 g/L | 0.93 g/L | | |
| $(NH_4)_2SO_4$ | 0.463 g/L | 0.463 g/L | | |
| Asparagine | 1 g/L | 1 g/L | | |
| Glutamine | | 4.48 g/L | | |
| L-Methionine | | 0.149 g/L | | |
| Sucrose | 10 g/L | 10 g/L | | 10 g/L |
| Maltose | | | 60 g/L | |
| $MgCl_2 \cdot 6H_2O$ | | | 0.75 g/L | |
| Activated charcoal (PhytoTech C325) | | | 5 g/L | |
| pH | 5.8 | 5.8 | 5.7 | 5.7 |
| TC agar | 5 g/L | | | 5 g/L |
| Gelrite (Plant Media Cat# 714246) | | | 2 g/L | |

Immature cotyledons are pre-cultured in S30 medium for 10 days and targeted for direct biolistic-mediated DNA transformation. After 10 days of pre-culture, twenty (20) immature cotyledons are placed on the surface of M2 solid medium supplemented with 40 mg/L of 2,4-D in the center of small petri plates (60×15 mm) for bombardment. The immature cotyledons are bombarded with the 0.6 pm gold particle/plasmid DNA (FIG. 2) mixture at a concentration of 30 picogram/basepair/shot at 650 psi, 28 mm Hg with biolistic gene gun (PDS 1000/He, Bio-Rad). After 2 days of co-cultivation in the M2 solid medium, the bombarded immature cotyledons are transferred to liquid S30 medium containing 300 mg/L spectinomycin. Fresh S30 medium containing 300 mg/L spectinomycin is replaced bi-weekly. After 8-12 weeks of selection, spectinomycin resistant yellow green to green calli is emerged from the surface of explants. Putative transformed green callus is isolated under a microscope and plated onto petri plates with sterile filter paper overlaying M7 agar medium. The petri plates are sealed with Micropore™ surgical tape (3M Health Care, St. Paul, Minn., USA) and incubated at 26° C. with an 18-hour photoperiod at 35-60 μE/m2/s light intensity. After 3-4 weeks of maturation on M7 medium, mature somatic embryos are placed in sterile, Petri dishes and either sealed with Micropore™ surgical tape or placed unsealed in a plastic box for 4-7 days at room temperature for somatic embryo desiccation. After 4-7 days, desiccated embryos are plated onto M8 medium supplemented with 10 pg/L spectinomycin and were allowed to germinate at 26° C. with an 18-hour photoperiod at 35-60 μE/m2/s light intensity. After 4-6 weeks on M8 germination medium, plantlets are transferred to 3 inches pots containing moistened Berger BM2 soil (Berger Peat Moss, Saint-Modeste, Canada) and kept enclosed in clear plastic tray boxes until acclimatized in a culture room with a 16-hour photoperiod at 90-150 μE/m2/sand 26° C. day/24° C. night temperatures. After acclimation, hardened plantlets are potted in 2 gallon pots containing moistened Berger MB1 (Berger Peat Moss, Saint-Modeste, Canada) and grown in a greenhouse to seed-bearing maturity.

FIG. 14 is a schematic diagram of soybean chloroplast transformation vector. GM-TRNV is the soybean plastid TRNV homology region, NT-PSBA Pro is the tobacco PSBA plastid promoter, AADA is the spectinomycin adenylyltransferase gene, NT-PSBA 3UTR is the tobacco PSBA 3UTR, DicisGG is the GG binding site into the intergenic region of a dicistronic operon (SEQ ID NO: 44), Leghemoglobin is the soybean leghemoglobin coding sequence (Glyma.20g191200), GM-RPS is the soybean plastid RPS homology region.

It is expected that the soybean seeds express leghemoglobin in the plastids of the seeds, with minimal or no expression of leghemoglobin in non-seed parts of the plant, such as roots, stems, leaves and flowers.

Example 14. Seed Specific Leghemoglobin Expression in Transplastomic Soybean Plants: Plastid Transformation Followed by Nuclear Transformation The methodology of Example 13 is followed, except the starting donor material is a null or non-transformed soybean. The resulting soybean seeds and plants containing the transformed plastids are then transformed according to the method described in Example 12. It is expected that the soybean seeds express leghemoglobin in the plastids of the seeds, with minimal or no expression of leghemoglobin in non-seed parts of the plant, such as roots, stems, leaves and flowers.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

We claim:

1. A soybean seed comprising a leghemoglobin protein in an amount of at least 0.5% of total protein in the soybean seed and a genomic modification, wherein the genomic modification comprises an insertion of a leghemoglobin coding sequence into a native seed storage protein gene encoding a protein selected from the group consisting of: a glycinin, a conglycinin, a 2S albumin, a Kunitz trypsin inhibitor (KTI), a Bowman-Birk inhibitor (BBI), or a combination thereof.

2. The soybean seed of claim 1, wherein the native seed protein gene encodes a glycinin.

3. The soybean seed of claim 1, wherein the native seed protein gene encodes a conglycinin.

4. The soybean seed of claim 1, wherein the native seed protein gene encodes a Kunitz trypsin inhibitor (KTI).

5. The soybean seed of claim 1, wherein the leghemoglobin coding sequence replaces all of the native seed storage protein gene coding sequence.

6. The soybean seed of claim 1, wherein the soybean seed further comprises a characteristic selected from the group consisting of: (i) an oleic acid content of at least 50% of the total seed fatty acids; (ii) a linolenic acid content of less than 3% of the total seed fatty acids; (iii) a protein content of at least 37% of the total weight of the soybean measured at or adjusted to 13% moisture, and (iv) any combination thereof.

7. A plant which produces the soybean seed of claim 1.

8. The soybean seed of claim 1, wherein the leghemoglobin protein is expressed in an amount sufficient to impart a pink color to the soybean seed in a transverse section of the seed.

9. The soybean seed of claim 1, wherein the leghemoglobin coding sequence (i) encodes a polypeptide having at least 95% identity to SEQ ID NO: 2 or (ii) has at least 95% identity to SEQ ID NO: 1.

10. The soybean seed of claim 1, wherein the soybean seed further comprises an oleic add content of at least 50% of the total seed fatty adds.

11. The soybean seed of claim 1, wherein the soybean seed further comprises a recombinant construct integrated into its genome, the recombinant construct comprising a leghemoglobin coding sequence.

12. The soybean seed of claim 1, wherein the soybean seed comprises at least 37% protein by weight when measured or adjusted to 13% moisture.

13. The soybean seed of claim 1, wherein the soybean seed further comprises a modification to enhance seed protein content, the modification being in a gene encoding at least one of (i) a CCT-domain containing protein, (ii) a reticulon, (iii) a trehalose phosphate synthase, (iv) a HECT ubiquitin Ligase, (v) a MFT (mother of flowering) polypeptide, and (vi) a raffinose synthase.

14. A plant which produces the soybean seed of claim 12.

15. Meal extracted from the soybean seed of claim 1, wherein the meal comprises at least 0.1% leghemoglobin by weight of total protein.

16. The soybean seed of claim 1, wherein the leghemoglobin protein is expressed in an amount of at least 1% of the total seed protein.

17. The soybean seed of claim 1, wherein the leghemoglobin protein is expressed in an amount of at least 2% of the total seed protein.

18. A soybean seed comprising a genomic modification, the genomic modification comprising an insertion of a leghemoglobin coding sequence encoding a leghemoglobin protein into a native seed storage protein gene encoding a protein selected from the group consisting of a glycinin, conglycinin, 2S albumin, Kunitz trypsin inhibitor (KTI), a Bowman-Birk inhibitor (BBI), or a combination thereof such that the leghemoglobin coding sequence replaces all or part of the native storage protein gene coding sequence, and wherein the leghemoglobin protein is expressed in the soybean seed in an amount sufficient to impart a pink color to the soybean seed in a transverse section of the seed.

19. The soybean seed of claim 18, wherein the leghemoglobin protein is expressed in an amount of at least 1.5% of the total seed protein.

* * * * *

SEQUENCE LISTING

```
<160> NUMBER OF SEQ ID NOS: 48

<210> SEQ ID NO 1
<211> LENGTH: 438
<212> TYPE: DNA
<213> ORGANISM: Glycine Max

<400> SEQUENCE: 1

atgggtgctt tcactgagaa gcaagaggct ttggtgagta gctcattcga agcattcaag      60

gcaaacattc ctcaatacag cgttgtgttc tacacttcga tactggagaa agcacccgca     120

gcaaaggact tgttctcgtt tctatctaat ggagtagatc ctagtaatcc taagctcacg     180
```

```
ggccatgctg aaaagctttt tggattggtg cgtgactcag ctggtcaact taaagcaaat    240

ggaacagtag tggctgatgc cgcacttggt tctatccatg cccaaaaagc aatcactgat    300

cctcagttcg tggtggttaa agaagcactg ctgaaaacaa taaaggaggc agttggggac    360

aaatggagtg atgaattgag cagtgcttgg gaagtagcct atgatgaatt ggcagcagct    420

attaagaagg cattttag                                                  438
```

<210> SEQ ID NO 2
<211> LENGTH: 145
<212> TYPE: PRT
<213> ORGANISM: Glycine Max

<400> SEQUENCE: 2

```
Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
            20                  25                  30

Ser Ile Leu Glu Lys Ala Pro Ala Ala Lys Asp Leu Phe Ser Phe Leu
        35                  40                  45

Ser Asn Gly Val Asp Pro Ser Asn Pro Lys Leu Thr Gly His Ala Glu
    50                  55                  60

Lys Leu Phe Gly Leu Val Arg Asp Ser Ala Gly Gln Leu Lys Ala Asn
65                  70                  75                  80

Gly Thr Val Val Ala Asp Ala Ala Leu Gly Ser Ile His Ala Gln Lys
                85                  90                  95

Ala Ile Thr Asp Pro Gln Phe Val Val Val Lys Glu Ala Leu Leu Lys
            100                 105                 110

Thr Ile Lys Glu Ala Val Gly Asp Lys Trp Ser Asp Glu Leu Ser Ser
        115                 120                 125

Ala Trp Glu Val Ala Tyr Asp Glu Leu Ala Ala Ala Ile Lys Lys Ala
    130                 135                 140

Phe
145
```

<210> SEQ ID NO 3
<211> LENGTH: 633
<212> TYPE: DNA
<213> ORGANISM: Glycine Max

<400> SEQUENCE: 3

```
atgatgagag cgcggttccc attactgttg ctgggagttg ttttcctagc atcagtttct     60

gtctcatttg gcattgcgta ttgggaaaag cagaacccca gtcacaacaa gtgcctccga    120

agttgcaata gcgagaaaga ctcctacagg aaccaagcat gccacgctcg ttgcaacctc    180

cttaaggtgg aggaaatggg tgctttcact gagaagcaag aggctttggt gagtagctca    240

ttcgaagcat tcaaggcaaa cattcctcaa tacagcgttg tgttctacac ttcgatactg    300

gagaaagcac ccgcagcaaa ggacttgttc tcgtttctat ctaatggagt agatcctagt    360

aatcctaagc tcacgggcca tgctgaaaag ctttttggat tggtgcgtga ctcagctggt    420

caacttaaag caaatggaac agtagtggct gatgccgcac ttggttctat ccatgcccaa    480

aaagcaatca ctgatcctca gttcgtggtg gttaaagaag cactgctgaa aacaataaag    540

gaggcagttg gggacaaatg gagtgatgaa ttgagcagtg cttgggaagt agcctatgat    600

gaattggcag cagctattaa gaaggcattt tag                                 633
```

<210> SEQ ID NO 4
<211> LENGTH: 210
<212> TYPE: PRT
<213> ORGANISM: Glycine Max

<400> SEQUENCE: 4

```
Met Met Arg Ala Arg Phe Pro Leu Leu Leu Leu Gly Val Val Phe Leu
1               5                   10                  15

Ala Ser Val Ser Val Ser Phe Gly Ile Ala Tyr Trp Glu Lys Gln Asn
            20                  25                  30

Pro Ser His Asn Lys Cys Leu Arg Ser Cys Asn Ser Glu Lys Asp Ser
        35                  40                  45

Tyr Arg Asn Gln Ala Cys His Ala Arg Cys Asn Leu Leu Lys Val Glu
    50                  55                  60

Glu Met Gly Ala Phe Thr Glu Lys Gln Glu Ala Leu Val Ser Ser Ser
65                  70                  75                  80

Phe Glu Ala Phe Lys Ala Asn Ile Pro Gln Tyr Ser Val Val Phe Tyr
                85                  90                  95

Thr Ser Ile Leu Glu Lys Ala Pro Ala Ala Lys Asp Leu Phe Ser Phe
            100                 105                 110

Leu Ser Asn Gly Val Asp Pro Ser Asn Pro Lys Leu Thr Gly His Ala
        115                 120                 125

Glu Lys Leu Phe Gly Leu Val Arg Asp Ser Ala Gly Gln Leu Lys Ala
    130                 135                 140

Asn Gly Thr Val Val Ala Asp Ala Ala Leu Gly Ser Ile His Ala Gln
145                 150                 155                 160

Lys Ala Ile Thr Asp Pro Gln Phe Val Val Val Lys Glu Ala Leu Leu
                165                 170                 175

Lys Thr Ile Lys Glu Ala Val Gly Asp Lys Trp Ser Asp Glu Leu Ser
            180                 185                 190

Ser Ala Trp Glu Val Ala Tyr Asp Glu Leu Ala Ala Ala Ile Lys Lys
        195                 200                 205

Ala Phe
    210
```

<210> SEQ ID NO 5
<211> LENGTH: 543
<212> TYPE: DNA
<213> ORGANISM: Glycine Max

<400> SEQUENCE: 5

```
atggctactt caaagttgaa aacccagaat gtggttgtat ctctctccct aaccttaacc      60

ttggtactgg tgctactgac cagcaaggca aactcagcgg aaactatggg tgctttcact     120

gagaagcaag aggctttggt gagtagctca ttcgaagcat tcaaggcaaa cattcctcaa     180

tacagcgttg tgttctacac ttcgatactg gagaaagcac ccgcagcaaa ggacttgttc     240

tcgtttctat ctaatggagt agatcctagt aatcctaagc tcacgggcca tgctgaaaag     300

ctttttggat tggtgcgtga ctcagctggt caacttaaag caaatggaac agtagtggct     360

gatgccgcac ttggttctat ccatgcccaa aaagcaatca ctgatcctca gttcgtggtg     420

gttaaagaag cactgctgaa aacaataaag gaggcagttg gggacaaatg gagtgatgaa     480

ttgagcagtg cttgggaagt agcctatgat gaattggcag cagctattaa gaaggcattt     540

tag                                                                   543
```

<210> SEQ ID NO 6

<211> LENGTH: 180
<212> TYPE: PRT
<213> ORGANISM: Glycine Max

<400> SEQUENCE: 6

```
Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Ala Glu Thr Met Gly Ala Phe Thr Glu Lys Gln Glu Ala Leu Val Ser
        35                  40                  45

Ser Ser Phe Glu Ala Phe Lys Ala Asn Ile Pro Gln Tyr Ser Val Val
    50                  55                  60

Phe Tyr Thr Ser Ile Leu Glu Lys Ala Pro Ala Ala Lys Asp Leu Phe
65                  70                  75                  80

Ser Phe Leu Ser Asn Gly Val Asp Pro Ser Asn Pro Lys Leu Thr Gly
                85                  90                  95

His Ala Glu Lys Leu Phe Gly Leu Val Arg Asp Ser Ala Gly Gln Leu
            100                 105                 110

Lys Ala Asn Gly Thr Val Val Ala Asp Ala Ala Leu Gly Ser Ile His
        115                 120                 125

Ala Gln Lys Ala Ile Thr Asp Pro Gln Phe Val Val Val Lys Glu Ala
    130                 135                 140

Leu Leu Lys Thr Ile Lys Glu Ala Val Gly Asp Lys Trp Ser Asp Glu
145                 150                 155                 160

Leu Ser Ser Ala Trp Glu Val Ala Tyr Asp Glu Leu Ala Ala Ala Ile
                165                 170                 175

Lys Lys Ala Phe
            180
```

<210> SEQ ID NO 7
<211> LENGTH: 1071
<212> TYPE: DNA
<213> ORGANISM: Glycine Max

<400> SEQUENCE: 7

```
atggccaagc tagtttttttc cctttgtttt ctgcttttca gtggctgctg cttcgctttc      60

agttccatgg gtgctttcac tgagaagcaa gaggctttgg tgagtagctc attcgaagca     120

ttcaaggcaa acattcctca atacagcgtt gtgttctaca cttcgatact ggagaaagca     180

cccgcagcaa aggacttgtt ctcgtttcta tctaatggag tagatcctag taatcctaag     240

ctcacgggcc atgctgaaaa gctttttgga ttggtgcgtg actcagctgg tcaacttaaa     300

gcaaatggaa cagtagtggc tgatgccgca cttggttcta tccatgccca aaaagcaatc     360

actgatcctc agttcgtggt ggttaaagaa gcactgctga aaacaataaa ggaggcagtt     420

ggggacaaat ggagtgatga attgagcagt gcttgggaag tagcctatga tgaattggca     480

gcagctatta agaaggcatt tagcagaaga aatggcattg acgagaccat atgcaccatg     540

agacttcgcc acaacattgg ccagacttca tcacctgaca tctacaaccc tcaagccggt     600

agcgtcacaa ccgccaccag ccttgacttc ccagccctct cgtggctcag actcagtgct     660

gagtttggat ctctccgcaa gaatgcaatg ttcgtgccac actacaacct gaacgcgaac     720

agcataatat acgcattgaa tggacgggca ttgatacaag tggtgaattg caacggtgag     780

agagtgtttg atggagagct gcaagaggga cgggtgctga tcgtgccaca aaactttgtg     840

gtggctgcaa gatcacagag tgacaacttc gagtatgtgt cattcaagac caatgataca     900
```

```
cccatgatcg gcactcttgc aggggcaaac tcattgttga acgcattacc agaggaagtg    960

attcagcaca ctttcaacct aaaaagccag caggccaggc agataaagaa caacaaccct   1020

ttcaagttcc tggttccacc tcaggagtct cagaagagag ctgtggctta g            1071


<210> SEQ ID NO 8
<211> LENGTH: 356
<212> TYPE: PRT
<213> ORGANISM: Glycine Max

<400> SEQUENCE: 8

Met Ala Lys Leu Val Phe Ser Leu Cys Phe Leu Leu Phe Ser Gly Cys
1               5                   10                  15

Cys Phe Ala Phe Ser Ser Met Gly Ala Phe Thr Glu Lys Gln Glu Ala
            20                  25                  30

Leu Val Ser Ser Ser Phe Glu Ala Phe Lys Ala Asn Ile Pro Gln Tyr
        35                  40                  45

Ser Val Val Phe Tyr Thr Ser Ile Leu Glu Lys Ala Pro Ala Ala Lys
    50                  55                  60

Asp Leu Phe Ser Phe Leu Ser Asn Gly Val Asp Pro Ser Asn Pro Lys
65                  70                  75                  80

Leu Thr Gly His Ala Glu Lys Leu Phe Gly Leu Val Arg Asp Ser Ala
                85                  90                  95

Gly Gln Leu Lys Ala Asn Gly Thr Val Val Ala Asp Ala Ala Leu Gly
            100                 105                 110

Ser Ile His Ala Gln Lys Ala Ile Thr Asp Pro Gln Phe Val Val Val
        115                 120                 125

Lys Glu Ala Leu Leu Lys Thr Ile Lys Glu Ala Val Gly Asp Lys Trp
    130                 135                 140

Ser Asp Glu Leu Ser Ser Ala Trp Glu Val Ala Tyr Asp Glu Leu Ala
145                 150                 155                 160

Ala Ala Ile Lys Lys Ala Phe Ser Arg Arg Asn Gly Ile Asp Glu Thr
                165                 170                 175

Ile Cys Thr Met Arg Leu Arg His Asn Ile Gly Gln Thr Ser Ser Pro
            180                 185                 190

Asp Ile Tyr Asn Pro Gln Ala Gly Ser Val Thr Thr Ala Thr Ser Leu
        195                 200                 205

Asp Phe Pro Ala Leu Ser Trp Leu Arg Leu Ser Ala Glu Phe Gly Ser
    210                 215                 220

Leu Arg Lys Asn Ala Met Phe Val Pro His Tyr Asn Leu Asn Ala Asn
225                 230                 235                 240

Ser Ile Ile Tyr Ala Leu Asn Gly Arg Ala Leu Ile Gln Val Val Asn
                245                 250                 255

Cys Asn Gly Glu Arg Val Phe Asp Gly Glu Leu Gln Glu Gly Arg Val
            260                 265                 270

Leu Ile Val Pro Gln Asn Phe Val Val Ala Ala Arg Ser Gln Ser Asp
        275                 280                 285

Asn Phe Glu Tyr Val Ser Phe Lys Thr Asn Asp Thr Pro Met Ile Gly
    290                 295                 300

Thr Leu Ala Gly Ala Asn Ser Leu Leu Asn Ala Leu Pro Glu Glu Val
305                 310                 315                 320

Ile Gln His Thr Phe Asn Leu Lys Ser Gln Gln Ala Arg Gln Ile Lys
                325                 330                 335

Asn Asn Asn Pro Phe Lys Phe Leu Val Pro Pro Gln Glu Ser Gln Lys
```

340 345 350

Arg Ala Val Ala
355

<210> SEQ ID NO 9
<211> LENGTH: 613
<212> TYPE: DNA
<213> ORGANISM: Glycine Max

<400> SEQUENCE: 9
tttgatccat gcccttcatt tgccgcttat taattaattt ggtaacagtc cgtactaatc 60
agttacttat ccttccccca tcataattaa tcttggtagt ctcgaatgcc acaacactga 120
ctagtctctt ggatcataag aaaaagccaa ggaacaaaag aagacaaaac acaatgagag 180
tatcctttgc atagcaatgt ctaagttcat aaaattcaaa caaaaacgca atcacacaca 240
gtggacatca cttatccact agctgatcag gatcgccgcg tcaagaaaaa aaaactggac 300
cccaaaagcc atgcacaaca acacgtactc acaaaggtgt caatcgagca gcccaaaaca 360
ttcaccaact caacccatca tgagccctca catttgttgt ttctaaccca acctcaaact 420
cgtattctct tccgccacct catttttgtt tatttcaaca cccgtcaaac tgcatgccac 480
cccgtggcca aatgtccatg catgttaaca agacctatga ctataaatag ctgcaatctc 540
ggcccaggtt ttcatcatca agaaccagtt caatatccta gtacaccgta ttaaagaatt 600
taagatatac tgc 613

<210> SEQ ID NO 10
<211> LENGTH: 1000
<212> TYPE: DNA
<213> ORGANISM: Glycine Max

<400> SEQUENCE: 10
aactcagcat ctattttttt tctctcaacc tttttcacat cttaagtagt ctgcaccctt 60
tatatatata acttatttct taccttttac attatgtaac ttttatcacc aaaaccaaca 120
actttaaatt tttattaaat agactccaca agtaacttga cactcttaca ttcatcgaca 180
ttaactttta tctgttttat aaatattatt gtgatataat ttaatcaaaa taaccacaaa 240
ctttcataaa aggttcttat taagcatggc atttaataag caaaaacaac tcaatcactt 300
tcatatagga ggtagcctaa gtacgtactc aaaatgtcaa caaataaaaa aaaagttgct 360
ttaataatgc caaaacaaat taataaaaca cttacaacac cggatttttt ttaattaaaa 420
tgtgccattt aggataaata gttaatattt ttaataatta tttaaaaagc cgtatctact 480
aaaatgattt ttatttggtt gaaaatgtta atatgtttaa atcaacacaa tctatcaaaa 540
ttaaactaaa aaaaaaataa gtgtacgtgg ttaacattag tacagtaata taagaggaaa 600
atgagaaatt aagaaattga aagcgagtct aatttataaa ttatgaacct gcatatataa 660
aaggaaagaa agaatccagg aagaaaagaa atgaaaccat gcatggtccc ctcgtcatca 720
cgagtttctg ccatttgcaa tagaaacact gaaacacctt tctctttgtc acttaattga 780
gatgccgaag ccacctcaca ccatgaactt catgaggtgt agcacccaag gcttccatag 840
ccatgcatac tgaagaatgt ctcaagctca gcaccctact tctgtgacgt gtccctcatt 900
caccttcctc tcttccctat aaataaccac gcctcaggtt ctccgcttca caacacaaac 960
attctctcca ttggtcctta aacactcatc agtcatcacc 1000

<210> SEQ ID NO 11

<211> LENGTH: 1620
<212> TYPE: DNA
<213> ORGANISM: Glycine Max

<400> SEQUENCE: 11

```
atggccgttt caaccacttt ctccggtgcc aaattggagg ctctattgct caaatgttct      60

tcctcctctt cctcaccacc gccttcaagg tcatcattca ccacttttcc cggccaaaac     120

agaagaaccc tcattcagag aggggttatt cgctgcgacg ctcagccctc tgatgcatca     180

tctgttgctc caaataatgc caccgctctc tccgctcttg agcagctcaa gacttctgca     240

gctgatagat atacaaagga aagaagcagc attatcgcca ttgggctcag tgtgcacact     300

gcacctgtgg aaatgcgtga aaaacttgcc attccagaag cagaatggcc tagagctatt     360

gcagagctgt gtagtctgaa tcatattgaa gaagcagctg ttctgagtac ctgcaatcga     420

atggagatat atgttcttgc cctgtcccaa catcgtggtg tcaaagaagt catggaatgg     480

atgtcaaaaa caagttctgt ccctgtttca gagcttagcc agcaccggtt tttactttac     540

aacaatgatg ccacacagca tctttttgaa gtatcagcag gtcttgactc tcttgttttg     600

ggggaaggtc aaatcctttc tcaggttaag caagttgtta aagttggaca aggagttaac     660

ggctttggga gaaatatcag tggctattc aagcatgcaa ttactgtcgg gaaaagggtt     720

agaactgaga ctaatattgc ttctggggca gtttctgtga gctcagctgc cgttgagttg     780

gcctatatga agttacctga agcctcacac gataatgcca ggatgttggt tattggtgct     840

ggcaagatgg gaaagcttgt gatcaaacat ttggtggcaa aaggttgcaa aaagatggtg     900

gttgtcaata gaactgagga gagagttgct gcaatacgtg aagaactgaa ggatattgag     960

attatctaca aaccccttc agaaatgctc acctgtgctg gcgaagcaga tttagttttc    1020

accagtactg catcagaaaa cccattattc ttgaaagaac atgtcaagga ccttcctcct    1080

gcaagtcaag aagttggagg ccgtcgcttt ttcattgata tctctgttcc ccggaatgtg    1140

ggttcatgtg tctcagacct tgagtctgtg cgagtttaca atgttgacga ccttaaagag    1200

gttgtggctg ccaataaaga ggatcgccta agaaaagcaa tggaagcaca ggcaatcatt    1260

gctgaagaat ctaagcaatt cgaagcttgg agggactcac tggaaactgt tcctactatt    1320

aagaaattga gggcttatgc tgaaagaatc aggcttgctg agcttgagaa gtgcttaggt    1380

aagatgggtg atgatatacc aaagaaaacg cggagagctg tggatgacct tagtcggggt    1440

atagtgaata agttgcttca tggtccaatg caacatttaa ggtgtgatgg gaacgacagc    1500

cggactctta gtgagacact ggagaacatg aatgctttga ataggatgtt caaccttgag    1560

acagaaatat ctgttttgga ggagaagatt cgagcaaagg tcgaacaaaa ccagaaatga    1620
```

<210> SEQ ID NO 12
<211> LENGTH: 539
<212> TYPE: PRT
<213> ORGANISM: Glycine Max

<400> SEQUENCE: 12

```
Met Ala Val Ser Thr Thr Phe Ser Gly Ala Lys Leu Glu Ala Leu Leu
1               5                   10                  15

Leu Lys Cys Ser Ser Ser Ser Ser Ser Pro Pro Pro Ser Arg Ser Ser
            20                  25                  30

Phe Thr Thr Phe Pro Gly Gln Asn Arg Arg Thr Leu Ile Gln Arg Gly
        35                  40                  45

Val Ile Arg Cys Asp Ala Gln Pro Ser Asp Ala Ser Ser Val Ala Pro
    50                  55                  60
```

```
Asn Asn Ala Thr Ala Leu Ser Ala Leu Glu Gln Leu Lys Thr Ser Ala
65                  70                  75                  80

Ala Asp Arg Tyr Thr Lys Glu Arg Ser Ser Ile Ile Ala Ile Gly Leu
                85                  90                  95

Ser Val His Thr Ala Pro Val Glu Met Arg Glu Lys Leu Ala Ile Pro
            100                 105                 110

Glu Ala Glu Trp Pro Arg Ala Ile Ala Glu Leu Cys Ser Leu Asn His
        115                 120                 125

Ile Glu Glu Ala Ala Val Leu Ser Thr Cys Asn Arg Met Glu Ile Tyr
    130                 135                 140

Val Leu Ala Leu Ser Gln His Arg Gly Val Lys Glu Val Met Glu Trp
145                 150                 155                 160

Met Ser Lys Thr Ser Ser Val Pro Val Ser Glu Leu Ser Gln His Arg
                165                 170                 175

Phe Leu Leu Tyr Asn Asn Asp Ala Thr Gln His Leu Phe Glu Val Ser
            180                 185                 190

Ala Gly Leu Asp Ser Leu Val Leu Gly Glu Gly Gln Ile Leu Ser Gln
        195                 200                 205

Val Lys Gln Val Val Lys Val Gly Gln Gly Val Asn Gly Phe Gly Arg
    210                 215                 220

Asn Ile Ser Gly Leu Phe Lys His Ala Ile Thr Val Gly Lys Arg Val
225                 230                 235                 240

Arg Thr Glu Thr Asn Ile Ala Ser Gly Ala Val Ser Val Ser Ser Ala
                245                 250                 255

Ala Val Glu Leu Ala Tyr Met Lys Leu Pro Glu Ala Ser His Asp Asn
            260                 265                 270

Ala Arg Met Leu Val Ile Gly Ala Gly Lys Met Gly Lys Leu Val Ile
        275                 280                 285

Lys His Leu Val Ala Lys Gly Cys Lys Lys Met Val Val Val Asn Arg
    290                 295                 300

Thr Glu Glu Arg Val Ala Ala Ile Arg Glu Glu Leu Lys Asp Ile Glu
305                 310                 315                 320

Ile Ile Tyr Lys Pro Leu Ser Glu Met Leu Thr Cys Ala Gly Glu Ala
                325                 330                 335

Asp Leu Val Phe Thr Ser Thr Ala Ser Glu Asn Pro Leu Phe Leu Lys
            340                 345                 350

Glu His Val Lys Asp Leu Pro Pro Ala Ser Gln Glu Val Gly Gly Arg
        355                 360                 365

Arg Phe Phe Ile Asp Ile Ser Val Pro Arg Asn Val Gly Ser Cys Val
    370                 375                 380

Ser Asp Leu Glu Ser Val Arg Val Tyr Asn Val Asp Asp Leu Lys Glu
385                 390                 395                 400

Val Val Ala Ala Asn Lys Glu Asp Arg Leu Arg Lys Ala Met Glu Ala
                405                 410                 415

Gln Ala Ile Ile Ala Glu Glu Ser Lys Gln Phe Glu Ala Trp Arg Asp
            420                 425                 430

Ser Leu Glu Thr Val Pro Thr Ile Lys Lys Leu Arg Ala Tyr Ala Glu
        435                 440                 445

Arg Ile Arg Leu Ala Glu Leu Glu Lys Cys Leu Gly Lys Met Gly Asp
    450                 455                 460

Asp Ile Pro Lys Lys Thr Arg Arg Ala Val Asp Asp Leu Ser Arg Gly
465                 470                 475                 480
```

```
Ile Val Asn Lys Leu Leu His Gly Pro Met Gln His Leu Arg Cys Asp
                485                 490                 495

Gly Asn Asp Ser Arg Thr Leu Ser Glu Thr Leu Glu Asn Met Asn Ala
            500                 505                 510

Leu Asn Arg Met Phe Asn Leu Glu Thr Glu Ile Ser Val Leu Glu Glu
        515                 520                 525

Lys Ile Arg Ala Lys Val Glu Gln Asn Gln Lys
    530                 535


<210> SEQ ID NO 13
<211> LENGTH: 1446
<212> TYPE: DNA
<213> ORGANISM: Glycine Max

<400> SEQUENCE: 13

atgaacgcaa cctcatactc tgctcttcct tctacgttcc gcagtctcca tcatcggaat     60

ttctcagcgt tttgttctga tatccaaaat cctggctatg ttgattgcca ttcaaattgt    120

aataagtcta catctcaagc gtctttgttt ttgtgttccg actccaacag tagaagaaat    180

ggtgtttttg gtagaccact ttgtgtgaac ccctctggca ggagaaacct agttggtcca    240

gctttttatt ctctggagac tagtgcttat gacgtggctg ctttagaatc tccttcccgt    300

gttgcagaag aaaaagttgg tgtgctgctt ctcaatctag gaggaccaga gacattgagt    360

gacgtgcaac cttttctgtt taatcttttt gcagatcctg atatcattcg tcttccaagg    420

ttgtttcggt ttctccagcg accattggca aaattgattt ctgtacttcg ggctcctaaa    480

tccaaggaag ggtatgctgc tattggtggt ggctctcctt tacgaaaaat tacagatgac    540

caggcacttg caattaaaat ggctttggaa gcaaagggca tctcttcaaa tgtctacgtt    600

gggatgcgat actggtaccc atttactgaa gaagcaattc agcaaattaa gagggacaga    660

ataacaaggc ttgtggtact acccctttat ccccagtttt ctatatccac aactggatca    720

agcatccgtg ttcttgagca tatattcagg gaagatgcct acttgtctaa gctccctgtt    780

tccattataa actcttggta tcaacgagaa ggttatatta agtcaatggc taacttaatt    840

cagaaagagc tccagagttt ttctgaacca aaagaggtaa tgatattttt cagtgcccat    900

ggtgtacctg tcagttacgt tgaggaagct ggggatccat accgagacca aatggaggag    960

tgcatcttct tgatcatgca agagttgaaa gctagaggaa ttagtaatga gcacactctt   1020

gcttatcaga gtcgagtggg tcctgtacag tggctgaaac catatactga tgaagttctc   1080

gttgagcttg gccaaaaagg tgtgaagagt cttttagctg ttccagtgag ttttgtgagt   1140

gagcatattg aaacccttga agaaattgac atggagtaca aggaattggc tcttgaatct   1200

ggcatcaaga attgggcacg tgtacctgcc cttggtgtta ccccttcctt cattacagat   1260

ttagcagatg cagtaataga agctctccca tcagcaacag caatatatgc accgaccaga   1320

acctctgaag atgttgatca tgacccagtt agatatttta tcaagatgtt ctttggttca   1380

atcttggcat tcatcttgtt cttgtcaccc aaaatgatca cggcattcag gaatcatgtc   1440

atttag                                                              1446


<210> SEQ ID NO 14
<211> LENGTH: 481
<212> TYPE: PRT
<213> ORGANISM: Glycine Max

<400> SEQUENCE: 14

Met Asn Ala Thr Ser Tyr Ser Ala Leu Pro Ser Thr Phe Arg Ser Leu
```

-continued

```
1               5                   10                  15

His His Arg Asn Phe Ser Ala Phe Cys Ser Asp Ile Gln Asn Pro Gly
            20                  25                  30

Tyr Val Asp Cys His Ser Asn Cys Asn Lys Ser Thr Ser Gln Ala Ser
        35                  40                  45

Leu Phe Leu Cys Ser Asp Ser Asn Ser Arg Arg Asn Gly Val Phe Gly
    50                  55                  60

Arg Pro Leu Cys Val Asn Pro Ser Gly Arg Arg Asn Leu Val Gly Pro
65                  70                  75                  80

Ala Phe Tyr Ser Leu Glu Thr Ser Ala Tyr Asp Val Ala Ala Leu Glu
                85                  90                  95

Ser Pro Ser Arg Val Ala Glu Glu Lys Val Gly Val Leu Leu Leu Asn
            100                 105                 110

Leu Gly Gly Pro Glu Thr Leu Ser Asp Val Gln Pro Phe Leu Phe Asn
        115                 120                 125

Leu Phe Ala Asp Pro Asp Ile Ile Arg Leu Pro Arg Leu Phe Arg Phe
    130                 135                 140

Leu Gln Arg Pro Leu Ala Lys Leu Ile Ser Val Leu Arg Ala Pro Lys
145                 150                 155                 160

Ser Lys Glu Gly Tyr Ala Ala Ile Gly Gly Gly Ser Pro Leu Arg Lys
                165                 170                 175

Ile Thr Asp Asp Gln Ala Leu Ala Ile Lys Met Ala Leu Glu Ala Lys
            180                 185                 190

Gly Ile Ser Ser Asn Val Tyr Val Gly Met Arg Tyr Trp Tyr Pro Phe
        195                 200                 205

Thr Glu Glu Ala Ile Gln Gln Ile Lys Arg Asp Arg Ile Thr Arg Leu
    210                 215                 220

Val Val Leu Pro Leu Tyr Pro Gln Phe Ser Ile Ser Thr Thr Gly Ser
225                 230                 235                 240

Ser Ile Arg Val Leu Glu His Ile Phe Arg Glu Asp Ala Tyr Leu Ser
                245                 250                 255

Lys Leu Pro Val Ser Ile Ile Asn Ser Trp Tyr Gln Arg Glu Gly Tyr
            260                 265                 270

Ile Lys Ser Met Ala Asn Leu Ile Gln Lys Glu Leu Gln Ser Phe Ser
        275                 280                 285

Glu Pro Lys Glu Val Met Ile Phe Phe Ser Ala His Gly Val Pro Val
    290                 295                 300

Ser Tyr Val Glu Glu Ala Gly Asp Pro Tyr Arg Asp Gln Met Glu Glu
305                 310                 315                 320

Cys Ile Phe Leu Ile Met Gln Glu Leu Lys Ala Arg Gly Ile Ser Asn
                325                 330                 335

Glu His Thr Leu Ala Tyr Gln Ser Arg Val Gly Pro Val Gln Trp Leu
            340                 345                 350

Lys Pro Tyr Thr Asp Glu Val Leu Val Glu Leu Gly Gln Lys Gly Val
        355                 360                 365

Lys Ser Leu Leu Ala Val Pro Val Ser Phe Val Ser Glu His Ile Glu
    370                 375                 380

Thr Leu Glu Glu Ile Asp Met Glu Tyr Lys Glu Leu Ala Leu Glu Ser
385                 390                 395                 400

Gly Ile Lys Asn Trp Ala Arg Val Pro Ala Leu Gly Val Thr Pro Ser
                405                 410                 415

Phe Ile Thr Asp Leu Ala Asp Ala Val Ile Glu Ala Leu Pro Ser Ala
            420                 425                 430
```

```
Thr Ala Ile Tyr Ala Pro Thr Arg Thr Ser Glu Asp Val Asp His Asp
        435                 440                 445

Pro Val Arg Tyr Phe Ile Lys Met Phe Phe Gly Ser Ile Leu Ala Phe
    450                 455                 460

Ile Leu Phe Leu Ser Pro Lys Met Ile Thr Ala Phe Arg Asn His Val
465                 470                 475                 480

Ile


<210> SEQ ID NO 15
<211> LENGTH: 505
<212> TYPE: DNA
<213> ORGANISM: Phaseolus vulgaris

<400> SEQUENCE: 15

agcttggcac tctgtggtct tttggttcat gcatggatgc ttgcgcaaga aaaagacaaa      60

gaacaaagaa aaaagacaaa acagagagac aaaacgcaat cacacaacca actcaaatta     120

gtcactggct gatcaagatc gccgcgtcca tgtatgtcta aatgccatgc aaagcaacac     180

gtgcttaaca tgcactttaa atggctcacc catctcaacc cacacacaaa cacattgcct     240

ttttcttcat catcaccaca accacctgta tatattcatt ctcttccgcc acctcaattt     300

cttcacttca acacacgtca acctgcatat gcgtgtcatc ccatgcccaa atctccatgc     360

atgttccaac caccttctct cttatataat acctataaat acctctaata tcactcactt     420

ctttcatcat ccatccatcc agagtactac tactctacta ctataatacc ccaacccaac     480

tcatattcaa tactactcta ctaac                                           505


<210> SEQ ID NO 16
<211> LENGTH: 993
<212> TYPE: DNA
<213> ORGANISM: Brassica napus

<400> SEQUENCE: 16

ctgcggatca agcagctttc atattaagca taccaaagcg taagatggtg gatgaaactc      60

aagagactct ccgcaccacc gcctttccaa gtactcatgt caaggttggt ttctttagct     120

ttgaacacag atttggatct ttttgttttg tttccatata cataggacct gagagctttt     180

ggttgaattt tttttttttc aggacaaatg ggcgaagaat ctgtacattg catcaatatg     240

ctatggcagg acagtgtgct gatgatacac acttaagcat catgtgttgt gttagaaagc     300

cgaagacaat tggagcgagc ctcagggtcg tcataatacc aatcaaagac gtaaaaccag     360

acgcagtctc tttggttgaa tgtgatgaaa gggatgtgtc ttggtatgta tgtacgagta     420

acaaaagaga agatgcaatt gagtagtaga aagatttgag agctttttaa agcccttcaa     480

gtgtgtgctt ttatcttatt gatatcatcc atttgcgttg tttaatgcgt ctttagatat     540

gtttctgttt ctttctcagt gtctgaatat ctgataagtg caatgtgaga aagccacacc     600

aaaccaaaat attcaaatct tatattttta ataatgtcga atcactcgga gttgccacct     660

tctgtgccaa ttgtgctgaa tctatcacac taaaaaaaac atttcttcaa ggtaatgact     720

tgtggactat gttctgaatt ctcattaagt ttttattttt tgaagtttaa gtttttacct     780

tctttttttga aaaatatcgt tcataagatg tcacgccagg acatgagcta cacatcacat     840

attagcatgc agatgcggac gatttgtcac tcacttcaaa cacctaaaag agcttctctc     900

tcacagcaca cacacatatg catgcaatat ttacacgtga tcgccatgca aatctccatt     960

ctcacctata aattagagcc tcggcttcac tct                                  993
```

<210> SEQ ID NO 17
<211> LENGTH: 19
<212> TYPE: DNA
<213> ORGANISM: Glycine Max

<400> SEQUENCE: 17
gtttgctgag gctgctctc 19

<210> SEQ ID NO 18
<211> LENGTH: 20
<212> TYPE: DNA
<213> ORGANISM: Glycine Max

<400> SEQUENCE: 18
gaaagcaaaa gcagaagaaa 20

<210> SEQ ID NO 19
<211> LENGTH: 20
<212> TYPE: DNA
<213> ORGANISM: Glycine Max

<400> SEQUENCE: 19
gtggggtagc acatacaaaa 20

<210> SEQ ID NO 20
<211> LENGTH: 4825
<212> TYPE: DNA
<213> ORGANISM: Glycine Max

<400> SEQUENCE: 20
aactcagcat ctattttttt tctctcaacc tttttcacat cttaagtagt ctgcaccctt 60
tatatatata acttatttct taccttttac attatgtaac ttttatcacc aaaaccaaca 120
actttaaatt tttattaaat agactccaca agtaacttga cactcttaca ttcatcgaca 180
ttaactttta tctgttttat aaatattatt gtgatataat ttaatcaaaa taaccacaaa 240
ctttcataaa aggttcttat taagcatggc atttaataag caaaaacaac tcaatcactt 300
tcatatagga ggtagcctaa gtacgtactc aaaatgtcaa caaataaaaa aaaagttgct 360
ttaataatgc caaaacaaat taataaaaca cttacaacac cggatttttt ttaattaaaa 420
tgtgccattt aggataaata gttaatattt ttaataatta tttaaaaagc cgtatctact 480
aaaatgattt ttatttggtt gaaaatgtta atatgtttaa atcaacacaa tctatcaaaa 540
ttaaactaaa aaaaaaataa gtgtacgtgg ttaacattag tacagtaata taagaggaaa 600
atgagaaatt aagaaattga aagcgagtct aatttataaa ttatgaacct gcatatataa 660
aaggaaagaa agaatccagg aagaaaagaa atgaaaccat gcatggtccc ctcgtcatca 720
cgagtttctg ccatttgcaa tagaaacact gaaacacctt tctctttgtc acttaattga 780
gatgccgaag ccacctcaca ccatgaactt catgaggtgt agcacccaag gcttccatag 840
ccatgcatac tgaagaatgt ctcaagctca gcaccctact tctgtgacgt gtccctcatt 900
caccttcctc tcttccctat aaataaccac gcctcaggtt ctccgcttca caacacaaac 960
attctctcca ttggtcctta aacactcatc agtcatcacc atggccaagc tagtttttc 1020 cctttgtttt ctgcttttca gtggctgctg cttcgctttc agttccagag agcagcctca 1080
gcaaaacgag tgccagatcc aaaaactcaa tgccctcaaa ccggataacc gtatagagtc 1140
agaaggtggg ttcattgaga catggaaccc taacaacaag ccattccagt gtgccggtgt 1200

```
tgccctctct cgctgcaccc tcaaccgcaa cgcccttcgt agaccttcct acaccaacgg   1260

tccccaggaa atctacatcc aacaaggtcc atcttgtcca aacttcacat ataaatatat   1320

aatagactta aatatgttta agggtttgat aaatgaggga attttatttt agatttttaa   1380

taatttcttt tttattttga gtttttatat attaaaattt ttgttttgat ttcttcaata   1440

tgacgtaaca taatcatatc attgataatg ttggattcct aattttttttg tttgtttgtt   1500

gttttgtaaa atgaataggt aagggtattt ttggcatgat atacccgggt tgtcctagca   1560

catttgaaga gcctcaacaa cctcaacaaa gaggacaaag cagcagacca caagaccgtc   1620

accagaagat ctataacttc agagagggtg atttgatcgc agtgcctact ggtgttgcat   1680

ggtggatgta caacaatgaa gacactcctg ttgttgccgt ttctattatt gacaccaaca   1740

gcttggagaa ccagctcgac cagatgccta gggtgagcca catagcaata ttagatatta   1800

taattcttta aaggtttaaa tatcatttta gttcgtggag ttgcactttc taatttagta   1860

cctatagatt aaaatatgcc aattggatcc ttatagttgt gttttttttat ccaatttggt   1920

tcttgtcttg aaataaatgg acaatattgt agctgataaa aaaaggaaac tggactacat   1980

tgtaacgtta agattagaat tcttaagttc taatactagc tggttacgga ttgacaacta   2040

tttgttttga caattcttgg cagagattct atcttgctgg gaaccaagag caagagtttc   2100

taaaatatca gcagcagcag caaggaggtt cccaaagcca gaaaggaaag catcagcaag   2160

aagaagaaaa cgaaggaggc agcatattga gtggcttcac cctggaattc ttggaacatg   2220

cattcagcgt ggacaagcag atagcgaaaa acctacaagg agagaacgaa ggggaagaca   2280

agggagccat tgtgacagtg aaaggaggtc tgagcgtgat aaaaccaccc acggacgagc   2340

agcaacaaag accccaggaa gaggaagaag aagaagagga tgagaagcca cagtgcaagg   2400

gtaaagacaa acactgccaa cgcccccgag gaagccaaag caaaagcaga agaaatggca   2460

ttgacgagac catatgcacc atgagacttc gccacaacat tggccagact tcatcacctg   2520

acatctacaa ccctcaagcc ggtagcgtca caaccgccac cagccttgac ttcccagccc   2580

tctcgtggct cagactcagt gctgagtttg gatctctccg caaggtacgt acatcattca   2640

tcaaagatca acatacattt atacattaaa ctaatatttg tttccaaata tttattaatt   2700

ttattgataa ttaatttttt tagaaaattt gtttgatcac ttttaatgga gtctttcatc   2760

ttaattacat tatttatact tacactaatg atttgttgat taataataat cttagataca   2820

ctataaaatg tgtgacggag ttatcttaac acttgcatgg attctatctt ttctgtcttt   2880

atatatagaa atagagagaa aaaaagaaga aaagattgat gaaaaaagca aaacaaaaaa   2940

tagtattatt ataaaaatat tggatgaatt tgttgtgact cttgcatgca ttgatgtacg   3000

atgcagaatg caatgttcgt gccacactac aacctgaacg cgaacagcat aatatacgca   3060

ttgaatggac gggcattgat acaagtggtg aattgcaacg gtgagagagt gtttgatgga   3120

gagctgcaag agggacgggt gctgatcgtg ccacaaaact ttgtggtggc tgcaagatca   3180

cagagtgaca acttcgagta tgtgtcattc aagaccaatg atacacccat gatcggcact   3240

cttgcagggg caaactcatt gttgaacgca ttaccagagg aagtgattca gcacactttc   3300

aacctaaaaa gccagcaggc caggcagata aagaacaaca accctttcaa gttcctggtt   3360

ccacctcagg agtctcagaa gagagctgtg gcttagagcc ctttttgtat gtgctacccc   3420

acttttgtct ttttggcaat agtgctagca accaataaat aataataata ataatgaata   3480

agaaaacaaa ggctttagct tgccttttgt tcactgtaaa ataataatgt aagtactctc   3540

tataatgagt cacgaaactt ttgcgggaat aaaaggagaa attccaatga gttttctgtc   3600
```

```
aaatcttctt ctgtctctct ctctctctct ttttttttcc tttcttctga gcttcttgca   3660

aaacaaaagg caaacaataa cgattggtcc aatgatagtt agcttaatcg atgatatctt   3720

taggaagtgt tggcaggaca ggacatgatg tagaagacta aaattgaaag tattgcagac   3780

ccaatagttg aagattaact ttaagaatta agacgtctgt taggaagaag ccattgcaac   3840

caataaagca tagtagatag ttagttaaat ctgttgggtt agttaccaac aagttgttaa   3900

tactgttgag ttagttatgc atgtaaataa ttgtagtata taagagttgc agtaatgaat   3960

aaaagacatg cagaaaaact tagaatcagt ttagttgtta tggagagggt gagatagtgc   4020

ctttgttcga ggcaaggctc ctcctaagaa agtctgaaac tgattttaaa cttttctgca   4080

tggcttttat tcattattgc aactcttata tactacaatt atttacatgc ataactaact   4140

caacaaacta atggtattaa caacttgttg gtaactaacc caacagattt aactaactat   4200

ctactatgct ttattggttg caatggcttc ttcctaacaa cgtcttatca ggttcttcat   4260

gacttggagc tcaacccaac ttggaaagtt cgagagtatt tggaccattg tgctttgtgt   4320

cttcaaacat aaaacatcgc tccaaattta acatgggagc taaaaaatgt gtttttctgg   4380

gattttaatt ttcaacagag tcaaggatgg tgttgcatat gatgtcttga tgtccattgt   4440

ccacactaaa tagatattgg tttcaagaaa tattaatttc attttcatga ctttcaattc   4500

ataaacctta aacgaatatt aatttaaaat ctatcctcaa atgataaatt taaaaaaaaa   4560

ttacccccaa tcggtaattt gactcacaag ttagttagtt gatattttga agcttgaaat   4620

tcgacatgga catcagacac aatatgagca cagacactct cgcatagcta atgtgtaaaa   4680

catagaatga caggacatca catatatttt tacacacaca aaaaaagaac tctaataaaa   4740

aaatatgggt agcttaacaa atatataaat tgatggtaaa taatttactt tttaaaattc   4800

atctatgttt ttttatatga taaca                                         4825
```

<210> SEQ ID NO 21
<211> LENGTH: 495
<212> TYPE: PRT
<213> ORGANISM: Glycine Max

<400> SEQUENCE: 21

```
Met Ala Lys Leu Val Phe Ser Leu Cys Phe Leu Leu Phe Ser Gly Cys
1               5                   10                  15

Cys Phe Ala Phe Ser Ser Arg Glu Gln Pro Gln Gln Asn Glu Cys Gln
            20                  25                  30

Ile Gln Lys Leu Asn Ala Leu Lys Pro Asp Asn Arg Ile Glu Ser Glu
        35                  40                  45

Gly Gly Leu Ile Glu Thr Trp Asn Pro Asn Asn Lys Pro Phe Gln Cys
    50                  55                  60

Ala Gly Val Ala Leu Ser Arg Cys Thr Leu Asn Arg Asn Ala Leu Arg
65                  70                  75                  80

Arg Pro Ser Tyr Thr Asn Gly Pro Gln Glu Ile Tyr Ile Gln Gln Gly
                85                  90                  95

Lys Gly Ile Phe Gly Met Ile Tyr Pro Gly Cys Pro Ser Thr Phe Glu
            100                 105                 110

Glu Pro Gln Gln Pro Gln Gln Arg Gly Gln Ser Ser Arg Pro Gln Asp
        115                 120                 125

Arg His Gln Lys Ile Tyr Asn Phe Arg Glu Gly Asp Leu Ile Ala Val
    130                 135                 140

Pro Thr Gly Val Ala Trp Trp Met Tyr Asn Asn Glu Asp Thr Pro Val
```

```
145                 150                 155                 160

Val Ala Val Ser Ile Ile Asp Thr Asn Ser Leu Glu Asn Gln Leu Asp
                165                 170                 175

Gln Met Pro Arg Arg Phe Tyr Leu Ala Gly Asn Gln Glu Gln Glu Phe
            180                 185                 190

Leu Lys Tyr Gln Gln Glu Gln Gly Gly His Gln Ser Gln Lys Gly Lys
        195                 200                 205

His Gln Gln Glu Glu Glu Asn Glu Gly Gly Ser Ile Leu Ser Gly Phe
    210                 215                 220

Thr Leu Glu Phe Leu Glu His Ala Phe Ser Val Asp Lys Gln Ile Ala
225                 230                 235                 240

Lys Asn Leu Gln Gly Glu Asn Glu Gly Glu Asp Lys Gly Ala Ile Val
                245                 250                 255

Thr Val Lys Gly Gly Leu Ser Val Ile Lys Pro Pro Thr Asp Glu Gln
            260                 265                 270

Gln Gln Arg Pro Gln Glu Glu Glu Glu Glu Glu Glu Asp Glu Lys Pro
        275                 280                 285

Gln Cys Lys Gly Lys Asp Lys His Cys Gln Arg Pro Arg Gly Ser Gln
    290                 295                 300

Ser Lys Ser Arg Arg Asn Gly Ile Asp Glu Thr Ile Cys Thr Met Arg
305                 310                 315                 320

Leu Arg His Asn Ile Gly Gln Thr Ser Ser Pro Asp Ile Tyr Asn Pro
                325                 330                 335

Gln Ala Gly Ser Val Thr Thr Ala Thr Ser Leu Asp Phe Pro Ala Leu
            340                 345                 350

Ser Trp Leu Arg Leu Ser Ala Glu Phe Gly Ser Leu Arg Lys Asn Ala
        355                 360                 365

Met Phe Val Pro His Tyr Asn Leu Asn Ala Asn Ser Ile Ile Tyr Ala
    370                 375                 380

Leu Asn Gly Arg Ala Leu Ile Gln Val Val Asn Cys Asn Gly Glu Arg
385                 390                 395                 400

Val Phe Asp Gly Glu Leu Gln Glu Gly Arg Val Leu Ile Val Pro Gln
                405                 410                 415

Asn Phe Val Val Ala Ala Arg Ser Gln Ser Asp Asn Phe Glu Tyr Val
            420                 425                 430

Ser Phe Lys Thr Asn Asp Thr Pro Met Ile Gly Thr Leu Ala Gly Ala
        435                 440                 445

Asn Ser Leu Leu Asn Ala Leu Pro Glu Glu Val Ile Gln His Thr Phe
    450                 455                 460

Asn Leu Lys Ser Gln Gln Ala Arg Gln Ile Lys Asn Asn Asn Pro Phe
465                 470                 475                 480

Lys Phe Leu Val Pro Pro Gln Glu Ser Gln Lys Arg Ala Val Ala
                485                 490                 495


<210> SEQ ID NO 22
<211> LENGTH: 3565
<212> TYPE: DNA
<213> ORGANISM: Glycine Max

<400> SEQUENCE: 22

ccagagagca gcctcagcaa acaatgcagg acaactcagc atctattttt tttctctcaa      60

ccttttcac atcttaagta gtctgcaccc tttatatata taacttattt cttacctttt      120

acattatgta acttttatca ccaaaaccaa caactttaaa tttttattaa atagactcca     180
```

```
caagtaactt gacactctta cattcatcga cattaacttt tatctgtttt ataaatatta    240
ttgtgatata atttaatcaa aataaccaca aactttcata aaaggttctt attaagcatg    300
gcatttaata agcaaaaaca actcaatcac tttcatatag gaggtagcct aagtacgtac    360
tcaaaatgtc aacaaataaa aaaaaagttg ctttaataat gccaaaacaa attaataaaa    420
cacttacaac accggatttt ttttaattaa aatgtgccat ttaggataaa tagttaatat    480
ttttaataat tatttaaaaa gccgtatcta ctaaaatgat ttttatttgg ttgaaaatgt    540
taatatgttt aaatcaacac aatctatcaa aattaaacta aaaaaaaaat aagtgtacgt    600
ggttaacatt agtacagtaa tataagagga aaatgagaaa ttaagaaatt gaaagcgagt    660
ctaatttata aattatgaac ctgcatatat aaaaggaaag aaagaatcca ggaagaaaag    720
aaatgaaacc atgcatggtc ccctcgtcat cacgagtttc tgccatttgc aatagaaaca    780
ctgaaacacc tttctctttg tcacttaatt gagatgccga agccacctca caccatgaac    840
ttcatgaggt gtagcaccca aggcttccat agccatgcat actgaagaat gtctcaagct    900
cagcacccta cttctgtgac gtgtccctca ttcaccttcc tctcttccct ataaataacc    960
acgcctcagg ttctccgctt cacaacacaa acattctctc cattggtcct taaacactca   1020
tcagtcatca ccatggccaa gctagttttt tccctttgtt ttctgctttt cagtggctgc   1080
tgcttcgctt tcagttccat gggtgctttc actgagaagc aagaggcttt ggtgagtagc   1140
tcattcgaag cattcaaggc aaacattcct caatacagcg ttgtgttcta cacttcgata   1200
ctggagaaag cacccgcagc aaaggacttg ttctcgtttc tatctaatgg agtagatcct   1260
agtaatccta agctcacggg ccatgctgaa aagctttttg gattggtgcg tgactcagct   1320
ggtcaactta aagcaaatgg aacagtagtg gctgatgccg cacttggttc tatccatgcc   1380
caaaaagcaa tcactgatcc tcagttcgtg gtggttaaag aagcactgct gaaaacaata   1440
aaggaggcag ttggggacaa atggagtgat gaattgagca gtgcttggga agtagcctat   1500
gatgaattgg cagcagctat taagaaggca tttagcagaa gaaatggcat tgacgagacc   1560
atatgcacca tgagacttcg ccacaacatt ggccagactt catcacctga catctacaac   1620
cctcaagccg gtagcgtcac aaccgccacc agccttgact tcccagccct ctcgtggctc   1680
agactcagtg ctgagtttgg atctctccgc aagaatgcaa tgttcgtgcc acactacaac   1740
ctgaacgcga acagcataat atacgcattg aatggacggg cattgataca agtggtgaat   1800
tgcaacggtg agagagtgtt tgatggagag ctgcaagagg gacgggtgct gatcgtgcca   1860
caaaactttg tggtggctgc aagatcacag agtgacaact tcgagtatgt gtcattcaag   1920
accaatgata cacccatgat cggcactctt gcaggggcaa actcattgtt gaacgcatta   1980
ccagaggaag tgattcagca cactttcaac ctaaaaagcc agcaggccag gcagataaag   2040
aacaacaacc ctttcaagtt cctggttcca cctcaggagt ctcagaagag agctgtggct   2100
tagagccctt tttgtatgtg ctaccccact tttgtctttt tggcaatagt gctagcaacc   2160
aataaataat aataataata atgaataaga aaacaaaggc tttagcttgc cttttgttca   2220
ctgtaaaata ataatgtaag tactctctat aatgagtcac gaaacttttg cgggaataaa   2280
aggagaaatt ccaatgagtt ttctgtcaaa tcttcttctg tctctctctc tctctctttt   2340
tttttccttt cttctgagct tcttgcaaaa caaaaggcaa acaataacga ttggtccaat   2400
gatagttagc ttaatcgatg atatctttag gaagtgttgg caggacagga catgatgtag   2460
aagactaaaa ttgaaagtat tgcagaccca atagttgaag attaacttta agaattaaga   2520
cgtctgttag gaagaagcca ttgcaaccaa taaagcatag tagatagtta gttaaatctg   2580
```

ttgggttagt taccaacaag ttgttaatac tgttgagtta gttatgcatg taaataattg 2640
tagtatataa gagttgcagt aatgaataaa agacatgcag aaaaacttag aatcagttta 2700
gttgttatgg agagggtgag atagtgcctt tgttcgaggc aaggctcctc ctaagaaagt 2760
ctgaaactga ttttaaactt ttctgcatgg cttttattca ttattgcaac tcttatatac 2820
tacaattatt tacatgcata actaactcaa caaactaatg gtattaacaa cttgttggta 2880
actaacccaa cagatttaac taactatcta ctatgcttta ttggttgcaa tggcttcttc 2940
ctaacaacgt cttatcaggt tcttcatgac ttggagctca acccaacttg gaaagttcga 3000
gagtatttgg accattgtgc tttgtgtctt caaacataaa acatcgctcc aaatttaaca 3060
tgggagctaa aaaatgtgtt tttctgggat tttaattttc aacagagtca aggatggtgt 3120
tgcatatgat gtcttgatgt ccattgtcca cactaaatag atattggttt caagaaatat 3180
taatttcatt ttcatgactt tcaattcata aaccttaaac gaatattaat ttaaaatcta 3240
tcctcaaatg ataaatttaa aaaaaaatta cccccaatcg gtaatttgac tcacaagtta 3300
gttagttgat attttgaagc ttgaaattcg acatggacat cagacacaat atgagcacag 3360
acactctcgc atagctaatg tgtaaaacat agaatgacag gacatcacat atatttttac 3420
acacacaaaa aaagaactct aataaaaaaa tatgggtagc ttaacaaata tataaattga 3480
tggtaaataa tttacttttt aaaattcatc tatgtttttt tatatgataa caaggcgcgt 3540
ttgaaagcaa aagcagaaga aatgg 3565

<210> SEQ ID NO 23
<211> LENGTH: 2508
<212> TYPE: DNA
<213> ORGANISM: Glycine Max

<400> SEQUENCE: 23
ccagagagca gcctcagcaa acaatgcagg acaactcagc atctattttt tttctctcaa 60
cctttttcac atcttaagta gtctgcaccc tttatatata taacttattt cttacctttt 120
acattatgta actttttatca ccaaaaccaa caactttaaa tttttattaa atagactcca 180
caagtaactt gacactctta cattcatcga cattaacttt tatctgtttt ataaatatta 240
ttgtgatata atttaatcaa aataaccaca aactttcata aaaggttctt attaagcatg 300
gcatttaata agcaaaaaca actcaatcac tttcatatag gaggtagcct aagtacgtac 360
tcaaaatgtc aacaaataaa aaaaaagttg ctttaataat gccaaaacaa attaataaaa 420
cacttacaac accggatttt ttttaattaa aatgtgccat ttaggataaa tagttaatat 480
ttttaataat tatttaaaaa gccgtatcta ctaaaatgat ttttatttgg ttgaaaatgt 540
taatatgttt aaatcaacac aatctatcaa aattaaacta aaaaaaaaat aagtgtacgt 600
ggttaacatt agtacagtaa tataagagga aaatgagaaa ttaagaaatt gaaagcgagt 660
ctaatttata aattatgaac ctgcatatat aaaaggaaag aaagaatcca ggaagaaaag 720
aaatgaaacc atgcatggtc ccctcgtcat cacgagtttc tgccatttgc aatagaaaca 780
ctgaaacacc tttctctttg tcacttaatt gagatgccga agccacctca caccatgaac 840
ttcatgaggt gtagcaccca aggcttccat agccatgcat actgaagaat gtctcaagct 900
cagcacccta cttctgtgac gtgtccctca ttcaccttcc tctcttccct ataaataacc 960
acgcctcagg ttctccgctt cacaacacaa acattctctc cattggtcct taaacactca 1020
tcagtcatca ccatgggtgc tttcactgag aagcaagagg ctttggtgag tagctcattc 1080

```
gaagcattca aggcaaacat tcctcaatac agcgttgtgt tctacacttc gatactggag   1140

aaagcacccg cagcaaagga cttgttctcg tttctatcta atggagtaga tcctagtaat   1200

cctaagctca cgggccatgc tgaaaagctt tttggattgg tgcgtgactc agctggtcaa   1260

cttaaagcaa atggaacagt agtggctgat gccgcacttg gttctatcca tgcccaaaaa   1320

gcaatcactg atcctcagtt cgtggtggtt aaagaagcac tgctgaaaac aataaaggag   1380

gcagttgggg acaaatggag tgatgaattg agcagtgctt gggaagtagc ctatgatgaa   1440

ttggcagcag ctattaagaa ggcattttag agcgcttttt gtatgtgcta ccccactttt   1500

gtctttttgg caatagtgct agcaaccaat aaataataat aataataatg aataagaaaa   1560

caaaggcttt agcttgcctt ttgttcactg taaaataata atgtaagtac tctctataat   1620

gagtcacgaa acttttgcgg gaataaaagg agaaattcca atgagttttc tgtcaaatct   1680

tcttctgtct ctctctctct ctcttttttt ttcctttctt ctgagcttct tgcaaaacaa   1740

aaggcaaaca ataacgattg gtccaatgat agttagctta atcgatgata tctttaggaa   1800

gtgttggcag gacaggacat gatgtagaag actaaaattg aaagtattgc agacccaata   1860

gttgaagatt aactttaaga attaagacgt ctgttaggaa gaagccattg caaccaataa   1920

agcatagtag atagttagtt aaatctgttg ggttagttac caacaagttg ttaatactgt   1980

tgagttagtt atgcatgtaa ataattgtag tatataagag ttgcagtaat gaataaaaga   2040

catgcagaaa aacttagaat cagtttagtt gttatggaga gggtgagata gtgcctttgt   2100

tcgaggcaag gctcctccta agaaagtctg aaactgattt taaacttttc tgcatggctt   2160

ttattcatta ttgcaactct tatatactac aattatttac atgcataact aactcaacaa   2220

actaatggta ttaacaactt gttggtaact aacccaacag atttaactaa ctatctacta   2280

tgctttattg gttgcaatgg cttcttccta acaacgtctt atcaggttct tcatgacttg   2340

gagctcaacc caacttggaa agttcgagag tatttggacc attgtgcttt gtgtcttcaa   2400

acataaaaca tcgctccaaa tttaacatgg gagctaaaaa atgtgttttt ctgggatttt   2460

aattttcaac agagaaggcg cgtttccttt ttgtatgtgc taccccac                 2508


<210> SEQ ID NO 24
<211> LENGTH: 20
<212> TYPE: DNA
<213> ORGANISM: Glycine max

<400> SEQUENCE: 24

gatacgtgga tatattattg                                                  20


<210> SEQ ID NO 25
<211> LENGTH: 20
<212> TYPE: DNA
<213> ORGANISM: Glycine max

<400> SEQUENCE: 25

gaattaagcg atgaagatca                                                  20


<210> SEQ ID NO 26
<211> LENGTH: 20
<212> TYPE: DNA
<213> ORGANISM: Glycine max

<400> SEQUENCE: 26

gttgtctcta tgttattgtt                                                  20
```

<210> SEQ ID NO 27
<211> LENGTH: 20
<212> TYPE: DNA
<213> ORGANISM: Glycine max

<400> SEQUENCE: 27
gttgttgtgt agcaatccga 20

<210> SEQ ID NO 28
<211> LENGTH: 20
<212> TYPE: DNA
<213> ORGANISM: Glycine max

<400> SEQUENCE: 28
ggcaacgagc gtggcatgct 20

<210> SEQ ID NO 29
<211> LENGTH: 20
<212> TYPE: DNA
<213> ORGANISM: Glycine max

<400> SEQUENCE: 29
gtcagtttgt gtctcattaa 20

<210> SEQ ID NO 30
<211> LENGTH: 20
<212> TYPE: DNA
<213> ORGANISM: Glycine max

<400> SEQUENCE: 30
gtcagtttct gtctcattac 20

<210> SEQ ID NO 31
<211> LENGTH: 603
<212> TYPE: DNA
<213> ORGANISM: Glycine Max

<400> SEQUENCE: 31
atggcttcct caatgatctc ctccccagct gttaccaccg tcaaccgtgc cggtgccggc 60
atggttgctc cattcaccgg cctcaaatcc atggctggct tccccacgag gaagaccaac 120
aatgacatta cctccattgc tagcaacggt ggaagagtac aatgcatggg tgctttcact 180
gagaagcaag aggctttggt gagtagctca ttcgaagcat tcaaggcaaa cattcctcaa 240
tacagcgttg tgttctacac ttcgatactg gagaaagcac ccgcagcaaa ggacttgttc 300
tcgtttctat ctaatggagt agatcctagt aatcctaagc tcacgggcca tgctgaaaag 360
ctttttggat tggtgcgtga ctcagctggt caacttaaag caaatggaac agtagtggct 420
gatgccgcac ttggttctat ccatgcccaa aaagcaatca ctgatcctca gttcgtggtg 480
gttaaagaag cactgctgaa aacaataaag gaggcagttg ggacaaatg gagtgatgaa 540 ttgagcagtg cttgggaagt agcctatgat gaattggcag cagctattaa gaaggcattt 600
tag 603

<210> SEQ ID NO 32
<211> LENGTH: 200
<212> TYPE: PRT
<213> ORGANISM: Glycine Max

<400> SEQUENCE: 32

Met Ala Ser Ser Met Ile Ser Ser Pro Ala Val Thr Thr Val Asn Arg
1 5 10 15

```
Ala Gly Ala Gly Met Val Ala Pro Phe Thr Gly Leu Lys Ser Met Ala
            20                  25                  30

Gly Phe Pro Thr Arg Lys Thr Asn Asn Asp Ile Thr Ser Ile Ala Ser
        35                  40                  45

Asn Gly Gly Arg Val Gln Cys Met Gly Ala Phe Thr Glu Lys Gln Glu
    50                  55                  60

Ala Leu Val Ser Ser Ser Phe Glu Ala Phe Lys Ala Asn Ile Pro Gln
65                  70                  75                  80

Tyr Ser Val Val Phe Tyr Thr Ser Ile Leu Glu Lys Ala Pro Ala Ala
                85                  90                  95

Lys Asp Leu Phe Ser Phe Leu Ser Asn Gly Val Asp Pro Ser Asn Pro
            100                 105                 110

Lys Leu Thr Gly His Ala Glu Lys Leu Phe Gly Leu Val Arg Asp Ser
        115                 120                 125

Ala Gly Gln Leu Lys Ala Asn Gly Thr Val Val Ala Asp Ala Ala Leu
    130                 135                 140

Gly Ser Ile His Ala Gln Lys Ala Ile Thr Asp Pro Gln Phe Val Val
145                 150                 155                 160

Val Lys Glu Ala Leu Leu Lys Thr Ile Lys Glu Ala Val Gly Asp Lys
                165                 170                 175

Trp Ser Asp Glu Leu Ser Ser Ala Trp Glu Val Ala Tyr Asp Glu Leu
            180                 185                 190

Ala Ala Ala Ile Lys Lys Ala Phe
        195                 200


<210> SEQ ID NO 33
<211> LENGTH: 20
<212> TYPE: PRT
<213> ORGANISM: Glycine max

<400> SEQUENCE: 33

Lys Ala Asn Gly Thr Val Val Ala Asp Ala Ala Leu Gly Ser Ile His
1               5                   10                  15

Ala Gln Lys Ala
            20


<210> SEQ ID NO 34
<211> LENGTH: 13
<212> TYPE: PRT
<213> ORGANISM: Glycine max

<400> SEQUENCE: 34

Lys Ala Ile Thr Asp Pro Gln Phe Val Val Val Lys Glu
1               5                   10


<210> SEQ ID NO 35
<211> LENGTH: 100
<212> TYPE: DNA
<213> ORGANISM: Glycine max

<400> SEQUENCE: 35

atgccccatt tttctctctc ccctctctcc tgtgcacctt ctcctctccc acctcgccgc     60

cgaatctttc tcgctcctcc ccgaaccgcc gcatcttccg                          100


<210> SEQ ID NO 36
<211> LENGTH: 83
<212> TYPE: PRT
<213> ORGANISM: Glycine max
```

<400> SEQUENCE: 36

```
Met Pro His Phe Ser Leu Ser Pro Leu Ser Cys Ala Pro Ser Pro Leu
1               5                   10                  15

Pro Pro Arg Arg Arg Ile Phe Leu Ala Pro Pro Arg Thr Ala Ala Ser
            20                  25                  30

Ser Ala Thr Asp Ala Ala Ser Ser Ser Thr Ser Ser Ser Ala Ser Asn
        35                  40                  45

Phe Ala Pro Lys Val Val Val Thr Arg Glu Arg Gly Lys Asn Ala Lys
    50                  55                  60

Leu Ile Ala Ala Leu Ala Lys His Glu Ile Asn Cys Leu Glu Leu Pro
65                  70                  75                  80

Leu Ile Glu
```

<210> SEQ ID NO 37
<211> LENGTH: 1413
<212> TYPE: DNA
<213> ORGANISM: Glycine max

<400> SEQUENCE: 37

```
atggctgttt cggctatcac aggagcgagg ctaaccctag ggatagggtt ggcgatacct     60
ctttcctctc ccacgcgctc tcgaaccgtc gcaatggccg tatccgtcga ccccaagacc    120
gacaacaaac tcactcttac caagtccgag gaagctttcg ctgctgccaa ggagctgatg    180
cctggaggtg tcaactcccc agttcgtgcc ttcaaatccg tgggtggtca accaattgtg    240
attgattcag tcaaagggtc tcgtatgtgg gacatcgacg gcaatgagta cattgactac    300
gtcggttctt ggggtcccgc aatcattggt cacgctgatg atcaagtgct ttcagctctg    360
gttgaaacca tgaagaaagg aactagcttt ggtgcaccct gtctgctgga aaacactttg    420
gcagagctgg ttatcaatgc ggtccccagc attgaaatgg ttcgctttgt caattcaggc    480
accgaagctt gcatgggtgc actacgtctc gcccgagctt ataccggaag agagaagatc    540
atcaagtttg agggctgtta ccatggccat gctgatcctt ttcttgttaa ggcaggtagt    600
ggagttgcca ccttgggact tcctgattct cccggtgtcc ccaaagctgc cacttttgaa    660
acccttacag ccccctacaa tgacactgcc gccgttgaga agctctttga ggctaacaaa    720
ggagaaatcg ctgctgtttt cctcgaacct gttgttggaa acgctggttt cattgttcct    780
aaacccgatt ttcataattt cttgcgcaag atcaccaagg agaacaatac ccttcttgtg    840
tttgatgaag ttatgactgg gtttcgtttg tcatacggag gtgctcaaga gtattttggc    900
ataactcctg atataacaac tctaggaaag atcattggtg gaggtctgcc ggtgggggct    960
tatggaggga ggagggatat tatggagaag gtggcaccag ctggcccaat gtatcaggct   1020
gggaccttga gtgggaaccc tttggccatg actgcaggaa tacagaccct gcagcgtatt   1080
aaggagccag gaacttatga gtacttggac aaaatcaccg gtgagcttgt tcagggcatt   1140
attgaagctg ggaagagggc aggccatgca atatgtggtg gtcatataag ggggatgttt   1200
gggtttttct tcacagaagg accagtgtat aattttgcag atgccaaaaa gagtgatacg   1260
gacaagtttg ctaggttctt ttggggaatg ttggcggaag gtgtctattt ggcaccttcc   1320
cagtttgagg ctggctttac cagcttggca catacctctg atgacataaa aaagacaata   1380
gccgctgctg agaaggtttt cagggagatc tga                                1413
```

<210> SEQ ID NO 38
<211> LENGTH: 470

```
<212> TYPE: PRT
<213> ORGANISM: Glycine max

<400> SEQUENCE: 38

Met Ala Val Ser Ala Ile Thr Gly Ala Arg Leu Thr Leu Gly Ile Gly
1               5                   10                  15

Leu Ala Ile Pro Leu Ser Ser Pro Thr Arg Ser Arg Thr Val Ala Met
            20                  25                  30

Ala Val Ser Val Asp Pro Lys Thr Asp Asn Lys Leu Thr Leu Thr Lys
        35                  40                  45

Ser Glu Glu Ala Phe Ala Ala Ala Lys Glu Leu Met Pro Gly Gly Val
    50                  55                  60

Asn Ser Pro Val Arg Ala Phe Lys Ser Val Gly Gly Gln Pro Ile Val
65                  70                  75                  80

Ile Asp Ser Val Lys Gly Ser Arg Met Trp Asp Ile Asp Gly Asn Glu
                85                  90                  95

Tyr Ile Asp Tyr Val Gly Ser Trp Gly Pro Ala Ile Ile Gly His Ala
            100                 105                 110

Asp Asp Gln Val Leu Ser Ala Leu Val Glu Thr Met Lys Lys Gly Thr
        115                 120                 125

Ser Phe Gly Ala Pro Cys Leu Leu Glu Asn Thr Leu Ala Glu Leu Val
    130                 135                 140

Ile Asn Ala Val Pro Ser Ile Glu Met Val Arg Phe Val Asn Ser Gly
145                 150                 155                 160

Thr Glu Ala Cys Met Gly Ala Leu Arg Leu Ala Arg Ala Tyr Thr Gly
                165                 170                 175

Arg Glu Lys Ile Ile Lys Phe Glu Gly Cys Tyr His Gly His Ala Asp
            180                 185                 190

Pro Phe Leu Val Lys Ala Gly Ser Gly Val Ala Thr Leu Gly Leu Pro
        195                 200                 205

Asp Ser Pro Gly Val Pro Lys Ala Ala Thr Phe Glu Thr Leu Thr Ala
    210                 215                 220

Pro Tyr Asn Asp Thr Ala Ala Val Glu Lys Leu Phe Glu Ala Asn Lys
225                 230                 235                 240

Gly Glu Ile Ala Ala Val Phe Leu Glu Pro Val Val Gly Asn Ala Gly
                245                 250                 255

Phe Ile Val Pro Lys Pro Asp Phe His Asn Phe Leu Arg Lys Ile Thr
            260                 265                 270

Lys Glu Asn Asn Thr Leu Leu Val Phe Asp Glu Val Met Thr Gly Phe
        275                 280                 285

Arg Leu Ser Tyr Gly Gly Ala Gln Glu Tyr Phe Gly Ile Thr Pro Asp
    290                 295                 300

Ile Thr Thr Leu Gly Lys Ile Ile Gly Gly Gly Leu Pro Val Gly Ala
305                 310                 315                 320

Tyr Gly Gly Arg Arg Asp Ile Met Glu Lys Val Ala Pro Ala Gly Pro
                325                 330                 335

Met Tyr Gln Ala Gly Thr Leu Ser Gly Asn Pro Leu Ala Met Thr Ala
            340                 345                 350

Gly Ile Gln Thr Leu Gln Arg Ile Lys Glu Pro Gly Thr Tyr Glu Tyr
        355                 360                 365

Leu Asp Lys Ile Thr Gly Glu Leu Val Gln Gly Ile Ile Glu Ala Gly
    370                 375                 380

Lys Arg Ala Gly His Ala Ile Cys Gly Gly His Ile Arg Gly Met Phe
385                 390                 395                 400
```

```
Gly Phe Phe Phe Thr Glu Gly Pro Val Tyr Asn Phe Ala Asp Ala Lys
                405                 410                 415

Lys Ser Asp Thr Asp Lys Phe Ala Arg Phe Phe Trp Gly Met Leu Ala
            420                 425                 430

Glu Gly Val Tyr Leu Ala Pro Ser Gln Phe Glu Ala Gly Phe Thr Ser
        435                 440                 445

Leu Ala His Thr Ser Asp Asp Ile Lys Lys Thr Ile Ala Ala Ala Glu
    450                 455                 460

Lys Val Phe Arg Glu Ile
465                 470


<210> SEQ ID NO 39
<211> LENGTH: 918
<212> TYPE: DNA
<213> ORGANISM: Glycine max

<400> SEQUENCE: 39

atgcttcttc aaacgaggca atttggcaca gcgtgtccat gggtcagact cacacccgca     60

agcaaaagaa atagctcagt ctcattgaga aggagcaatt gtggcccaaa atgttcggtg    120

tcccaattgg aattgaagag tgagagtgag agcaaaacga agccgtatcc agcagaggca    180

tcgaggacca taatggagtt ggctaaggtg ggcacgctgt gtacgttgac ccaagagggt    240

ttgccccttg gtactggggt tcgattcgcg gttgaccctg aacatggcac tcccttgttc    300

tgcttcaatt ccactgacaa cactaacatc ccctcttctc ttcatgttca gtttgaacaa    360

tttggattgc gcactcctca gtgcactatt caaggaaccc ttaccaaacc acaggatcca    420

aagcgtcttg tttctgtgtg gaggaaaagg tttggagaag aagttgatcg agattttatt    480

tacattattg ccgtggatcg ggtactccaa ttggaagaca ttcaggagga tggcatatgg    540

gtcacctctt cagattacaa aaatgctcaa cccgatcctc ttcgagactc tgcacacaac    600

ttagtcactg aaatcaacac caacaatatg gaagacatta ctcgcttttg caatgtctac    660

gttgatttgg atttcctggt ctccgaggca aagatgctat gggttgatcg cttgggcttt    720

gacatgcgtt tgtcttcccc tcacaaaggc gtgtttgacg tccgcattcc tttccccaga    780

gaagtcaccg atgagaaagg tgccaagtcg acgtttaatt gtatgtcaca actcgcttgg    840

gaggtagaaa gaaacttcca acatccagac ttttcaaagg ttaaagagtt gaagccagtc    900

aagtcccctt ttctgtaa                                                  918


<210> SEQ ID NO 40
<211> LENGTH: 305
<212> TYPE: PRT
<213> ORGANISM: Glycine max

<400> SEQUENCE: 40

Met Leu Leu Gln Thr Arg Gln Phe Gly Thr Ala Cys Pro Trp Val Arg
1               5                   10                  15

Leu Thr Pro Ala Ser Lys Arg Asn Ser Ser Val Ser Leu Arg Arg Ser
            20                  25                  30

Asn Cys Gly Pro Lys Cys Ser Val Ser Gln Leu Glu Leu Lys Ser Glu
        35                  40                  45

Ser Glu Ser Lys Thr Lys Pro Tyr Pro Ala Glu Ala Ser Arg Thr Ile
    50                  55                  60

Met Glu Leu Ala Lys Val Gly Thr Leu Cys Thr Leu Thr Gln Glu Gly
65                  70                  75                  80
```

```
Leu Pro Leu Gly Thr Gly Val Arg Phe Ala Val Asp Pro Glu His Gly
                85                  90                  95

Thr Pro Leu Phe Cys Phe Asn Ser Thr Asp Asn Thr Asn Ile Pro Ser
            100                 105                 110

Ser Leu His Val Gln Phe Glu Gln Phe Gly Leu Arg Thr Pro Gln Cys
        115                 120                 125

Thr Ile Gln Gly Thr Leu Thr Lys Pro Gln Asp Pro Lys Arg Leu Val
    130                 135                 140

Ser Val Trp Arg Lys Arg Phe Gly Glu Glu Val Asp Arg Asp Phe Ile
145                 150                 155                 160

Tyr Ile Ile Ala Val Asp Arg Val Leu Gln Leu Glu Asp Ile Gln Glu
                165                 170                 175

Asp Gly Ile Trp Val Thr Ser Ser Asp Tyr Lys Asn Ala Gln Pro Asp
            180                 185                 190

Pro Leu Arg Asp Ser Ala His Asn Leu Val Thr Glu Ile Asn Thr Asn
        195                 200                 205

Asn Met Glu Asp Ile Thr Arg Phe Cys Asn Val Tyr Val Asp Leu Asp
    210                 215                 220

Phe Leu Val Ser Glu Ala Lys Met Leu Trp Val Asp Arg Leu Gly Phe
225                 230                 235                 240

Asp Met Arg Leu Ser Ser Pro His Lys Gly Val Phe Asp Val Arg Ile
                245                 250                 255

Pro Phe Pro Arg Glu Val Thr Asp Glu Lys Gly Ala Lys Ser Thr Phe
            260                 265                 270

Asn Cys Met Ser Gln Leu Ala Trp Glu Val Glu Arg Asn Phe Gln His
        275                 280                 285

Pro Asp Phe Ser Lys Val Lys Glu Leu Lys Pro Val Lys Ser Pro Phe
    290                 295                 300

Leu
305
```

<210> SEQ ID NO 41
<211> LENGTH: 1149
<212> TYPE: DNA
<213> ORGANISM: Glycine max

<400> SEQUENCE: 41

```
atggaagcca tattcgccac caaacccgct tcccattctc tcctcttaac taaactctct     60

ccgaatccca aacacttgtt ccctccacac caacaatcct ttcacaacat ccgccacaaa    120

cccacgcgct tccgccccgt caccgctgtt ttccaaaacc aacatcaaca agatgcagct    180

gcagcttcca accacaccga agatgagtcc tacggcgaag tcaaaggcat cattggaagc    240

agagccttgg aagccgccac cggaatggag tacctcatcg agtggaacga cggccacgcg    300

ccgtcctggg ttcccgccga cttcatagcc aaagacgtcg tcgacgagta cgaaactccc    360

tggtggactg ccgccaagaa agccgacgag tccgcgttga aaaacttaac caaatccgac    420

gacggccgcg acgtcgacgc cgtggacgcc gacggccgca ctgcgctcct cttcgtcgcc    480

ggactcggct cggagtcctg cgtgaagctg ctagcggagg ccggcgcgaa tctggaccac    540

cgcgaccgga gcggcggcct cgcggctctg cacatggcgg cggggtacgt caggcccggc    600

gtggcgaagg ttctcttgga tctcggcgcg gatcccgagg tggcggacga ccgcgggaga    660

acggcgttgg atctggcgag ggagattctg aaggtgacgc cgaaggggaa tccgatgcag    720

ttcggacgca ggattggact ggaaggtgtg attagggttt tggaaggggc agtgttcgag    780
```

```
tacgcggagg tgcaggagat tctggaacgg agaggaaagg gtgagaattt ggagtatctt    840

gtgcggtgga aggacggtgg tgccaacgag tgggtgaagg cgaagtttgt ggcggaggat    900

ttggtgaaag actacgaggc tggcctcgag tacgccgtcg ctgaggcggt gctcgcgaaa    960

agggtagcgg atgaagggac gccggagttt ttggttaaat gggccgattt ggaggagccc   1020

acatgggagc ccgaggagaa tgtggaccca gagcttgtca aagctttcga gggaagtaac   1080

aaccaggccc agcccagtag taatgggccc gctgtggtct tttccaatca ggatagccct   1140

agcctgtga                                                           1149


<210> SEQ ID NO 42
<211> LENGTH: 382
<212> TYPE: PRT
<213> ORGANISM: Glycine max

<400> SEQUENCE: 42

Met Glu Ala Ile Phe Ala Thr Lys Pro Ala Ser His Ser Leu Leu Leu
1               5                   10                  15

Thr Lys Leu Ser Pro Asn Pro Lys His Leu Phe Pro Pro His Gln Gln
            20                  25                  30

Ser Phe His Asn Ile Arg His Lys Pro Thr Arg Phe Arg Pro Val Thr
        35                  40                  45

Ala Val Phe Gln Asn Gln His Gln Gln Asp Ala Ala Ala Ala Ser Asn
    50                  55                  60

His Thr Glu Asp Glu Ser Tyr Gly Glu Val Lys Gly Ile Ile Gly Ser
65                  70                  75                  80

Arg Ala Leu Glu Ala Ala Thr Gly Met Glu Tyr Leu Ile Glu Trp Asn
                85                  90                  95

Asp Gly His Ala Pro Ser Trp Val Pro Ala Asp Phe Ile Ala Lys Asp
            100                 105                 110

Val Val Asp Glu Tyr Glu Thr Pro Trp Trp Thr Ala Ala Lys Lys Ala
        115                 120                 125

Asp Glu Ser Ala Leu Lys Asn Leu Thr Lys Ser Asp Asp Gly Arg Asp
    130                 135                 140

Val Asp Ala Val Asp Ala Asp Gly Arg Thr Ala Leu Leu Phe Val Ala
145                 150                 155                 160

Gly Leu Gly Ser Glu Ser Cys Val Lys Leu Leu Ala Glu Ala Gly Ala
                165                 170                 175

Asn Leu Asp His Arg Asp Arg Ser Gly Gly Leu Ala Ala Leu His Met
            180                 185                 190

Ala Ala Gly Tyr Val Arg Pro Gly Val Ala Lys Val Leu Leu Asp Leu
        195                 200                 205

Gly Ala Asp Pro Glu Val Ala Asp Asp Arg Gly Arg Thr Ala Leu Asp
    210                 215                 220

Leu Ala Arg Glu Ile Leu Lys Val Thr Pro Lys Gly Asn Pro Met Gln
225                 230                 235                 240

Phe Gly Arg Arg Ile Gly Leu Glu Gly Val Ile Arg Val Leu Glu Gly
                245                 250                 255

Ala Val Phe Glu Tyr Ala Glu Val Gln Glu Ile Leu Glu Arg Arg Gly
            260                 265                 270

Lys Gly Glu Asn Leu Glu Tyr Leu Val Arg Trp Lys Asp Gly Gly Ala
        275                 280                 285

Asn Glu Trp Val Lys Ala Lys Phe Val Ala Glu Asp Leu Val Lys Asp
    290                 295                 300
```

```
Tyr Glu Ala Gly Leu Glu Tyr Ala Val Ala Glu Ala Val Leu Ala Lys
305                 310                 315                 320

Arg Val Ala Asp Glu Gly Thr Pro Glu Phe Leu Val Lys Trp Ala Asp
                325                 330                 335

Leu Glu Glu Pro Thr Trp Glu Pro Glu Glu Asn Val Asp Pro Glu Leu
            340                 345                 350

Val Lys Ala Phe Glu Gly Ser Asn Asn Gln Ala Gln Pro Ser Ser Asn
        355                 360                 365

Gly Pro Ala Val Val Phe Ser Asn Gln Asp Ser Pro Ser Leu
    370                 375                 380


<210> SEQ ID NO 43
<211> LENGTH: 5214
<212> TYPE: DNA
<213> ORGANISM: Glycine max

<400> SEQUENCE: 43

tctaactaag taagaaattg aagtatttta taaaaaaaaa ttgactcatc gaatttataa     60

agtaatttat gtaacaaaaa ttaagagtaa tttaaaagca atacatagat gaataggagt    120

gtttttatta ggaagaataa gagtgttaat aatatcacac gtgaacctct taaatcaagt    180

aagctaaatc tctttggtaa aattaagatt cacctacatt gttttttttt ttttatcaat    240

acctacatca atataaaaac aataattttt tatcaatacc tacattaata taaaaaaaat    300

aaatgataca gttacattaa atattcagag taaaagcttt gacactcatt tatttttatc    360

taactcaaat ataattttct ctattaaata atatttatgg tctaaatttt ttttagctat    420

attgcagctc gagtcttgat atcatgacat cttagccaac taaagctcaa ctggctcaaa    480

ggcaggaata tttcaaaaaa aattatttca tatatattaa tatattgatt aagaaaataa    540

aaaaattata ctaaaagaac catgacttta cccagcacca aggtgttcaa ttttcaaaag    600

ccacaccact ggaagaatga gaagccaaca tagtctttca tggactaaca catccacaaa    660

cgtcacggtt gtctttcatg caccacacga aattgccttt ttctttattc ttcaagaaat    720

tatggcatca attagtctta atagtcaaat tcgtaaaaac taacaaattg acttttaaaa    780

aattaaaaaa ttcaaattaa tcacgggata tgtataaatt atgatagact aatcattgta    840

aataagttaa tgataaattc tcaaaaagat aatttatttt taaattaatt attaaacatt    900

ataactaaat aataaaatga tctcacaaat taaatgacat gactaatttg ttatattttt    960

tcatatttga aaactacaat tttatgtcat ttttatggat taatttatat acttttaaga   1020

ataaatttaa ctatttactc cataaattat cgattattga tgtttactaa ttttgaagtt   1080

tttgctaaca agtgtcgtcc taaagtaatt taattttcac tcattaacaa aaaaataatt   1140

taagaattat aaaattagtt taataattga aacgagaaga aaggaagaac agattgtgag   1200

ttacagtctc tttgtcccct aacaattaat atttaatgat aaaaaatagt aatttgactg   1260

ttaaaaatta taagaaagaa aataatatat tttataaatt ctttagtatc cgaattgtat   1320

atatatttat tcaatactga ttgatacaat tcatattaat ataatcgagt ttttactgaa   1380

catacattta ttaaaaaaaa tctctctagt gtccatttat tcggcgagaa gccttctcgt   1440

gctttacaca ctttaatatt attatatccc caccccccacc aaaaaaaaaa aaactgttat   1500

atctttccag tacatttatt tcttttattt ttacaaagga aacttcacga aagtaattac   1560

aaaaaagata gtgaacatca ttttttttagt taagatgaat tttaaaatca cacttttttta   1620

tattttttttg ttacccttt cattattggg tgaaatctca tagtgaaact attaaatagt   1680
```

```
ttgggctcaa gttttattag taaagtctgc atgaaattta acttaataat agagagagtt   1740
ttggaaaggt aacgaatgtt agaaagtgtg atattattat agttttattt agattaataa   1800
ttatgtttac atgaaaattg acaatttatt tttaaaattc agagtaatac ttaaattact   1860
tatttacttt aagattttga aaagatcatt tggctcttca tcatgccgat tgacaccctc   1920
cacaagccaa gagaaactta agttgtaatt tttctaactc caagccttct atataaacac   1980
gtattggatg tgaagttgtt gcataacttg cattgaacaa tagaaataac aacaaagaaa   2040
ataagtgaaa aaagaaatat gggtgctttc actgagaagc aagaggcttt ggtgagtagc   2100
tcattcgaag cattcaaggc aaacattcct caatacagcg ttgtgttcta cacttcgtaa   2160
gttttctctt aaagcatgta tctttcattc tctgttttc ctttcgacat tttttgtgtt   2220
tgaaaagaga tagtgtcaat gtgagtgggt attttttttt attaaaaatt aacaggatac   2280
tggagaaagc acccgcagca aaggacttgt tctcgtttct atctaatgga gtagatccta   2340
gtaatcctaa gctcacgggc catgctgaaa agctttttgg attggtaagt atcatccaac   2400
taaaattata gctattttat gtgattaatt ttaagattaa acatgtattt aacactctta   2460
aacatgtatt taacactctt aagattaaac atgtatttaa ctaaaacatg tatttgctga   2520
ttattttttt tttataatta tcttgtcaca tattatatat tttttgaatt gtaggtgcgt   2580
gactcagctg gtcaacttaa agcaaatgga acagtagtgg ctgatgccgc acttggttct   2640
atccatgccc aaaaagcaat cactgatcct cagttcgtgg tatgataaat aataaaatgt   2700
tacaataaat gcacatatac ttaaatttta catggtgcag tgttatgatc atcatttttg   2760
tttagtaatg aatttactta aaatcttaaa ttatgtactt tttgaaagtt ttatatggaa   2820
ttttaattat agggaaaaat gtaagagcta atccattagt gatgttttgt ctgtaggtgg   2880
ttaaagaagc actgctgaaa acaataaagg aggcagttgg ggacaaatgg agtgatgaat   2940
tgagcagtgc ttgggaagta gcctatgatg aattggcagc agctattaag aaggcatttt   3000
aggatctact attgccgtca agtgtaataa ataaattttg tttcactaaa acttgttatt   3060
aaacaagtcc ccgatatata aatgttggtt aaaataagta aattatacgg tattgataaa   3120
caatcttaag ttttatatat agttccatat actaaagttt gtgaatcata atcgatgctt   3180
tatataaata agttcataag aatttatatg ttttaaaatt attttacccc tataaattca   3240
aataaactta actaaatggg atagatgttt tcctacgaaa aaaatgaaaa taagtaacag   3300
taaaatgcgt tagaaatagt tattgtggta gataaattca aatacattga aaatattttt   3360
atcaattaga ttaatatgcc aatgtttctg attttattac tttaaagaat agcaggggta   3420
agagggggat tagcactcaa aaactgacat gaggccagaa tgttaccatg gtagcgcaat   3480
cgatcaacta ttaacatata cagtaaatct aaaagattaa gggttcgttt cgtagaatta   3540
aaaaaaataa ttcaagtttt gaattaaaat atgatttaaa atgttaattc tatatttttt   3600
ttctttttca ctttctttct ctacaaatga gaaattagaa gctcaattcc attgcacggt   3660
atactcaaac cataattaca atttatcacg cgtaaatagc agaacgtacg ggttgctgag   3720
agactaacaa agatattcaa ggtccaattt gttatacatt tccgccactg atgaaagaac   3780
attactatgc aaattcctta tagaagaaaa catttaccct tctcaattct catttgcagc   3840
aaaatcacac tctttaagct aattgattga ttaaactggt gtagaattat aaataaatca   3900
ataaaatgag atcattttga acaaagtgaa gttgatttct cacttcacaa agttcgccaa   3960
tactgatggt aacttttagg tgtgaaataa gatgggctga ataaagtttt gaataaattg   4020
gtttcatgag cctatttgaa aaatggtttg ttttgtgtga gcgttttatt taggagaatg   4080
```

acgaaacaca tatttcgcca agagaaataa tgaaataggt gcatatttcg tcaataggaa 4140
caacgaaata ggtgtatgtt aggtcaggtg cagtgtgcag agtggatttt gtcatcctta 4200
ttggcgaaat aggtggtgct gttgctttgt caatttatct aatagtgagt tgaaaataat 4260
ttatctaata atgagtcaga aataatttat ctaataatga gtcaaaaccg ccaaaaaatc 4320
cacaaagcag caccacttat ttcgccaatg aggatggcaa aatccactct gcatgctgca 4380
cttatttcgc caatgtggat ggcgaaatcc actctgcaca ctgcacccct acgcgctgca 4440
tactgctgca cctgacctga cctacaccta tttcgctatt ccggttggcg aaatatgcac 4500
ctatttcact gttcctcttg gcgaaatatg tgtttcgcca ttcctttcag caaaacgctc 4560
acacaaaaca gaccacatta gcaaaatgtt tcaaaacaga ttgggaatta gtttctaaaa 4620
gaaacccccc gaagtcaatt tgctataaaa tttaaactta tttaaataat tgagtgcaac 4680
tgtaaactta aatgtatttt tttttgttta aacatataag tacacaaata atgaatccaa 4740
atataataaa ttcactaata actcaactcg gtcatctttg aaatcatgaa tatatttatt 4800
atatctatac ataatccaac aattatataa tgttttattt aacaaacagt gattaatgta 4860
ttgaaattaa aattaaatca ttcaggtaat accaaaattc aatcattagc agaaataatt 4920
tttgatcaga ttttatttac ttgttcgcta aattttaaat tagttagagt ttcttttctt 4980
taatgaaccg gagggtcaag ataaaaaaat acattttttt tttaataatt atcatattat 5040
aacaggtagt tatttcaaag caattcaatg cttcatttca accaccaaca tttaaaagaa 5100
ataaaataca aaatagtact cgtggttttg tgtctggaaa gctccaacca taatttaatc 5160
caaaagttgt ctattgtaac tttagcttaa ataaaccatg gtttaagact ttca 5214

<210> SEQ ID NO 44
<211> LENGTH: 100
<212> TYPE: DNA
<213> ORGANISM: Zea mays

<400> SEQUENCE: 44
ttacttctac ccgatagagc ttagaagttg gaagtaataa tttcttggtt gattgtaggc 60
ttaaccattt cttttttttt gacacgagga actcatcatg 100

<210> SEQ ID NO 45
<211> LENGTH: 2361
<212> TYPE: DNA
<213> ORGANISM: Zea mays

<400> SEQUENCE: 45
atggaggcca ccggcagggg gctgttcccg aacaagccca ccctcccggc ggggccgagg 60
aaacggggcc cgctcctccc ggccgcgccc ccgccaccgt ccccctcctc gctcccgctc 120
gactcgctcc tgctccacct caccgcgccc gcccccgcgc cggcccccgc gccgcggcgg 180
tcgcaccaga cgccgacgcc gccgcactcc ttcctctccc ccgacgcgca ggtgctggtg 240
ctcgccatct cctcgcaccc gctccccacg ctggcggcct tcctggcctc ccgccgcgac 300
gagctcctcc gcgcggacat cacgtccctg ctcaaggcgc tggagctctc ggggcactgg 360
gagtgggcgc tcgcgctcct ccggtgggca ggcaaggagg gtgccgccga cgcgtcggcg 420
ctcgagatgg tcgtccgcgc gctgggccgc gagggccagc acgacgccgt ctgcgcgctg 480
ctcgacgaaa cgccgctccc gccgggctcc cgcctcgacg tccgcgccta caccaccgtg 540
ctgcacgcgc tctcccgcgc gggccggtac gagcgcgcgc tcgagctctt cgccgagctc 600

```
cggcgccagg gggtggcgcc cacgctcgtc acctacaacg tcgtgctgga cgtgtacggg    660
cggatgggcc ggtcgtggcc gcggatcgtc gccctcctcg atgagatgcg cgccgccggg    720
gtcgagcccg acggcttcac cgccagcacg gtgatcgccg cgtgctgccg cgacgggctg    780
gttgacgagg cggtggcgtt cttcgaggac ctcaaggccc gcggccacgc cccgtgcgtc    840
gtcacgtaca cagcgttgct ccaggtgttc ggcaaggccg ggaactacac ggaggcgctg    900
cgcgtgctcg gggagatgga gcagaacggc tgccagccag atgctgtgac gtacaccgag    960
ctcgccggaa cgtacgcccg ggctgggttc ttcgaggagg ctgccaggtg cctggacaca   1020
atggcatcca agggtctgtt gccaaacgca ttcacgtaca acaccgtgat gacagcctat   1080
gggaatgttg ggaaggtgga tgaggcgctc gctctgtttg accagatgaa gaagaccggg   1140
ttcgtgccga acgtgaacac gtacaatctt gtccttggca tgcttggcaa gaagtcaagg   1200
ttcacggtga tgctagagat gcttggagag atgtcgagga gcggatgcac accgaaccgg   1260
gtaacatgga acacaatgct tgcagtctgt gggaagcgtg gcatggagga ctacgtcacc   1320
cgggttctgg aggggatgag gtcttgcggg gttgaactga gccgagacac ctacaacacc   1380
ctgatagctg cgtacggccg gtgtggctcg aggactaatg ccttcaagat gtacaacgag   1440
atgaccagcg ctggattcac cccctgcatc accacgtaca acgcgttgct gaacgtgctg   1500
tcgcggcagg gcgactggtc caccgcccag tcgatcgtaa gcaaaatgag gaccaagggg   1560
ttcaagccga acgagcagtc gtattcgctg ctgctccagt gctacgcgaa gggggggcaac   1620
gtggcaggga tagccgcgat cgagaacgag gtgtacggat caggtgccgt tttcccaagc   1680
tgggtgatcc tgaggaccct tgtcatcgcc aatttcaagt gccggcgact ggatggcatg   1740
gagacggcgt ttcaagaggt gaaggccaga ggctacaacc cggacctcgt gatattcaac   1800
tccatgctgt ccatctacgc gaagaacggg atgtacagca aggccaccga ggtcttcgac   1860
tccatcaagc ggagcgggct gagccccgac ctcatcacct acaacagcct gatggacatg   1920
tacgccaagt gcagcgagtc gtgggaggcc gagaagatac tgaaccagct caagtgctcc   1980
cagacgatga agcccgacgt ggtgtcctac aacacggtca taaacgggtt ctgcaagcag   2040
gggctggtga aagaggccca gagggtcctc tcggagatgg tcgccgacgg catggccccc   2100
tgcgccgtga cctaccacac gctcgtcggg ggttactcca gcctggagat gttcagcgag   2160
gccagggagg tcatcggcta catggtccag cacggcctca agcctatgga gctgacctac   2220
aggagagtcg tcgagagcta ctgcagagcg aagcggttcg aggaggctcg cggcttcctg   2280
tccgaggtct cggagaccga cctggatttt gacaagaagg cgctcgaagc ctatatagag   2340
gatgcgcagt ttggaaggta g                                             2361
```

<210> SEQ ID NO 46
<211> LENGTH: 786
<212> TYPE: PRT
<213> ORGANISM: Zea mays

<400> SEQUENCE: 46

```
Met Glu Ala Thr Gly Arg Gly Leu Phe Pro Asn Lys Pro Thr Leu Pro
1               5                   10                  15

Ala Gly Pro Arg Lys Arg Gly Pro Leu Leu Pro Ala Ala Pro Pro Pro
            20                  25                  30

Pro Ser Pro Ser Ser Leu Pro Leu Asp Ser Leu Leu Leu His Leu Thr
        35                  40                  45

Ala Pro Ala Pro Ala Pro Ala Pro Ala Pro Arg Arg Ser His Gln Thr
    50                  55                  60
```

```
Pro Thr Pro Pro His Ser Phe Leu Ser Pro Asp Ala Gln Val Leu Val
65                  70                  75                  80

Leu Ala Ile Ser Ser His Pro Leu Pro Thr Leu Ala Ala Phe Leu Ala
                85                  90                  95

Ser Arg Arg Asp Glu Leu Leu Arg Ala Asp Ile Thr Ser Leu Leu Lys
            100                 105                 110

Ala Leu Glu Leu Ser Gly His Trp Glu Trp Ala Leu Ala Leu Leu Arg
        115                 120                 125

Trp Ala Gly Lys Glu Gly Ala Ala Asp Ala Ser Ala Leu Glu Met Val
    130                 135                 140

Val Arg Ala Leu Gly Arg Glu Gly Gln His Asp Ala Val Cys Ala Leu
145                 150                 155                 160

Leu Asp Glu Thr Pro Leu Pro Pro Gly Ser Arg Leu Asp Val Arg Ala
                165                 170                 175

Tyr Thr Thr Val Leu His Ala Leu Ser Arg Ala Gly Arg Tyr Glu Arg
            180                 185                 190

Ala Leu Glu Leu Phe Ala Glu Leu Arg Arg Gln Gly Val Ala Pro Thr
        195                 200                 205

Leu Val Thr Tyr Asn Val Val Leu Asp Val Tyr Gly Arg Met Gly Arg
    210                 215                 220

Ser Trp Pro Arg Ile Val Ala Leu Leu Asp Glu Met Arg Ala Ala Gly
225                 230                 235                 240

Val Glu Pro Asp Gly Phe Thr Ala Ser Thr Val Ile Ala Ala Cys Cys
                245                 250                 255

Arg Asp Gly Leu Val Asp Glu Ala Val Ala Phe Phe Glu Asp Leu Lys
            260                 265                 270

Ala Arg Gly His Ala Pro Cys Val Val Thr Tyr Thr Ala Leu Leu Gln
        275                 280                 285

Val Phe Gly Lys Ala Gly Asn Tyr Thr Glu Ala Leu Arg Val Leu Gly
    290                 295                 300

Glu Met Glu Gln Asn Gly Cys Gln Pro Asp Ala Val Thr Tyr Thr Glu
305                 310                 315                 320

Leu Ala Gly Thr Tyr Ala Arg Ala Gly Phe Phe Glu Glu Ala Ala Arg
                325                 330                 335

Cys Leu Asp Thr Met Ala Ser Lys Gly Leu Leu Pro Asn Ala Phe Thr
            340                 345                 350

Tyr Asn Thr Val Met Thr Ala Tyr Gly Asn Val Gly Lys Val Asp Glu
        355                 360                 365

Ala Leu Ala Leu Phe Asp Gln Met Lys Lys Thr Gly Phe Val Pro Asn
    370                 375                 380

Val Asn Thr Tyr Asn Leu Val Leu Gly Met Leu Gly Lys Lys Ser Arg
385                 390                 395                 400

Phe Thr Val Met Leu Glu Met Leu Gly Glu Met Ser Arg Ser Gly Cys
                405                 410                 415

Thr Pro Asn Arg Val Thr Trp Asn Thr Met Leu Ala Val Cys Gly Lys
            420                 425                 430

Arg Gly Met Glu Asp Tyr Val Thr Arg Val Leu Glu Gly Met Arg Ser
        435                 440                 445

Cys Gly Val Glu Leu Ser Arg Asp Thr Tyr Asn Thr Leu Ile Ala Ala
    450                 455                 460

Tyr Gly Arg Cys Gly Ser Arg Thr Asn Ala Phe Lys Met Tyr Asn Glu
465                 470                 475                 480
```

```
Met Thr Ser Ala Gly Phe Thr Pro Cys Ile Thr Thr Tyr Asn Ala Leu
                485                 490                 495

Leu Asn Val Leu Ser Arg Gln Gly Asp Trp Ser Thr Ala Gln Ser Ile
            500                 505                 510

Val Ser Lys Met Arg Thr Lys Gly Phe Lys Pro Asn Glu Gln Ser Tyr
        515                 520                 525

Ser Leu Leu Leu Gln Cys Tyr Ala Lys Gly Gly Asn Val Ala Gly Ile
    530                 535                 540

Ala Ala Ile Glu Asn Glu Val Tyr Gly Ser Gly Ala Val Phe Pro Ser
545                 550                 555                 560

Trp Val Ile Leu Arg Thr Leu Val Ile Ala Asn Phe Lys Cys Arg Arg
                565                 570                 575

Leu Asp Gly Met Glu Thr Ala Phe Gln Glu Val Lys Ala Arg Gly Tyr
            580                 585                 590

Asn Pro Asp Leu Val Ile Phe Asn Ser Met Leu Ser Ile Tyr Ala Lys
        595                 600                 605

Asn Gly Met Tyr Ser Lys Ala Thr Glu Val Phe Asp Ser Ile Lys Arg
    610                 615                 620

Ser Gly Leu Ser Pro Asp Leu Ile Thr Tyr Asn Ser Leu Met Asp Met
625                 630                 635                 640

Tyr Ala Lys Cys Ser Glu Ser Trp Glu Ala Glu Lys Ile Leu Asn Gln
                645                 650                 655

Leu Lys Cys Ser Gln Thr Met Lys Pro Asp Val Val Ser Tyr Asn Thr
            660                 665                 670

Val Ile Asn Gly Phe Cys Lys Gln Gly Leu Val Lys Glu Ala Gln Arg
        675                 680                 685

Val Leu Ser Glu Met Val Ala Asp Gly Met Ala Pro Cys Ala Val Thr
    690                 695                 700

Tyr His Thr Leu Val Gly Gly Tyr Ser Ser Leu Glu Met Phe Ser Glu
705                 710                 715                 720

Ala Arg Glu Val Ile Gly Tyr Met Val Gln His Gly Leu Lys Pro Met
                725                 730                 735

Glu Leu Thr Tyr Arg Arg Val Val Glu Ser Tyr Cys Arg Ala Lys Arg
            740                 745                 750

Phe Glu Glu Ala Arg Gly Phe Leu Ser Glu Val Ser Glu Thr Asp Leu
        755                 760                 765

Asp Phe Asp Lys Lys Ala Leu Glu Ala Tyr Ile Glu Asp Ala Gln Phe
    770                 775                 780

Gly Arg
785
```

<210> SEQ ID NO 47
<211> LENGTH: 2490
<212> TYPE: DNA
<213> ORGANISM: Glycine max

<400> SEQUENCE: 47

```
atggagggta cccttttccc caataggcca gttttgcctg ctccttcaca caaaccaaca     60

caacaacctt tgaaattcaa gccaactttt ttgcctccac agtctccacc accaccacct    120

ccttcttttc agttagattc ccttctccaa caccttcagc atctctcttc agttcccatc    180

accactcaca ctctcacact tgtgcctcct tctcatgata acaccaaaga ttttaataat    240

tcagttcatt caaagcaccc cactttaggt tctggctcca taattgatga ggacaagttt    300

gatgatgcaa agtttggatt tttatcagac aagggtaagt tgctgttcag ttcaattgtt    360
```

```
gggtcacctt tgcatgaatt gaatgacttt ttcaactctg ttaagtttga gttgcttgag    420
gctgattttc ccagcttgtt gaaggctttg gacctttctg ggaactggga aagggcactc    480
ttgctgtttg aatggggttg gttgcatttt gggagtgatc agaatttgag gttggacaac    540
caggttgttg aattgatggt taggatattg ggagagggagt cacagcattc aattgcatcc    600
aagttgtttg atttaattcc tgtggaaaaa tactcgcttg atgtccgggc ttacaccacc    660
attcttcatt cctatgctcg cactggcaag tacaaacggg ctattgactt gtttgggaag    720
atgaaggaga ttggtcttga tccaactttg gtcacttaca atgttatgct tgatgtttac    780
ggcaagatgg gtcgttcttg ggatagaatc ttggagttgt tggatgagat gaggagtaaa    840
gggcttgagt tagatgagtt tacctgcagc actgtgattt ctgcttgtgg gagagagggt    900
atgctggatg aagcgaggaa gtttttggct gaattgaaat ttaatggcta taaaccggga    960
actgttacgt ataattctat gttgcaggtt tttggaaagg caggaattta cactgaggcc   1020
ttgagcatat tgaaagaaat ggaggataat aattgccctc ctgattctgt tacttacaat   1080
gagcttgcgg caacatatgt aagagctggt tttctggacg aagggatggc tgtcatagat   1140
acaatgacaa gcaaaggggt aatgccaaat gctattacct ataccactgt aatagatgcc   1200
tatggtaagg cgggaaggga ggatgatgca ttaaggttgt tcagcctgat gaaggacttg   1260
ggttgtgctc ccaatgtgta cacatataac tctgttcttg ccatgctagg caagaaatca   1320
agaacagaag atgttattaa ggttctctgt gagatgaaat tgaatggatg tgctcctaat   1380
cgtgctacat ggaacaccat gcttgctgta tgtagcgagg agggtaagca caattatgtt   1440
aacaaggtct tgagggaaat gaaaaactgt ggatttgagc ctgataaaga cacattcaat   1500
acattgatta gtgcatatgc tcgttgcgga tctgaagttg attctgcaaa aatgtatggg   1560
gaaatggtta aatcaggctt tactccatgt gtaacaactt ataatgctct tctaaatgcc   1620
ctggctcggc gaggtgattg gaaagcggca gaatctgtca ttcaggacat gcgaaccaag   1680
ggctttaagc ctaatgaaaa ttcatactca ctgttgctcc attgttattc caaggctggg   1740
aatgtcaagg ggatagagaa ggtcgagaaa gaaatttatg atggtcatgt ctttcctagc   1800
tggatacttt tgagaaccct tgtccttaca aaccacaagt gcagacacct taggggaatg   1860
gaaagggcat ttgatcaact gcaaaagtat ggatacaaac ctgatttggt tgtcatcaac   1920
tccatgcttt cgatgtttgc ccgaaacaag atgttttcga aggcccgtga aatgctgcat   1980
ttcattcatg aatgtggatt gcagccaaat cttttcacct acaattgctt gatggatttg   2040
tatgtccgag agggcgagtg ttggaaagca gaagaagtgc tcaagggaat tcaaaactct   2100
ggtccagagc cagatgttgt gtcttacaat actgttatca agggattttg cagaaaaggg   2160
ctcatgcagg aggctattgg agttctctca gaaatgacca ctaaggggat tcaaccaact   2220
atagttacat acaatacttt cttgtcaggc tatgcaggga tggagttgtt tgatgaagca   2280
aatgaagtca ttagatttat gattgagcac aattgcaggc caagtgaact aacttacaag   2340
attctagttg atggttactg taaagctggg aagtatgaag aagccatgga ctttgtgtct   2400
aagattaagg agcttgatat ctcctttgat gatcaatctg tgaaaagact tggttcttgt   2460
attagggaga gagtggggtc tactttgtga                                    2490
```

<210> SEQ ID NO 48
<211> LENGTH: 829
<212> TYPE: PRT
<213> ORGANISM: Glycine max

<400> SEQUENCE: 48

```
Met Glu Gly Thr Leu Phe Pro Asn Arg Pro Val Leu Pro Ala Pro Ser
1               5                   10                  15

His Lys Pro Thr Gln Gln Pro Leu Lys Phe Lys Pro Thr Phe Leu Pro
            20                  25                  30

Pro Gln Ser Pro Pro Pro Pro Pro Pro Ser Phe Gln Leu Asp Ser Leu
        35                  40                  45

Leu Gln His Leu Gln His Leu Ser Ser Val Pro Ile Thr Thr His Thr
    50                  55                  60

Leu Thr Leu Val Pro Pro Ser His Asp Asn Thr Lys Asp Phe Asn Asn
65                  70                  75                  80

Ser Val His Ser Lys His Pro Thr Leu Gly Ser Gly Ser Ile Ile Asp
                85                  90                  95

Glu Asp Lys Phe Asp Asp Ala Lys Phe Gly Phe Leu Ser Asp Lys Gly
            100                 105                 110

Lys Leu Leu Phe Ser Ser Ile Val Gly Ser Pro Leu His Glu Leu Asn
        115                 120                 125

Asp Phe Phe Asn Ser Val Lys Phe Glu Leu Leu Glu Ala Asp Phe Pro
    130                 135                 140

Ser Leu Leu Lys Ala Leu Asp Leu Ser Gly Asn Trp Glu Arg Ala Leu
145                 150                 155                 160

Leu Leu Phe Glu Trp Gly Trp Leu His Phe Gly Ser Asp Gln Asn Leu
                165                 170                 175

Arg Leu Asp Asn Gln Val Val Glu Leu Met Val Arg Ile Leu Gly Arg
            180                 185                 190

Glu Ser Gln His Ser Ile Ala Ser Lys Leu Phe Asp Leu Ile Pro Val
        195                 200                 205

Glu Lys Tyr Ser Leu Asp Val Arg Ala Tyr Thr Thr Ile Leu His Ser
    210                 215                 220

Tyr Ala Arg Thr Gly Lys Tyr Lys Arg Ala Ile Asp Leu Phe Gly Lys
225                 230                 235                 240

Met Lys Glu Ile Gly Leu Asp Pro Thr Leu Val Thr Tyr Asn Val Met
                245                 250                 255

Leu Asp Val Tyr Gly Lys Met Gly Arg Ser Trp Asp Arg Ile Leu Glu
            260                 265                 270

Leu Leu Asp Glu Met Arg Ser Lys Gly Leu Glu Leu Asp Glu Phe Thr
        275                 280                 285

Cys Ser Thr Val Ile Ser Ala Cys Gly Arg Glu Gly Met Leu Asp Glu
    290                 295                 300

Ala Arg Lys Phe Leu Ala Glu Leu Lys Phe Asn Gly Tyr Lys Pro Gly
305                 310                 315                 320

Thr Val Thr Tyr Asn Ser Met Leu Gln Val Phe Gly Lys Ala Gly Ile
                325                 330                 335

Tyr Thr Glu Ala Leu Ser Ile Leu Lys Glu Met Glu Asp Asn Asn Cys
            340                 345                 350

Pro Pro Asp Ser Val Thr Tyr Asn Glu Leu Ala Ala Thr Tyr Val Arg
        355                 360                 365

Ala Gly Phe Leu Asp Glu Gly Met Ala Val Ile Asp Thr Met Thr Ser
    370                 375                 380

Lys Gly Val Met Pro Asn Ala Ile Thr Tyr Thr Thr Val Ile Asp Ala
385                 390                 395                 400

Tyr Gly Lys Ala Gly Arg Glu Asp Asp Ala Leu Arg Leu Phe Ser Leu
                405                 410                 415
```

```
Met Lys Asp Leu Gly Cys Ala Pro Asn Val Tyr Thr Tyr Asn Ser Val
            420                 425                 430

Leu Ala Met Leu Gly Lys Lys Ser Arg Thr Glu Asp Val Ile Lys Val
        435                 440                 445

Leu Cys Glu Met Lys Leu Asn Gly Cys Ala Pro Asn Arg Ala Thr Trp
    450                 455                 460

Asn Thr Met Leu Ala Val Cys Ser Glu Glu Gly Lys His Asn Tyr Val
465                 470                 475                 480

Asn Lys Val Leu Arg Glu Met Lys Asn Cys Gly Phe Glu Pro Asp Lys
                485                 490                 495

Asp Thr Phe Asn Thr Leu Ile Ser Ala Tyr Ala Arg Cys Gly Ser Glu
            500                 505                 510

Val Asp Ser Ala Lys Met Tyr Gly Glu Met Val Lys Ser Gly Phe Thr
        515                 520                 525

Pro Cys Val Thr Thr Tyr Asn Ala Leu Leu Asn Ala Leu Ala Arg Arg
    530                 535                 540

Gly Asp Trp Lys Ala Ala Glu Ser Val Ile Gln Asp Met Arg Thr Lys
545                 550                 555                 560

Gly Phe Lys Pro Asn Glu Asn Ser Tyr Ser Leu Leu Leu His Cys Tyr
                565                 570                 575

Ser Lys Ala Gly Asn Val Lys Gly Ile Glu Lys Val Glu Lys Glu Ile
            580                 585                 590

Tyr Asp Gly His Val Phe Pro Ser Trp Ile Leu Leu Arg Thr Leu Val
        595                 600                 605

Leu Thr Asn His Lys Cys Arg His Leu Arg Gly Met Glu Arg Ala Phe
    610                 615                 620

Asp Gln Leu Gln Lys Tyr Gly Tyr Lys Pro Asp Leu Val Val Ile Asn
625                 630                 635                 640

Ser Met Leu Ser Met Phe Ala Arg Asn Lys Met Phe Ser Lys Ala Arg
                645                 650                 655

Glu Met Leu His Phe Ile His Glu Cys Gly Leu Gln Pro Asn Leu Phe
            660                 665                 670

Thr Tyr Asn Cys Leu Met Asp Leu Tyr Val Arg Glu Gly Glu Cys Trp
        675                 680                 685

Lys Ala Glu Glu Val Leu Lys Gly Ile Gln Asn Ser Gly Pro Glu Pro
    690                 695                 700

Asp Val Val Ser Tyr Asn Thr Val Ile Lys Gly Phe Cys Arg Lys Gly
705                 710                 715                 720

Leu Met Gln Glu Ala Ile Gly Val Leu Ser Glu Met Thr Thr Lys Gly
                725                 730                 735

Ile Gln Pro Thr Ile Val Thr Tyr Asn Thr Phe Leu Ser Gly Tyr Ala
            740                 745                 750

Gly Met Glu Leu Phe Asp Glu Ala Asn Glu Val Ile Arg Phe Met Ile
        755                 760                 765

Glu His Asn Cys Arg Pro Ser Glu Leu Thr Tyr Lys Ile Leu Val Asp
    770                 775                 780

Gly Tyr Cys Lys Ala Gly Lys Tyr Glu Glu Ala Met Asp Phe Val Ser
785                 790                 795                 800

Lys Ile Lys Glu Leu Asp Ile Ser Phe Asp Asp Gln Ser Val Lys Arg
                805                 810                 815

Leu Gly Ser Cys Ile Arg Glu Arg Val Gly Ser Thr Leu
            820                 825
```